United States Patent
Frykman et al.

(10) Patent No.: US 10,555,969 B2
(45) Date of Patent: *Feb. 11, 2020

(54) ZEOLITE MOLECULAR SIEVES FOR THE REMOVAL OF TOXINS

(71) Applicant: FRAMEWORKS THERAPEUTICS, LLC, Bethesda, MD (US)

(72) Inventors: Gregory K. Frykman, Washington, DC (US); Glenn H. Gruett, New London, WI (US)

(73) Assignee: FRAMEWORK THERAPEUTICS, LLC, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/622,572

(22) Filed: Jun. 14, 2017

(65) Prior Publication Data
US 2018/0169143 A1  Jun. 21, 2018

Related U.S. Application Data

(63) Continuation of application No. 10/965,799, filed on Oct. 18, 2004, now abandoned.

(60) Provisional application No. 60/512,395, filed on Oct. 20, 2003.

(51) Int. Cl.
*A61K 33/06* (2006.01)
*A61K 9/14* (2006.01)
*A61K 45/06* (2006.01)

(52) U.S. Cl.
CPC ............. *A61K 33/06* (2013.01); *A61K 9/14* (2013.01); *A61K 45/06* (2013.01)

(58) Field of Classification Search
CPC .......... A61K 33/06; A61K 45/06; A61K 9/14
See application file for complete search history.

(56) References Cited

U.S. PATENT DOCUMENTS

| | | |
|---|---|---|
| 4,016,245 A | 4/1977 | Plank et al. |
| 4,041,153 A | 8/1977 | Howard |
| 4,091,079 A | 5/1978 | Vaughan |
| 4,093,699 A | 6/1978 | Sand |
| 4,107,331 A | 8/1978 | Rosenberg |
| 4,124,686 A | 11/1978 | Grose et al. |
| 4,213,874 A | 7/1980 | Williams et al. |
| 4,251,519 A | 2/1981 | Robbins et al. |
| 4,310,440 A | 1/1982 | Wilson et al. |
| 4,333,859 A | 6/1982 | Vaughan et al. |
| 4,343,706 A | 8/1982 | Etzel et al. |
| 4,346,216 A | 8/1982 | Hinckley et al. |
| 4,348,369 A | 9/1982 | Hinchey et al. |
| 4,352,751 A | 10/1982 | Wieder et al. |
| 4,424,144 A | 1/1984 | Pryor et al. |
| 4,473,663 A | 9/1984 | Patton et al. |
| 4,503,023 A | 3/1985 | Breck et al. |
| 4,537,754 A | 8/1985 | Casci et al. |
| 4,537,771 A | 8/1985 | Greb et al. |
| 4,578,259 A | 3/1986 | Morimoto et al. |
| 4,585,780 A | 4/1986 | Hider et al. |
| 4,594,339 A | 6/1986 | Lopez et al. |
| 4,649,048 A | 3/1987 | Johnson et al. |
| 4,765,992 A | 8/1988 | Geneix et al. |
| 4,778,676 A | 10/1988 | Yang et al. |
| 4,790,991 A | 12/1988 | Shaw et al. |
| 4,812,299 A | 3/1989 | Wason |
| 4,826,793 A | 5/1989 | Velten et al. |
| 4,828,840 A | 5/1989 | Sakamoto et al. |
| 4,853,208 A | 8/1989 | Reimers et al. |
| 4,879,103 A | 10/1989 | Vaughan |
| 4,925,460 A | 5/1990 | Coe et al. |
| 4,950,952 A | 8/1990 | Aramaki |
| 4,994,191 A | 2/1991 | Kuznicki et al. |
| 5,011,667 A | 4/1991 | Kuznicki et al. |
| 5,053,139 A | 10/1991 | Dodwell et al. |
| 5,085,705 A | 2/1992 | Withiam |
| 5,091,073 A | 2/1992 | Chang et al. |
| 5,096,946 A | 3/1992 | Rainer |
| 5,116,590 A | 5/1992 | Vaughan et al. |
| 5,149,549 A | 9/1992 | Beggs |
| 5,152,813 A | 10/1992 | Coe et al. |
| 5,165,946 A | 11/1992 | Taylor et al. |
| 5,167,965 A | 12/1992 | Schulz |
| 5,171,333 A | 12/1992 | Maurer |
| 5,183,313 A | 2/1993 | Cunningham |
| 5,192,551 A | 3/1993 | Wiloughby, Jr. et al. |
| 5,230,885 A | 7/1993 | Jaxa-Chamiec et al. |
| 5,258,058 A | 11/1993 | Coe et al. |

(Continued)

FOREIGN PATENT DOCUMENTS

| | | |
|---|---|---|
| CA | 939186 | 1/1974 |
| DE | 2512212 | 9/1975 |

(Continued)

OTHER PUBLICATIONS

Pond, W. G. et al., "Decreased Absorption of Orally Administered Ammonia by Clinoptilolite in Rats (41076)", Proceedings of the Society for Experimental Biology and Medicine, vol. 166, 1981, pp. 369-373.
Chelishchev, "Use of Natural Zeolites in Chernobyl", Natural Zeolites '93, pp. 525-532 (1995).
Childhood Bood Lead Clinical Treatment Guidelines for Minnesota, 2 pages (Mar. 2001—IC# 141-0074).
Eliminating Childhood Lead Poisoning: A Federal Strategy Targeting Lead Pain Hazzards (2000).
European Office Action for European Patent Application No. 04795567.9, dated Mar. 14, 2012.
European Office Action for European Patent Application No. 04795567.9, dated Nov. 30, 2015.
Kovac, "Application of Clinoptiloite during Organophosphate Intoxication in Sheet", Natural Zeolites '93, pp. 459-466 (1995).

(Continued)

*Primary Examiner* — Rachael E Bredefeld
(74) *Attorney, Agent, or Firm* — Sughrue Mion, PLLC

(57) ABSTRACT

Medical use of natural and synthetic zeolites for treatment, prevention, and palliation in humans or animals of deleterious concentrations of ammonia, mercaptans, heavy metals and other toxins by oral administration.

8 Claims, 3 Drawing Sheets

(56) References Cited

U.S. PATENT DOCUMENTS

| | | | |
|---|---|---|---|
| 5,273,740 | A | 12/1993 | Jaxa-Chamiec et al. |
| 5,320,773 | A | 6/1994 | Perman et al. |
| 5,350,584 | A | 9/1994 | McClelland et al. |
| 5,385,876 | A | 1/1995 | Schwarz et al. |
| 5,393,511 | A | 2/1995 | Delprato et al. |
| 5,413,625 | A | 5/1995 | Chao et al. |
| 5,464,467 | A | 11/1995 | Fitch et al. |
| 5,470,435 | A | 11/1995 | Rushmere et al. |
| 5,478,604 | A | 12/1995 | Leeper |
| 5,482,693 | A | 1/1996 | Rushmere et al. |
| 5,487,882 | A | 1/1996 | Hu et al. |
| 5,494,935 | A | 2/1996 | Miller et al. |
| 5,500,212 | A | 3/1996 | Bliem et al. |
| 5,503,820 | A | 4/1996 | Moffett et al. |
| 5,543,014 | A | 8/1996 | Rushmere et al. |
| 5,556,699 | A | 9/1996 | Niira et al. |
| 5,560,829 | A | 10/1996 | Adams et al. |
| 5,578,195 | A | 11/1996 | Tissler et al. |
| 5,584,912 | A | 12/1996 | Li et al. |
| 5,591,256 | A | 1/1997 | Freeman et al. |
| 5,612,522 | A | 3/1997 | Levy |
| 5,639,492 | A | 6/1997 | Turk et al. |
| 5,641,511 | A | 6/1997 | Kuhrts |
| 5,643,560 | A | 7/1997 | Bertwitz-Larson et al. |
| 5,645,811 | A | 7/1997 | Kuhm et al. |
| 5,662,826 | A | 9/1997 | Nilsson et al. |
| 5,698,183 | A | 12/1997 | Langer et al. |
| 5,702,696 | A | 12/1997 | Mandeville, III et al. |
| 5,744,404 | A | 4/1998 | Titterson et al. |
| 5,769,938 | A | 6/1998 | Ueshima et al. |
| 5,810,920 | A | 9/1998 | Ueshima et al. |
| 5,837,238 | A | 11/1998 | Casas et al. |
| 5,863,516 | A | 1/1999 | Otterstedt et al. |
| 5,874,522 | A | 2/1999 | Figuly et al. |
| 5,882,625 | A | 3/1999 | MacDougall et al. |
| 5,935,611 | A | 8/1999 | Taborsky |
| 5,994,933 | A | 11/1999 | Yamanaka et al. |
| 6,004,527 | A | 12/1999 | Murrell et al. |
| 6,007,803 | A | 12/1999 | Mandeville, III et al. |
| 6,022,533 | A | 2/2000 | Goto et al. |
| 6,045,834 | A | 4/2000 | Howes et al. |
| 6,074,689 | A | 6/2000 | Luck et al. |
| 6,103,678 | A | 8/2000 | Masschelein et al. |
| 6,103,949 | A | 8/2000 | Demmel et al. |
| 6,107,282 | A | 8/2000 | Heerze et al. |
| 6,136,859 | A | 10/2000 | Henriksen |
| 6,180,094 | B1 | 1/2001 | Sasaki et al. |
| 6,190,561 | B1 | 2/2001 | Nagan |
| 6,264,938 | B1 | 7/2001 | Huval et al. |
| 6,270,755 | B1 | 8/2001 | Bacon Kurtz et al. |
| 6,287,576 | B1 | 9/2001 | Bgatov |
| 6,288,045 | B1 | 9/2001 | Kaufman |
| 6,290,947 | B1 | 9/2001 | Fitzpatrick et al. |
| 6,294,163 | B1 | 9/2001 | Dhal et al. |
| 6,461,646 | B2 * | 10/2002 | Ito .................. A61K 33/38 424/405 |
| 6,468,964 | B1 | 10/2002 | Rowe |
| 2002/0197311 | A1 | 12/2002 | Hasenzahl et al. |
| 2003/0228377 | A1 | 12/2003 | Fanelli |
| 2004/0126427 | A1 | 7/2004 | Venkatesh et al. |
| 2005/0106267 | A1 | 5/2005 | Frykman et al. |

FOREIGN PATENT DOCUMENTS

| | | |
|---|---|---|
| RU | 2016574 | 7/1994 |
| RU | 2063229 | 7/1996 |
| WO | 9011143 | 10/1990 |

OTHER PUBLICATIONS

Lieberman et al., Ed., "Dosage Forms: Disperse Systems", Marcel Dekker, Inc, vol. 2, p. 292 (1996).

Mumpton et al, "The application of natural zeolites in animal science and aquaculture", Journal of Animal Science, 45(5):1188-1203 (1977).

Mumpton, "La roca magica: Uses of natural zeolites in agriculture and industry", Proc. Natl. Acad. Sci., 96:3463-3470 (1999).

National Research council, Washington, D.C., Committee on Food Protection, a Comprehensive survey of industry on the use of food chemicals generally recognized as safe (GRAS), FDABF-GRAS-095, PB221922, Jun. 26, 1973, NTIS, Washington, D.C.

National Research Council, Washington, D.C., Committee on Food Protection, a Comprehensive Survey of Industry on the use of Food Chemicals Generally Recognized as Safe (GRAS), FDABF-GRAS-096, PB221923, Jun. 26, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-097, PB221924, Jun. 26, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-098, PB221925, Jun. 29, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-099, PB221926, Jun. 29, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-100, PB221927, Jun. 30, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-101, PB221928, Apr. 27, 1973, NTISs, Washington, D.C.

National Research Council, Washington, D.C., Committee on Food Protection, a Comprehensive Survey of Industry on the Use of Food Chemicals Generally Recognized as Safe (GRAS), FDABF-GRAS-102, PB221929, Apr. 27, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-103, PB221930, Apr. 27, 1973, NTIS, Washington, D.C.

National Research Council, Committe on Food Protection, a Comprehensive Survey of Industry on the use of food chemicals Generally recognized as safe(GRAS), FDABF-GRAS-094, PB221921, Jun. 26, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-104, PB221931, Apr. 27, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-105, PB221932, May 1, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-106, PB221933, Apr. 28, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-107, PB221934, Apr. 28, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-108, PB221935, Jul. 10, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-109, PB221936, Jan. 30, 1973, NTIS, Washington, D.C.

National Research Council, Washington, D.C., Committee on Food Protection, a Comprehensive Survey of Industry on the Use of Food Chemicals Generally Recognized as Safe (GRAS), FDABF-GRAS-110, PB221937, Jul. 10, 1973, NTIS, Washington, D.C.

(56) References Cited

OTHER PUBLICATIONS

National Research Council, Washington, D.C., Committee on Food Protection, a Comprehensive Survey of Industry on the Use of Food Chemicals Generally Recognized as Safe (GRAS), FDABF-GRAS-111, PB221938, Apr. 28, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-112, PB221939, Feb. 1, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-113, PB221940, Feb. 1, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-114, PB221941, Jun. 6, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-115, PB221942, Feb. 12, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-116, PB221943, Jun. 6, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-117, PB221944, Jun. 25, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-122, PB221945, Jun. 25, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-123, PB221946, Jun. 25, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-124, PB221947, Jun. 25, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-125, PB221948, Jul. 20, 1973, NTIS, Washington, D.C.
National Research Council, Washington, D.C., Committee on Food Protection, a Comprehensive Survey of Industry on the Use of Food Chemicals Generally Recognized as Safe (GRAS), FDABF-GRAS-126, PB221949, Jul. 20, 1973, NTIS, Washington, D.C.
Phillippo et al., "Reduction of radiocaesium absorption by sheep consuming feed contaminated with fallout from Chernobyl", Veterinary Record, 122:560-563 (1988).
Pond et al., "Tissue mineral element content in swine fed Clinoptilolite", Bull. Environ. Contam. Toxicol., 42:735-742 (1989).
Pond, "Zeolites in Animal Nutrition and Health: A Review", Natural Zeolites '93, pp. 449-457 (1995).
Rat Medical Cheat Sheet, http://www.rmca.org/Rescue/ratmedhelp.pdf, pp. 1-2, Accessed: Jan. 28, 2009.
Response to European Office Action for European Patent Application No. 04795567.9, dated Apr. 5, 2016.
Response to European Office Action for European Patent Application No. 04795567.9, dated Sep. 19, 2012.
Shurson et al., "Effects of Zeolite A or Clinoptilolite in Diets of Growing Swine", Journal of Animal Science, 59(6):1536-1545 (1984).
Smith, "Wilson's Disease", pp. 1-4 (2004).
Trisenox(TM) (arsenic trioxide) injection, RX only, 3 pages (revised Mar. 2001).
Zeolites, Abbey Newsletter, vol. 20, No. 7, Dec. 1996.

* cited by examiner

Title: Analysis of the Effect of Particle Size on NH3 Absorption of Sodium Aluminosilicate Date(s) of Study (mm/dd/yyyy): 7/20/2004
Year of MR Manufacture: n/a
MR Bed No.: n/a
FT Lot No.: n/a
Study Operator: Steffens Starting Concentration: 119 p.p.m.
Baseline Concentration: 119 p.p.m.
Loss (Starting-baseline): 0 p.p.m.

Sample #1: 20 p.p.m.
Sample #2: 7 p.p.m.
Sample #3: 6 p.p.m.
Sample #4: p.p.m.
Sample #5: p.p.m.
Sample #6: p.p.m.
Sample #7: p.p.m.
Sample #8: p.p.m.
Sample #9: p.p.m.
Sample #10: p.p.m.

| Sample # ===> | #1 | #2 | #3 | #4 | #5 | #6 | #7 | #8 | #9 | #10 |
|---|---|---|---|---|---|---|---|---|---|---|
| Starting Sample Conc. | 119 | 119 | 119 | | | | | | | |
| Loss | 0 | 0 | 0 | | | | | | | |
| Baseline Conc. | 119 | 119 | 119 | | | | | | | |
| Ending Concentration | 20 | 7 | 6 | | | | | | | |
| NH₃ remaining (%) | 16.8 | 5.9 | 5.0 | | | | | | | |
| NH₃ uptake into DS (%) | 83.2 | 94.1 | 95.0 | | | | | | | |

Notations: Sample #1 is material collected on 170 meash that went through 140 mesh
Sample #2 is material collected on 80 mesh that went through 50 mesh
Sample #3 is material collected on 20 mesh Results: Data suggest that larger particles absorb ammonia better than smaller particles

FIG. 3

ZEOLITE MOLECULAR SIEVES FOR THE REMOVAL OF TOXINS

This application is a Continuation U.S. application Ser. No. 10/965,799, filed Oct. 18, 2004; which claims priority based on U.S. Provisional Application No. 60/512,395, filed Oct. 20, 2003; the entire contents of all of which are incorporated herein by reference in their entirety.

The present invention relates to methods and compositions for treating, preventing, and palliating elevated levels of certain toxins in humans.

Hepatic Encephalopathy Remains a Significant Health Problem

Predominantly because of the large degree of alcohol use in society, chronic liver disease progressing to cirrhosis remains a burdensome health problem. While other toxic liver insults are responsible to a lesser degree, the final common pathway remains the same: progressive hepatic fibrosis and decrease in the proportion of metabolically active hepatocytes. These pathological changes result in systemic health effects related to poor detoxification of endogenously produced ammonia and exogenously administered medications. Because of the cirrhotic liver's markedly reduced ability to neutralize and remove ammonia, a natural waste product from the metabolism of proteins, its blood level rises causing a decreased ability for affected patients to mentate, sense and move normally. This decrease in these functions when attributable to chronic liver disease is known as hepatic encephalopathy.

It is estimated that the economic burden to society related to just the costs of hospitalization for chronic liver disease is over $1 billion annually in the United States. A large portion of these costs is the daily charge for the hospital room; the average stay is approximately 6 days. Thus, if an intervention could be developed that would decrease the average length of hospital stay and/or diminish the need for patients to be hospitalized, patients with chronic liver disease would benefit and the economic burden to society would decrease.

Current standard of care includes the use of supportive care (hydration, vitamins, nutrition administered parenterally, treatment of any gastrointestinal bleeding,) and the drug lactulose, a non-absorbed disaccharide that functions to decrease the rate of absorption of and increase the rate of fecal elimination of ammonia. Lactulose, which is sold as a crystalline powder in a single-dose plastic package, is inconvenient to use in the acute hospital setting because of the need for suspension/dissolution in a sorbitol solution. Moreover, lactulose is only modestly effective and does not appear to have been subjected to randomized controlled trials prior to receiving marketing approval by the US Food and Drug Administration.

Lead Poisoning Remains a Significant Health Problem

Despite advances in the recognition and treatment of clinical and subclinical lead poisoning, a large number of children in the United States are considered lead poisoned. Effective therapy exists for lowering blood lead levels, however the long-term adverse event risk of these treatments limit their use, especially at the lower levels of blood lead.

As taught in a recent government publication (Eliminating Childhood Lead Poisoning: A Federal Strategy Targeting Lead Paint Hazards; President's Task Force on Environmental Health Risks and Safety Risks to Children; Department of Health and Human Services and the Environmental Protection Agency; February, 2000) lead is most hazardous to the nation's 24 million children under six years old of which approximately 4.4% or 1 million have blood lead levels (BLL)>10 $\mu g/dL$. The spectrum and severity of morbidity of lead poisoning increases as blood lead levels increase: reduced IQ, decreased hearing, decreased growth and behavior problems in children can be observed at BLL as low as 10 $\mu g/dL$, impaired nerve function at 20 $\mu g/dL$, reduced vitamin D metabolism at 30 $\mu g/dL$, damage to hematopoiesis at 40 $\mu g/dL$, severe stomach cramps above 50 $\mu g/dL$ and severe brain damage, kidney damage and severe anemia between 50 and 100 $\mu g/dL$. Based on epidemiological models and estimates, a child is estimated to lose 2 IQ (intelligence quotient) points for each 10 $\mu g/dL$ increase in blood lead level.

Current treatments include intravenous chelation therapy with EDTA (ethylenediamine tetraacetic acid) oral chelation therapy with drugs such as succimer, penicillamine and British anti-Lewisite (BAL). Chelation therapy with EDTA is indicated for severe lead poisoning and must be administered—either three times daily or as a continuous infusion—in combination with succimer. Succimer, an oral drug, is administered on a subchronic basis and is not indicated for BLL<20 $\mu g/dL$. Penicillamine may also be used, but is known for a particularly troublesome side effect profile, which limits its chronic use. Additional details are found below.

EDTA (edetate, versenate; CAS [62-33-9]) remains difficult to administer despite its demonstrable lead-chelating activity. It remains a component of standard of care for severe cases of lead poisoning where rapid decrease in the BLL is desired and requires hospitalization. Key pharmacological properties of EDTA include only intravenous administration and half-life of 20 to 60 minutes. Rapid clearance results in only one-half the drug remaining one hour following administration and only 5% of the administered dose remains after 24 hours. The dose must be adjusted for decreased renal clearance. Substantial monitoring is required for cardiac changes, renal function and serum electrolyte changes resulting in daily phlebotomy and attachment to a cardiac monitor. These precautions are recommended because of potential decreases in serum zinc, copper and iron, which are also chelated by EDTA. Because EDTA may only be administered parenterally, local pain and swelling are a risk. Systemic adverse events include fever, chills, malaise, nausea, vomiting, anorexia, myalgias, arthralgias and a histamine-like reaction. Nephrotoxicity can manifest as acute tubular necrosis, microscopic hematuria, proteinuria and elevated blood urea nitrogen and serum creatinine. The liver may be affected as evidenced by transient mild elevations of the transaminases and the bone marrow may also be affected as evidenced by the findings of anemia and thrombocytopenia.

Succimer (CHEMET, dimercaptosuccinic acid, DMSA; CAS [304-55-2]) is a white crystalline powder with an unpleasant odor and taste characteristic of mercaptans. It is administered orally in divided doses based on the size of the patient thereby making administration easier and not requiring hospitalization. It is indicated for blood lead levels>45 $\mu g/dL$ and is expressly not indicated for prophylaxis against lead poisoning in a lead laden environment. It is effective in reducing the blood lead level, although several features limit and complicate its use. It is recommended to administer succimer every 8 hours for the first 5 days followed by twice daily for the next 14 days. A waiting period is recommended before a second 19-day cycle should begin. Weekly monitoring of the blood counts is recommended for proper management of the drug-induced neutropenia. If the absolute neutrophil count decreases below 1200/$\mu L$, succimer administration should stop until recovery to >1500/$\mu L$.

Drug-induced elevations of liver transaminases, which are mild and transient and seen in up to 10% of patient, should be monitored for weekly. A particular toxicity in the form of recurrent mucocutaneous eruptions has been described and requires cessation of therapy. Systemic adverse events known with succimer administration include nausea, vomiting, diarrhea, anorexia, loose stools, metallic taste and occur singly or in combination in up to 12% of children and 21% of adults. In addition, back pain, abdominal cramps, chills and flu-like symptoms have been reported in 5% of children and 16% of adults. Succimer is known to interact with various laboratory tests resulting in incorrect values of urine ketones, uric acid and creatine phosphokinase activity.

Penicillamine (Cuprimine, D-Pen, beta,beta-dimethylcysteine, 3-mercaptovaline; CAS [52-67-5]) is a chelating agent, which has found utility in treating Wilson's disease, cystinuria and rheumatoid arthritis. It is a white, crystalline powder, which is freely soluble in water. Penicillamine is known to interfere with normal tropocollagen cross-linking resulting in newly formed collagen fibrils, which are cleaved. To achieve maximum bioavailability and avoid chelation of metals within ingested foods or vitamins, it is recommended that penicillamine be taken on an empty stomach 1 hour before or 2 hours after meals. Penicillamine is associated with a number of untoward reactions, which are potentially fatal. Serious blood dyscrasias including fatal aplastic anemia and fatal agranulocytosis have been observed during chronic treatment and close monitoring of white blood count, white cell differential and hemoglobin are strongly recommended by the manufacturer. Thrombocytopenia and eosinophilia are other hematological effects observed. Routine analysis of the urine is recommended to detect the insidious onset of proteinuria and microscopic hematuria, which may be associated with the Goodpasture's syndrome. Other adverse effects include several of the described subtypes of pemphigus (especially pemphigus foliaceous), increased skin friability at pressure points and sites of trauma, lupus-like syndrome (not associated with hypcomplementemia) with elevated anti-nuclear antibody (ANA) titer, aphthous ulceration of the oral mucous membranes, myasthenia gravis and hypoguesia, or blunting of the sense of taste. The manufacturer recommends close observation and frequent follow-up of any patient receiving penicillamine.

Dimercaprol (BAL, British anti-lewisite, 2,3-dimercapto-1-propanol; CAS [59-52-9]) is a clear, colorless, viscous oily fluid with a pungent odor typical of mercaptans. It is dissolved in and administered, intramuscularly, in peanut oil. Its mechanism of action appears to be complexation with and oxidation by heavy metal ions including lead, copper and arsenic. The dose administered is based on achieving a 2:1 molar ratio of dimercaprol to the heavy metal and it may be used in combination with EDTA. The half-life is short such that following intramuscular administration, dimercaprol is essentially all renally excreted within 4 hours. There are a number of pronounced and dose-related side effects which the amount or dimercaprol that may be administered. Approximately 50% of patients administered the 5 mg/kg dose will experience one of several adverse events. Amongst the most common of the side effects is a rise in systolic and diastolic blood pressure by up to 50 mmHg. Nausea is commonly reported and to a lesser degree vomiting. Headache is reported less commonly than nausea although further details about the headache are not described in the references cited. A burning sensation in the lips, mouth and throat accompanied with the feeling of constriction is well known. Conjunctivitis, blepharospasm, lacrimation, rhinorrhea and increased salivation are also known to be associated with dimercaprol use. Other less common side effects include tingling of the feet and hands, abdominal pain, sweating of the forehead and hands and painful, sterile abscesses at the injection sites. Dimercaprol is known to cause hemolysis in patients with glucose-6-phosphate dehydrogenase deficiency and a transient decrease in the percentage of polymorphonuclear leukocytes has been observed. The manufacturer recommends that the urine be alkalinized to maintain the integrity of the metal-drug complex during transport through the renal tubule.

Although each of these interventions is effective at reducing the apparent blood level, following such therapy, it is well known that there is a rebound in the BLL, which arises from unchelated tissue stores such as the bone and soft tissues. There is at present no FDA-approved treatment for reducing the tissue stores of lead.

Wilson's Disease Contributes to the Burden of Heavy Metal Poisoning

Wilson's disease is a less common inborn error of copper metabolism in which the endogenous copper carrier protein, ceruloplasmin is decreased or absent. The result is elevated levels of tissue copper, which is responsible for the diseases neurological and hepatic complications. Effective therapy exists; however, it is associated with moderate to severe adverse effects that, in turn, limits its use.

One additional treatment for Wilson's disease is the use of zinc acetate (Galzin). It acts on the intestinal epithelium to prevent the absorption of copper from dietary sources, which is believed due to the zinc ion by increasing the production of metallothionein in the enterocyte. Zinc acetate is administered orally in the form of gelatin capsules though it should be separated from food and beverages by at least one hour, preferably on an empty stomach. Twenty-five to 50 mg should be taken three times per day in adults and strict adherence to the zinc regimen is essential for optimal control of copper distribution. Zinc acetate is indicated for the maintenance of patients with Wilson's disease who have been initially treated with a chelating agent and is specifically not recommended for the initial therapy of symptomatic patients because of the delay required for zinc-induced increase in enterocytic metallothionein and blockade of copper uptake. Source: Galzin (zinc acetate) package insert.

As taught by Scheinberg (Scheinberg I H "Wilson's Disease" in Harrison's Principles of Internal Medicine, $12^{th}$ ed., Wilson J D, et al., eds, pp. 1843-1845) the prevalence of Wilson's disease is approximately 1/30,000 or approximately 8700 individuals in the US with this disease. Clinical manifestations of copper excess are rare before age 6 and half of untreated patients remain asymptomatic through adolescence. Liver manifestations of Wilson's disease may include acute hepatitis, fulminant hepatitis, chronic active hepatitis or cirrhosis. The only manifestation may be cirrhosis, which develops insidiously over decades. Neurological or psychiatric disturbances may be the initial presenting manifestation.

The drug of choice is penicillamine and should be started upon confirmation of the diagnosis and is administered in divided doses in conjunction with pyridoxine. Additional information about the toxicity of penicillamine may be found above. It usually appears in the first 2 weeks and may cause a rash, fever, leukopenia, thrombocytopenia, lymphadenopathy and/or proteinuria. Penicillamine must be discontinued if these adverse events supervene. Readministration with prednisone can be successful. Lifelong and continual treatment is required and non-compliance can be fatal. Successful treatment suggests that continued copper-lowering therapy could prevent virtually every manifestation of Wilson's disease. Second-line therapy such as trientine is available for patients unable to tolerate penicillamine.

Trientine hydrochloride (Syprine Capsules, bisaminomethylethanediamine dihydrochloride; CAS [112-24-3]) is a white to pale yellow crystalline powder, which is freely soluble in water. The mechanism appears to be increase cupriuresis though on a molar basis appears to be less effective than penicillamine. Trientine should be administered on an empty stomach at least one hour from ingestion of other drugs, food or milk. There have been reports of asthma, bronchitis and dermatitis following environmental exposure to inhaled trientine. In addition, systemic lupus erythematosus, dystonia muscular spasm and myasthenia gravis have been reported in conjunction with trientine use. Other effects noted in four patients with biliary cirrhosis included heartburn, epigastric pain, thickening, fissuring and flaking of the skin, hypochromic microcytic anemia, acute gastritis, aphthous ulcers, myalgias, weakness and rhabdomyolysis.

Arsenic Exposure and Arsenic Poisoning is Becoming More Frequently Diagnosed

Arsenic has recently become more widely discussed in the public media in terms of its exposure through drinking water. Although EPA limits for municipal water supplies exist, some feel this level to be excessive. It appears that the federal government will reduce the current 50 ppb (parts per billion) limit to 10 ppb. In some defined geographic areas, extremely high levels of arsenic are found in certain wells. Chronic exposure to arsenic at elevated levels has been associated with skin diseases and skin cancer. At present, there are no FDA-approved treatments for chronic arsenic exposure.

The health effects of arsenic are well known from several sources: epidemiological studies, accidental exposures, animal toxicological studies and occupational and therapeutic exposures. There are also a number of factors that must be considered when the toxicity spectrum and severity are reported. These include the form of the arsenic introduced in vivo (inorganic vs. organic, valence, the salt form, the specific organic moiety), the route of exposure (inhalational, transdermal, enteral or parenteral), the rate at which the exposure took place (minutes, hours, days, weeks, years or decades) and the degree of prior exposure to arsenic.

Adverse health effects of arsenic are legion and are dependent on many of the factors listed above. Severe hemolysis followed by renal failure and death may complicate acute inhalational exposure to arsine gas ($AsH_3$). Hemorrhagic gastritis and gastroenteritis accompanied by nausea, vomiting, diarrhea, convulsions and eventually death from circulatory collapse may occur within 12 to 24 hours of oral ingestion of arsenic trioxide ($As_2O_3$) in the range of 1 to 3 mg/kg. There are also a number of neurologic signs and symptoms that may be associated with oral arsenic trioxide exposure at the same level including encephalopathy, headache, lethargy, confusion, hallucination, seizure and coma. Additional findings may include muscular cramps, facial edema, cytopenias, renal insufficiency, pulmonary edema and hemorrhagic bronchitis. Electrocardiographic abnormalities such as a prolonged QTc interval and T wave changes have been described.

Chronic exposure may occur by the inhalational, oral, or dermal routes. Numerous organ systems are affected causing a wide array of clinical signs and symptoms. Long term exposure may affect small blood vessels, which can manifest in several different ways including Raynaud's phenomenon, acrocyanosis of the toes leading to gangrene and Blackfoot disease requiring amputation. Post-mortem examination of children with cutaneous signs suggesting arsenic exposure revealed marked thickening of small- and medium-sized arteries specifically in the coronary, cerebral and mesenteric arteries resulting in myocardial infarction in 2 or 5 cases. Neurological signs and symptoms are known to accompany survivors of poisoning attempts including peripheral neuropathy and encephalopathy. The peripheral neuropathy begins as paresthesias, hyperesthesias and neuralgias that may later develop into frank pain and muscle weakness. Histopathological evidence of Wallerian degeneration exists, especially in the long-axon neurons. The findings tend to be bilaterally symmetrical. Recovery is slow and often incomplete. On clinical and electromyographic grounds, the diagnosis of arsenic-induced polyneuropathy may be confused with Guillain-Barre syndrome. Workers from copper smelters have noted a variety of upper respiratory signs and symptoms—presumably from chronic inhalation of arsenic-laden vapors and dusts—including rhinitis, laryngitis and bronchitis. Extreme cases have resulted in perforation of the nasal septum. Exposure in this same context may results in a spectrum of gastrointestinal findings including nausea, vomiting, and diarrhea. Oral exposure may include the same findings in addition to abdominal pain. Hepatic injury is also known to correlate with chronic oral arsenic exposure including swollen and tender livers, elevations of hepatic enzymes, and may reveal portal fibrosis under histopathological examination. Renal effects of arsenic are also known and include proteinuria, elevated creatinine, hematuria, pyuria and glycosuria in patients with sublethal oral exposure.

Although the specific mechanism has been convincingly described, several putative mechanisms have been proposed for the finding of arsenic-induced anemia, leukopenia and the myelodysplastic syndrome. Arsenic may be goiterogenic and diabetogenic. Skin effects of arsenic are well known and include both benign and malignant conditions including hyperpigmentation interspersed with small areas of hypopigmentation (the so-called "raindrop"-like appearance) distributed on the neck, chest and back; palmar-plantar hyperkeratosis with the characteristic small corn-like elevations observed in subjects exposed to arsenic through drinking water. Continued exposure may result in ulcerative lesions after several decades. Basal cell carcinoma, epidermoid carcinomas, intraepidermal carcinomas and Bowen's disease associated with arsenic exposure are well described in the medical and epidemiological literature. Cancers of other organs have been reported to be found in patients living in near proximity to copper smelters including kidney and bladder, in patients having received Fowler's solution (potassium arsenate) including lung cancer and in patients exposed to high arsenic levels in their drinking water in Taiwan including bladder, kidney, liver, lung and colon cancer.

SUMMARY

The invention relates to a method of for treating, preventing, and palliating elevated human blood lead levels, comprising administering to a human in need thereof a pharmaceutical formulation comprising a synthetic sodium aluminosilicate and a pharmaceutically acceptable adjuvant, wherein: (a) the synthetic sodium aluminosilicate is particulate and at least 90% of the particles are of particle size from about 90 μm to about 150 μm; (b) the formulation is administered in doses of about 10 mg to about 1000 mg sodium aluminosilicate.

The invention also relates to a method of treating, preventing, and palliating elevated human blood ammonia levels, comprising administering to a human in need thereof a pharmaceutical formulation comprising a synthetic sodium aluminosilicate and a pharmaceutically acceptable adjuvant, wherein: (a) the synthetic sodium aluminosilicate is particulate and at least 90% of the particles are of particle size from about 90 μm to about 150 μm; (b) the formulation is from about 50% (w/w) to about 95% (w/w) water; and (c) the formulation is administered in doses of 2 g to 15 g sodium aluminosilicate.

The invention also relates to a method including administering to a human in need thereof a pharmaceutical formulation comprising a synthetic sodium aluminosilicate and a pharmaceutically acceptable adjuvant, wherein: (a) the synthetic sodium aluminosilicate is particulate and at least 95% of the particles are of particle size from about 90 μm to about 150 μm; (b) the formulation is administered in doses of about 5 g to about 12 g sodium aluminosilicate; and (c) the human has a higher than normal risk of elevated blood levels of a toxic metal or has a higher than normal risk of hepatic encephalopathy.

The invention relates to a pharmaceutical formulation, comprising: (a) a particulate synthetic sodium aluminosilicate wherein at least 90% of the particles are of particle size from about 90 μm to about 150 μm, (b) about 50% to about 80% by weight water; and (b) a microbial preservative; and (c) a pharmaceutically acceptable adjuvant; wherein the formulation contains about 100 mg to about 10,000 mg by weight of sodium aluminosilicate.

The invention also relates to methods and formulations identical to those described above, but targeting elevated levels of other toxins, in particular copper or arsenic. Thus the invention relates to treatment, prevention, and palliation in humans or animals of excess levels of lead, ammonia, copper, and arsenic, as well as other toxins.

BRIEF DESCRIPTION OF THE DRAWINGS

FIG. 3 is an analysis of the effect of zeolite particle size on ammonium absorption.

DETAILED DESCRIPTION

Figure 1:
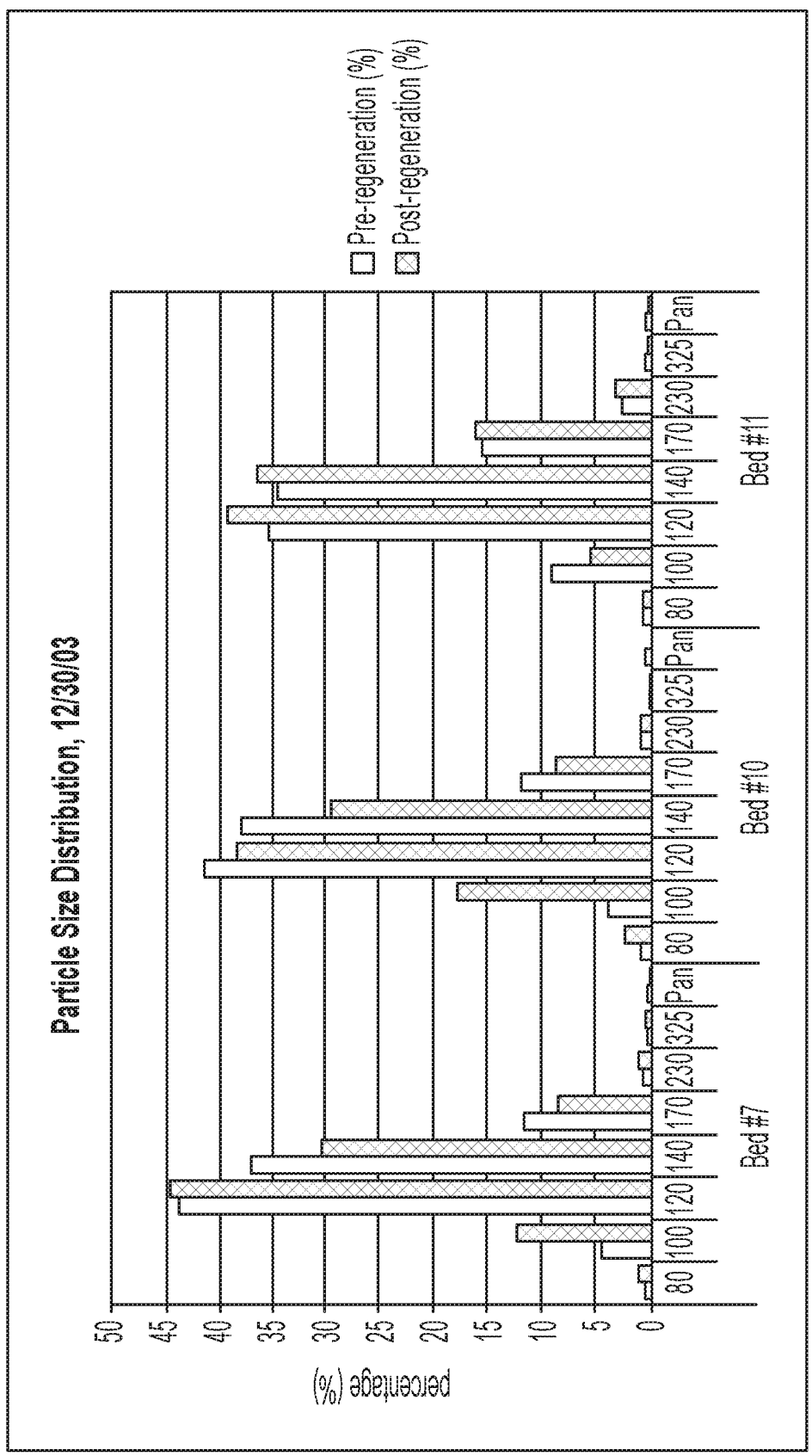
FIG. 1 is a chart showing particle size distribution for a zeolite.

This invention relates specifically to a microporous or mesoporous silicate, also known as a molecular sieve, which is granular or powdered and which is administered orally, topically or rectally to humans once, daily for several days, weeks, months or years, or more than once daily for days to years for the purpose of treating human diseases. The zeolitic substance is administered in the form or a tablet, capsule or pharmaceutical suspension.

Synthetic zeolites are preferred. As used herein, "synthetic zeolite" means a zeolite manufactured or synthesized by one or more chemical reactions involving breaking and/or making chemical bonds. "(w/w)" means percent by weight, as calculated based on the weight of the component and the total weight of the composition or formulation. Generally, the terms used in this application are well known to persons of skill in the art.

The granules or powder particles are small enough that diffusion of a variety of ions or other organic or inorganic toxins may freely pass in and through the rigid and well-ordered crystalline structure. It is understood that water may or may not comprise the zeolitic material initially, but in an aqueous environment such as the human digestive tract, water will virtually completely fill the framework structure. Based on the specific details of the framework structure, it has been shown that there is a specificity of binding of ions, toxins and other classes of molecules.

In one embodiment, a gelatin capsule of the zeolite is swallowed by a person with a glass of water. In the acidic environment of the stomach, the gelatin capsule dissolve thereby releasing several hundred milligrams of the zeolite. The zeolite absorbs water to full saturation and forms a slurry. Aluminosilicates are known to be resistant to acidic degradation at room temperature or body temperatures and therefore the framework structure remains intact during passage through the stomach and is not susceptible to the actions of oral cavity-, stomach- or pancreas-, small bowel- and large-bowel-derived digestive enzymes and peristaltic movements. In the intestinal juices found in the stomach, duodenum, jejunum, ileum and colon poisonous ions and toxins will bind to the zeolite. These poisons or toxins include heavy metals such as lead, copper, potassium, ammonia, mercaptans and hydrogen sulfide. Additional toxins include those that are plant-, marine organism- and nuclear-derived. When a poisonous ion or molecule binds to the zeolite, it is prevented from exerting its toxic effects on the intestinal lining or from being absorbed into the bloodstream for systemic deposition. An important feature is that zeolites administered as described may be employed to remove toxic ions or molecules over the period of administration of hours, days, weeks, months or years. The purpose of the zeolite is not only intended to prevent the deposition of toxic effects of a heavy metal or toxin that may be a contaminant of ingested food, but additionally it is envisioned to be used in the emergency treatment of toxic ingestions, radioactive fallout (strontium and cesium), toxic marine organism ingestions, poisoned food ingestions, etc. The zeolite, which binds the adsorbed toxic ions or poisonous substances while coursing through the gastrointestinal tract, is eliminated from the body in the feces. An important consideration is having the correct surface area to weight ratio for optimal absorption and minimal toxicity. If the zeolite is powdered too finely, it could accumulate in undesirable anatomical locations such as the appendix or a divertuculum, resulting in a pathologic condition. If the zeolite is too large, the absorptive capacity as a function of weight decreases significantly and substantially larger amounts of the zeolite must be ingested to achieve the same amount of absorption.

The particle size distributions cited in this patent are derived from a technique known as analytical sieving. A full description may be found in the *United States Pharmacopeia*, $24^{th}$ edition (USP 24/NF 19) physical test number <786> as described on pp. 1969-1970, Method 1, which was followed to determine the particle size distribution of the CR-100 sodium aluminosilicate. The following table is illustrative.

TABLE 1

| Sieve Size (μm) | U.S. Sieve No. | ASTM E-11* | Recommended USP Sieves** |
|---|---|---|---|
| 4000 | 5 | X | X |
| 3350 | 6 | X | |
| 2800 | 7 | X | X |
| 2360 | 8 | X | |

TABLE 1-continued

| Sieve Size (μm) | U.S. Sieve No. | ASTM E-11* | Recommended USP Sieves** |
|---|---|---|---|
| 2000 | 10 | X | X |
| 1700 | 12 | X | |
| 1400 | 14 | X | X |
| 1180 | 16 | X | |
| 1000 | 18 | X | X |
| 850 | 20 | X | |
| 710 | 25 | X | X |
| 600 | 30 | X | |
| 500 | 35 | X | X |
| 425 | 40 | X | |
| 355 | 45 | X | X |
| 300 | 50 | X | |
| 250 | 60 | X | X |
| 212 | 70 | X | |
| 180 | 80 | X | X |
| 150 | 100 | X | |
| 125 | 120 | X | X |
| 106 | 140 | X | |
| 90 | 170 | X | X |
| 75 | 200 | X | |
| 63 | 230 | X | X |
| 53 | 270 | X | |
| 45 | 325 | X | X |

Source: *United States Pharmacopeia*, 24<sup>th</sup> edition (USP 24/NF 19), United States Pharmacopeial Convention, Inc., Rockville, MD; Method <786>, pp. 1969-1970.
*American Society for Testing and Materials (ASTM) Specification E-11, U.S. Standard Sieve Series. Additional information may be found to ASTM procedure STP 447, "A Manual on Test Sieving Methods," available from the ASTM, 100 Bar Harbor Drive, West Conshohocken, PA 19428-2959
**The equivalent ISO Standard sieves may be substituted.

The present invention relates to the use of zeolite molecular sieves to bind, sequester and eliminate heavy metals, potassium, ammonia and mercaptans, plant-, marine organism- and fungus/mushroom-derived toxins, radioactive fallout contaminants and hydrogen sulfide and hydrogen sulfide-related, endogenously produced chemicals from a human that may be the source of toxic effects.

For treating, preventing, and palliating high blood lead levels, preferably at least 95% of the particles are of particle size from 90 μm to 150 μm. The formulation may include from about 60% to about 95% by weight water. Preferably, the formulation is a capsule or tablet administered orally. The treatment is suitable for a human suffering from chronic lead poisoning. The human may have a blood lead level of at least about 10 μg/dL, at least about 20 μg/dL, at least about 30 μg/dL, at least about 40 μg/dL, or even of at least about 50 μg/dL. The human may be between about 2 and about 15 years of age, or may be under about 6 years of age. Dosages may be, e.g., about 10 mg to about 1000 mg sodium aluminosilicate, or about 100 mg to about 900 mg, or about 200 mg to about 800 mg. Preferably, the formulation further comprises an antimicrobial preservative or bacteriostat.

The present invention is preferably directed to patients with blood lead levels of <10.0 μg/dL, 10.0-14.9 μg/dL, 15.0-19.9 μg/dL, 20.0-44.9 μg/dL, 45.0-59.9 μg/dL, or >60.0 μg/dL, in each case in combination with one or more therapies recommended for use in the range by state or federal programs, as exemplified in the State of Minnesota Department of Health's Childhood Blood Lead Clinical Treatment Guidelines, March 2001.

For treating preventing, and palliating high human blood ammonia levels, preferably at least 95% of the particles are of particle size from 90 μm to 150 μm. The human may be suffering from hepatic encephalopathy or cirrhosis of the liver. The human may have a history of liver failure. Preferably the formulation is a liquid gel administered orally. The human may have an elevated blood ammonia level or may be at risk for such an elevated level. The human may be a hospital in-patient.

While certain particle size ranges are preferred, this is not meant to limit the scope of the invention. For example, in certain circumstances very fine particles of <44 μm may be preferred.

The term "elevated" blood lead level means a level of lead in the blood that is above normal, where normal is the specified laboratory's normal range as determined on blood from non-diseased, healthy volunteers in the local area, using the local technique-of-choice for the laboratory performing the assay (which could include conventional atomic absorption spectroscopy, graphite furnace atomic absorption spectroscopy, and anodic stripping voltammetry) and processed according to the laboratory's procedure precisely specifying the type of collection container to use, specifying whether it should be placed immediately on ice, the timeframe in which it is to be delivered to the laboratory, and the use of a specified preservative, if any. A term frequently employed for the upper end of the normal range is the institutional upper limit of normal (IULN), and is intended to have the same meaning as normal for use in this patent. (Lewandrowski, pp. 820-821.)

By "hyerammonemia" or other terms used to indicate higher than normal levels of ammonia is meant higher levels than normal, where normal is the specified laboratory's normal range as determined on blood from non-diseased, healthy volunteers in the local area, using the local technique-of-choice for that laboratory that performed the assay (which could be venous blood, arterial blood, or some fraction of whole blood including plasma or serum) and processed according to the laboratory's procedure specifying whether it should be placed immediately on ice, the timeframe in which it is to be delivered to the laboratory, using the specified preservative, if any. A term frequently employed for the upper end of the normal range is the institutional upper limit of normal (IULN), and is intended to have the same meaning as normal for use in this patent. (Lewandrowski, pp. 733-735.)

These definitions avoid the controversial nature of clinical laboratory assay performance which remains unsettled for many reasons including that assay principles vary; assay sites differ (hospital laboratory versus point-of-care versus physician office laboratory versus home testing); specific reagents vary including proprietary reagents for commercially available assays; arterial or venous blood may offer advantages or be specified by method; whole blood versus specific fraction such as plasma, serum or erythrocyte; specific collection container that has been processed in a specified manner; requirements exist for the specific assay for preservatives, special handling, temperature, and others; analytical instrument on which assay is performed may vary; varying normal ranges for assay depending on geographical location; evolution of actual assay method based on the same principle. Source: Lewandrowski K., ed. Clinical Chemistry: Laboratory Management and Clinical Correlations, Lippincott Williams & Wilkins, 2002.

For treating, preventing, and palliating high human blood levels of copper or arsenic, the same methods and formulations may be used. Thus the invention relates to treatment, prevention, and palliation in humans or animals of excess levels of lead, ammonia, copper, and arsenic, as well as other toxins.

"Prevention" means actions, which usually emanate from the workers within the health sector that deals with individuals and populations identified as exhibiting identifiable risk factors for disease that may often be associated with different risk behaviors. Prevention also refers to measures not only to mitigate against the occurrence of disease, such as risk factor reduction, but also to arrest its progress and reduce its consequences once established. The use of the term prevention in this patent includes the following: primary prevention (which are actions directed towards preventing the initial occurrence of a disorder); secondary prevention (which are actions that seek to arrest or retard existing disease and its effects through early detection and appropriate treatment); and tertiary prevention (which are actions intended to reduce the occurrence of relapses and the establishment of chronic conditions through, for example, effective rehabilitation).

"Palliation" means any form of medical care or treatment that concentrates on reducing the severity of the symptoms of a disease or slows its progress rather than providing a cure. It aims at improving quality of life, and particularly at reducing or eliminating pain. The definition specifically focuses on the general unavailability of a cure in that it emphasizes the active total care of patients whose disease is not responsive to curative treatment. However, in some cases, palliation may involve alleviation of the side effects of curative treatments, such as relieving the nausea associated with chemotherapy. The term palliation is not intended for use in this patent to refer to a chronic disease, such as diabetes which, although technically incurable, has available treatments that are (ideally) effective enough that it is not considered a progressive or life-threatening disease in the same sense as resistant or refractory cancer.

"Treatment" refers to the coordinated healthcare interventions and communications for individuals and populations with disease conditions in which patient self-care efforts are significant. The definition of treatment in this patent additionally refers to the identification of one or more disease processes, use or modified use of evidence-based practice guidelines (when they exist), collaboration of physicians and supportive-service providers, patient self-management education, outcome measurement, and communication with the patient and other relevant providers about the outcome of the disease stemming from the interventions applied.

The present invention may also be used for the treatment of arsenic toxicity derived from arsenic trioxide therapy use in the treatment of acute promyelocytic leukemia (APL). Although arsenic trioxide has been demonstrated to be effective in the treatment of relapsed APL (one form of acute myelogenous leukemia), cardiac conduction side effects occur which appear to be related to the cumulative dose of arsenic administered and are exacerbated by other electrolyte abnormalities, such as hypokalemia and hypomagnesemia. If the electrolyte abnormalities are corrected and the patient continues to experienced a prolonged QTc (corrected QT) interval or abnormal heart rhythms or associated rapid and irregular heartbeats develop, the manufacturer recommended that the drug be temporarily discontinued until the QTc interval regresses to <460 milliseconds. Source: Trisenox (arsenic trioxide) package insert, March 2001 revision. Because of sodium aluminosilicates' ability to selective bind metal and metalloid ions, such zeolites assist in the treatment of arsenic toxicity in the treatment of APL. The present invention provides a formulation comprising a synthetic aluminosilicate and arsenic trioxide with a pharmaceutically acceptable adjuvant, and a method for treating APL by administering a synthetic aluminosilicate together with arsenic trioxide whether formulated together or separately. In this setting, both acute and subacute treatment with 1-10 grams orally administered once to multiple times per day is envisioned. However, chronic therapy in the range of 100-1000 milligrams once to several times per day is possible.

Recently, arsenic trioxide, administered intravenously, has become the FDA-approved standard of care for relapsed acute promyelocytic leukemia (APL) following therapy with all trans retinoic acid. Following conventional antineoplastic pharmaceutical development, it is likely that arsenic trioxide use will become more common and be used earlier in the management of APL. Patients may achieve a complete remission of their disease, leaving them susceptible to the health effects described above. At present, there is no described antidote for these effects beyond careful monitoring and cessation of the therapy when complications outweigh the benefit from continued treatment.

Potassium regenerated sodium aluminosilicate is an alternative for treatment of hepatic encephalopathy. An important principle in the clinical management of hepatic encephalopathy is treatment of the precipitating or underlying cause of the encephalopathic episode. That is, while a patient may have the established diagnosis of liver failure, only when his or her mental capacity declines is the diagnosis of HE firmly established. However, often other dietary, pharmacological, electrolyte or infectious influences alter the balance between normal mentation and encephalopathy. Many times, however, the exacerbating factor is not determined. While the treatment of HE remains similar to that described elsewhere in this specification, specific attention to the precipitating factor (such as a large dietary load of protein, underlying infection, unexpected reaction from an ingested drug or overuse of certain drugs leading to urinary loss of potassium) is warranted by the treating physician. Because the use of the potassium-depleting drugs (namely spironolactone and members of the same and different classes) is common in patients with liver failure, they can lead to total body loss of potassium and thereby precipitate an encephalopathic episode. The potassium form of sodium aluminosilicate may be used instead of the sodium form to treat patients with hepatic encephalopathy. In the manufacturing process, potassium may be exchanged for sodium in the regeneration process.

The synthetic aluminosilicate is preferably charged with sodium. Alternatively, the synthetic aluminosilicate may be charged with another alkali metal, e.g., Li, K, or Rb. The synthetic aluminosilicate may alternatively be charged with an alkali earth metals, e.g., Ca or Mg. The synthetic aluminosilicate may be chemically modified by methods including pegylation, silation, and glycosylation. The formulation may contain different particle size distributions of the zeolite of interest, and may comprise mixtures of one or more synthetic zeolites. The formulation may contain varying amounts of water, e.g., from about 40% or 50% (w/w) up to about 70%, 80%, or 95% (w/w).

The present invention may be used in diagnostic procedures, e.g., to determine the degree of metal poisoning, as a carrier for x-ray contrast agents, gadolinium based magnetic resonance imaging contrast agents and positron-emitting metabolites for use in positron emission tomography. The present invention may also be used to control diarrhea, especially in conjunction with lactulose in the treatment of hepatic encephalopathy. The present invention may be used in the prevention, treatment, and palliation of Alzheimer's disease, specifically through the binding of gut-derived ammonia and preventing its uptake into the systemic circulation and conferring its toxicity on the central nervous system over the course of many years.

A formulation containing the zeolite may also contain an antimicrobial preservative. The following Table lists examples of antimicrobial preservatives suitable for formulations of zeolites intended for oral, gastric, enteral or rectal administration.

TABLE 2

| Antimicrobial Preservative | Further Specification | Reference |
| --- | --- | --- |
| benzalkonium chloride | | pp. 27-29 |
| benzoic acid | | pp. 32-34 |
| benzyl alcohol | | pp. 35-37 |
| bronopol | | pp. 40-42 |
| butylparaben | | pp. 49-51 |
| chlorhexidine | as various salts | pp. 106-110 |
| chlorobutanol | | pp. 111-113 |
| chlorocresol | | pp. 114-116 |
| cresol | includes ortho-, meta- and para- isomers | pp. 139-140 |
| ethanol | | pp. 7-9 |
| ethylparaben | | pp. 191-193 |
| imidurea | includes monohydrate | pp. 238-239 |
| methylparaben | | pp. 310-313 |
| phenol | | pp. 336-337 |
| propionic acid | as various salts | pp. 459-461 |
| propylparaben | | pp. 411-414 |
| sodium benzoate | | pp. 433-435 |
| sorbic acid | | pp. 470-472 |
| triacetin | | pp. 534-535 |

Source: Wade A and Weller P J. *Handbook of Pharmaceutical Excipients*, 2d ed., American Pharmaceutical Association, Washington, DC; 1994

The table below exemplifies microorganisms that require reduction or eradication in a zeolite formulation intended for oral, gastric, enteral or rectal administration. These include bacteria and fungi which are known to be more or less commonly pathogenic and are found in patients suffering from infections. It is therefore desirable to render the zeolite and associated pharmaceutical adjuvants sterile or with an acceptable low microorganism dose such that patients are not harmed. The list includes bacteria (gram positive, gram negative, anaerobic, aerobic, and others), fungi and spores in applicable species.

TABLE 3

| Microorganisms |
| --- |
| *Aeromonas aeorgenes* |
| *Aspergillus niger* |
| *Aspergillus oryzae* |
| *Bacillus cereus* |
| *Bacillus subtilis* |
| *Candida albicans* |
| *Clostridium histolyticum* |
| *Clostridium oedematiens* |
| *Clostridum sporogenes* |
| *Clostridium tetanii* |
| *Clostridium welchii* |
| *Coynebacterium* species |
| *Enterobacter cloacae* |
| *Escherechia coli* |
| *Klebsiella pneumoniae* |
| *Microsporum* species |
| *Penicillium chrysogenum* |
| *Penicillium digitatum* |
| *Penicillium notatum* |
| *Penicullium roqueforti* |
| *Pityrosporum ovale* |
| *Proteus mirabilis* |
| *Proteus vulgaris* |
| *Pseudomonas aeruginosa* |
| *Pseudomonas cepacia* |
| *Pseudomonas fluorescens* |
| *Pseudomonas stutzeri* |
| *Rhizopus nigricans* |
| *Saccharomyces cerevisiae* |
| *Salmonella enteritidis* |

TABLE 3-continued

| Microorganisms |
| --- |
| *Salmonella gallinarum* |
| *Salmonella paratyphi* |
| *Salmonella typhosa* |
| *Sarcina lutea* |
| *Serratia marcescens* |
| *Shigella dysenteriae* |
| *Staphylococcus aureus* |
| *Staphylococcus epidermidis* |
| *Streptococcus faecalis* |
| *Streptococcus pyrogenes* |
| *Trichoderma lignorum* |
| *Trichoderma mentagrophytes* |
| *Trichophyton mentagrophytes* |
| *Vibrio cholerae* |

Zeolites Offer an Unexploited Family of Substances to Remedy Hepatic Encephalopathy and Heavy Metal Poisoning Nagan (U.S. Pat. No. 6,190,561) discloses a method of water treatment using zeolite crystalloid coagulants which is prepared by admixing aqueous sodium silicate and sodium aluminate solutions to form a reaction mixture and allowing a reaction to proceed for a sufficient time to form a zeolite crystalloid coagulant particles with sizes of at least 4 nanometers before the reaction is terminated. Demmel and Vierheilig (U.S. Pat. No. 6,103,949) disclose a family of alkaline phosphate-activated clay/zeolite catalysts, which can be prepared by a process wherein a composition of zeolite-clay-phosphate is brought to a pH level of about 7.0 to about 14.0. The resulting slurry is then age reacted for ½ to 24 hours and finally dried to produce particles that are particularly characterized by their high levels of zeolite stability for utilization in the catalytic cracking of petroleum-based materials. Levy (U.S. Pat. No. 5,612,522) describes the use of a zeolite gel to improve the quality and carbonation of water by the removal of dissolved gases and minerals. Features not disclosed in these patents include any application to the removal of heavy metals, ammonia, mercaptans and other plant-, marine organism- and nuclear-derived toxins and no use in humans or animals is discussed.

As taught by Adams, et al. (U.S. Pat. No. 5,560,829), aluminosilicates of the zeolite P type may be used as calcium binders in aqueous solutions at low temperatures. Rushmere and Moffett (U.S. Pat. Nos. 5,470,435; 5,482,693; 5,543,014 and 5,503,820) describe the preparation of low concentration water soluble polyaluminosilicate microgels, which are used in the papermaking industry. Neither disclosure discusses any pharmaceutical or therapeutic use or additional utility in the removal of heavy metals, ammonia, mercaptans and other plant-, marine organism- and nuclear-derived toxins from living animals.

Miller and Bruenger (U.S. Pat. No. 5,494,935) discuss the use of lipophilic polyaminocarboxylic acids for the use of heavy metal chelation by oral application. These drugs can be targeted to various organs by modification of the length of the alkyl side chain. Undiscussed in their disclosure is the utility of insoluble, finely powdered substances which can tightly bind heavy metals, ammonia, mercaptans and other plant-, marine organism- and nuclear-derived toxins existing in gastric or intestinal juices inside these substances' interstitial crystalline cavities and channels. The method of excretion is unaddressed.

Hu, et al. (U.S. Pat. No. 5,487,882) disclose a method of producing crystalline synthetic faujasite of the zeolite "X" type. There is no disclosure of any medicinal, medical, or pharmaceutical uses or any application in the field of heavy metal binding, sequestering or removal from living organisms.

Leeper (U.S. Pat. No. 5,478,604) discloses a composition and method for preventing lead intoxication by the use of a coating which contains polyethylene imine, a calcium compound and/or a silicate that is applied to a surface which carries a coating of a lead based paint. The object of this invention is to reduce the digestion and absorption of lead from the intestinal tract in case the lead based paint is accidentally ingested. Specific features not found in this prior art is the use for treatment (as opposed to prevention) of lead poisoning, utility for heavy metals other than lead, months to years of administration, reduction of the total body burden of lead and other heavy metals, and deliberate oral administration in the form of a capsule or tablet all with the goal of reversing—partially or completely—adverse effects in heavy metal poisoned mammals. Additional utility for the removal of ammonia, mercaptans and other plant-, marine organism- and nuclear-derived toxins is not discussed.

Permnan and Schegel (U.S. Pat. No. 5,320,773) disclose a composition and method for purifying water in the form of a tablet containing betonite clay, attapulgite clay, polymeric coagulant and/or flocculent, biocide, zeolite and activated charcoal. The composition is added to contaminated water and removes turbidity, metal and organic contaminants. It is intended for personal use so that safe drinking water can be obtained by the simple addition of the composition to non-potable water. Schwarz, Putyera, Jagiello and Bandosz (U.S. Pat. No. 5,385,876) disclose a process and utility for molecularly engineered activated carbons which intercalates with a natural or synthetic clay producing a highly microporous absorbent material. An organic polymeric precursor is contacted therewith to fill the matrix interstices. The precursor is polymerized and carbonized to yield the absorbent material in which the carbon is intercalated into the mineral matrix. The material consists essentially of microporous sheets of active carbon spaced from one another to define slit-like micropores of a substantially uniform preselected width that is molecularly engineered such that interstices between the sheets correspond to a given target adsorbate. Only medical treatments such as "selective scavengers of ingested poisons" is mentioned as a potential medical use and is too general and non-specific to grasp the specific ideas the inventors had conceived of. Features not disclosed in these inventions include the use of the aforementioned compositions for biomedical use including the treatment of specifically heavy metal poisoning by oral administration of one or more capsules' worth of material daily for months to years intended, or an a more acute basis with administration into the stomach via nasogastric tube for the remediation of the effects of heavy metals, ammonia, mercaptans and other plant-, marine organism- and nuclear-derived toxins and their removable from the human body.

Rainer (U.S. Pat. No. 5,096,946) describes a polymer product for the selective absorption of dissolved ions, which is a water-swellable polymer which may be physically bound to an open celled cellulosic sponge and which is produced by a thermal process, which induces amide-forming insolubilization of polyethyleneimine. It has a high affinity for transition metal ions and may comprise a portion of a cellulosic sponge that is permeable to water yet remains substantially unaffected by water-borne suspended matter. The patent describes no utility as a pharmaceutical product intended for use as an orally-administered drug in humans or animals. The number of metals that it has utility in removing further limits it. Yet another limitation is the absence of any description of other non-transition metal toxic substances that it binds such as drugs, organic toxins, heavy metals and toxic moieties of plant and animal material accidentally ingested.

Withiam (U.S. Pat. No. 5,085,705) discloses a method of preparation and numerous compositions of alumina-silica-sulfates wherein the sulfate is present as a bound network. The compositions include articles of manufacture in the form of catalysts, rubber, plastics, paint and paper. Specifically, hollow microspheres containing a porous network are formed by spray drying a gelled composition followed by calcining of the spray-dried hollow microspheres to eliminate the sulfate network.

Dodwell and Smith (U.S. Pat. No. 5,053,139) describe a process for the removal of heavy metals from aqueous systems containing competing ions utilizing amorphous tin and titanium silicates. The basic principle of cation exchange, which is a property of certain specific tin- and titanium-based molecular sieve zeolites, is exploited in the exchange of several heavy metals with calcium and/or magnesium cations. This invention suffers from no discussion about pharmaceutical applications or biomedical uses and does not discuss any utility in removal of toxins from the bodies of animals or humans. Furthermore, the tin- and titanium-based molecular sieves discussed have an amorphous structure differing substantially from the present invention in which the crystalline structure is an important feature.

Kuznicki and Thrush (U.S. Pat. No. 4,994,191) disclose a process for the removal of heavy metals from aqueous solutions through the use of the crystalline molecular sieve having the X-ray diffraction pattern of ETS-10 or ETAS-10. They provide examples of the lead absorbing utility of these molecular sieves showing how the rate of lead binding increases with the framework type used. Important features of the present invention that are missing from this cited prior art is any utility as a pharmaceutical product, envisioned for internal ingestion by a human, that it may be utilized to remove lead absorbed in the tissues of an animal or human or that it may be used to remove other non-metallic toxins found in plant and/or animal materials which are accidentally ingested by humans.

Wason (U.S. Pat. No. 4,812,299) describes a family of novel and unique synthetic alkali metal alumino-silicates, also known as SAMS, which essentially comprises altered kaolin clay platelets with an integral rim or protuberance of essentially amorphous alkali silicate-kaolin reaction product. The unique SAMS compositions are structured materials in which the structure can be controlled and are useful as functional fillers, as titanium dioxide extenders, as silica extenders or as reinforcing agents for paper, paint, rubber, plastics and specialty products. This references does not even remotely suggest the utility of these materials for use in the pharmaceutical industry, as excipients or active products in the manufacture of medications for human and animal use, as active components in the removal of harmful substances such as heavy metals and/or animal or plant-borne toxins.

Hinchey (U.S. Pat. No. 4,348,369) discloses the discovery of, synthesis of and some chemical and physical properties of a novel synthetic crystalline zeolite of the molecular sieve type, designated "LZ-200", and envisioned to be used as an absorbent with demonstrated ability to absorb carbon dioxide, water and methanol. There is not the remotest suggestion of any biomedical uses, therapeutic uses or pharmacological uses of this material, especially in the treatment of toxin-based and heavy metal poisoning in humans is not discussed in the disclosure.

Etzel and Anand (U.S. Pat. No. 4,343,706) disclose a method of removing heavy from industrial waste streams by flocculation using a source of ferric ions and an alkaline material at a basic pH. Heavy metals are recovered by acidifying the floc in a narrow pH range, which liberates the heavy metals back into solution while leaving the floc particles intact and thus reusable. The concentrated heavy metals solution may also be recycled or disposed of in an acceptable manner. The use of this methods and material in humans, as pharmaceutical compositions or in any in vivo biomedical use is not even remotely described and is undesirable for several reasons including the administration of ferric ions and the basic pH which is required for this method to work and which is incompatible with administration by several routes into the human body.

Williams and Mays (U.S. Pat. No. 4,213,874) describe the synthesis of and several physicochemical properties of amorphous sodium aluminosilicate base exchange materials with ion exchange capacities equal or superior to known crystalline base exchangers and which may be used in water softening and detergents. Murrell, et al (U.S. Pat. No. 6,004,527) disclose a method for making molecular sieves with large pores and further describe novel molecular sieve compositions. Heller, Conger and Fitting (U.S. Pat. No. 5,994,933) disclose a method for distributing molecular sieve powder having a median particle size of less than about 350 microns, a method for maintaining the moisture content of the zeolite particles to greater than about 3 percent, and a method for refining the powder to reduce the size of the agglomerated clusters. The use of these materials in humans, as pharmaceutical compositions or in any in vivo biomedical use is not even remotely described.

MacDougall, et al (U.S. Pat. No. 5,882,625) describe a faujasite-like aluminosilicate, having a non-uniform aluminum distribution, which is synthesized by crystallizing the zeolite from a mixture of alkali metal aluminate and alkali metal silicate wherein the mixture has an alkali metal oxide ratio of at least 37. This zeolite has utility as a gas separation absorbent such as separating oxygen from nitrogen in the air. Otterstedt, Sterte and Schoeman (U.S. Pat. No. 5,863,516) describe colloidal suspensions of discrete particles of colloidal zeolite and a method for preparing such zeolite from clear tetraalkylammonium stabilized aluminum silicate solutions. The colloidal suspensions are characterized by an average particle size of less than 250 nanometers and a particle size distribution, expressed as a geometric standard deviation, of less than 1.30 nanometer. These zeolite sols exhibit Tyndall light scattering and very low rate of sedimentation owing to their small particle size. There is no suggestion of any biomedical, pharmaceutical or medical toxicology use.

Ueshima, et al (U.S. Pat. Nos. 5,810,920 and 5,769,938) describe a method for treating fly ash waste containing harmful metals in which the waste is mixed with a treating agent containing solid acids and/or cement and additionally a caking inhibitor, which is then kneaded with water where necessary and solidified by curing. Harmful metals, including lead, cadmium, mercury, chromium, copper, nickel and zinc are stabilized in solidified cakes from which they are not released. Reimers, Akers and Lo (U.S. Pat. No. 4,853,208) disclose a method of binding wastes in alkaline silicate matrix as a means of detoxifying wastes containing heavy metals including mercury, zinc, selenium, arsenic, antimony, copper and thallium. The alkaline silicate matrix binds the aforementioned metals and prevents their leaching out and contaminating the environment. There is not even a remote suggestion that the method and components described in this patent is intended for use in any biomedical, pharmaceutical or medical toxicology context for any of the metals, ammonia, mercaptans and other plant-, marine organism- and nuclear-derived toxins disclosed or others not mentioned.

Titterton and Summers (U.S. Pat. No. 5,744,404) describe a process and an article for delivering or applying a zeolitic molecular sieve to an odorous surface. The process involves contacting the surface with a porous article, which contains a slurry of a zeolitic molecular sieve having a $SiO_2/Al_2O_3$ ratio of at least 18. The slurry also contains water, ethanol, a suspending agent, a preservative and optionally an emollient. The porous article can be woven or non-woven and includes wipes, pads, foams and towelettes. The patent describes a biomedical application in which said method and resultant slurry is used to control foot odor. There is not even the remotest suggestion that this invention could be used internally or in the remediation of heavy metal poisoning or toxic metal ingestion in humans or animals.

Henriksen (U.S. Pat. No. 6,136,859) discloses a pharmaceutical formulation for treating liver disorders which is comprised of selenium, beta-carotene or vitamin A, ascorbic acid in its salt or ester form, alpha-tocopherol, methionine and coenzyme Q10 with a pharmaceutically acceptable carrier suitable for treating such diseases as primary biliary cirrhosis, viral hepatitis, steatohepatitis, alcoholic cirrhosis and related hepatic and biliary disorders. What is not appreciated in this disclosure is that primary biliary cirrhosis is associated with an elevated serum copper level. The underlying reason for this is unknown. This disclosure does not offer the remotest suggestion that amelioration of certain clinical findings of primary biliary cirrhosis are achievable by reduction of the elevated serum copper level. One method by which this may be achieved is by chelation therapy, either intravenously or enterally.

Nilsson and Stendahl (U.S. Pat. No. 5,662,826) describe a process for the preparation of a coagulating chemical comprising dissolving a solid zeolite in a solution of trivalent metal salt. The composition described is a coagulant for water purification in the fields of treating sewage water, in pulp and paper manufacture, in dewatering organic matter, and in concentrating minerals. Kuhm, Salz and Blasey (U.S. Pat. No. 5,645,811) describe a process for the production of very fine-particle zeolitic alkali metal aluminum silicates. Following a mixture of alkali metal silicate and alkali metal aluminate, in the presence of a stoichiometrically excessive amount of alkali metal hydroxide a gel is obtained and matured. Freeman, et al (U.S. Pat. No. 5,591,256) describe methods, uses and compositions of high-performance synthetic alkali metal alumino-silicates which are characterized by low oil absorption values, high total pore volume and increased differential pore volumes. The products are useful as coating pigments for paper, paperboard, paper fillers, paint pigments and as reinforcing pigments for rubber. There is not even the remotest suggestion of utility in biomedicine, pharmaceuticals, or that the products could be used in the remediation of heavy metal poisoning or toxic metal ingestion in humans or animals.

Li, et al (U.S. Pat. No. 5,584,912) describe a composition, a synthesis of a composition and a method of using the composition for selectively adsorptively separating nitrogen from oxygen wherein the composition is a crystalline EMT with a Si/Al ratio less than 2.0 and a micropore volume of at least 0.20 $cm^3/g$ and a lithium cation exchange of at least 80%. No pharmaceutical, biomedical or human medicinal or therapeutic use is described in this disclosure.

Tissler, et al (U.S. Pat. No. 5,578,195) describe a synthetic crystalline aluminosilicate of the pentasil type and method for using the same as catalysts or catalyst components in petrochemical processes for the catalytic conversion of hydrocarbons and their derivatives into useful organic compounds and intermediates. Pryor and Chi (U.S. Pat. No. 4,424,144) describe the preparation of binderless 3A zeolite absorbents, in the form of beads or extrudates and are envisioned for use in drying a mixture of a hydrocarbon, such as ethylene, and water. No pharmaceutical, biomedical or human medicinal or therapeutic use is described in this disclosure.

Kuhrts (U.S. Pat. No. 5,641,511) discloses a granular drug delivery system comprising a gel-forming dietary fiber that can be made into an orally-ingestible dispersion by admixture with a liquid that can deliver an effective dose of a pharmaceutically-active compound. Although this system appears useful in delivering desired amounts of a drug to the gastrointestinal tract, it is not envisioned for use in removing toxic or deleterious substances from the gut. Luck and Crabb (U.S. Pat. No. 6,074,689) disclose a method and composition for delivering an active protein or peptide to the colon comprising an aqueous solution of polyethylene glycol (PEG), the active protein or peptide, and an outer enteric coating. The intended use for this method and composition is for treatment of antibiotic induced *Clostridium difficile*-induced diarrhea where the active protein is hyperimmune bovine colostrum immunoglobulin (HBCIg) against the toxin elaborated by *Clostridium difficile*.

Bleim and Steffier (U.S. Pat. No. 5,500,212) disclose the composition of and preparation of a crosslinked amine-containing polymer with a polyfunctional amine-reactive compound such that water insolubility is achieved and bile acid sequestering capacity is enhanced over cholestyramine alone. Dhal, Holmes-Farley and Petersen (U.S. Pat. No. 6,294,163) disclose polymers containing guanidinium groups as bile acid sequestrants envisioned for use in lowering serum cholesterol levels. Figuly and Matos (U.S. Pat. No. 5,874,522) disclose crosslinked polymeric ammonium salts comprised of n-alkylene or alkyl-substituted n-alkylene groups and hydrocarbylene radicals containing one or more hydroxyl, ether, amino, thioether, keto or silyl groups envisioned for use in bile acid binding and serum cholesterol lowering. Goto and Meno (U.S. Pat. No. 6,022, 533) disclose a pharmaceutical composition comprising an anion exchange resin, silicon dioxide, crystalline cellulose and a pharmaceutical carrier. This disclosure relates primarily to the finding that formulation of non-crosslinked anion exchange resins, which had been considered impossible without water, is achievable with the use of silicon dioxide and crystalline cellulose. The tablets containing the anion exchange resin are envisioned for use in lowering cholesterol. Howard (U.S. Pat. No. 4,041,153) discloses methods and a pharmaceutical preparation for the treatment of hypercholesterolemia, which contains clofibrate, a basic anion exchange resin and a metal ion whose function is to form insoluble metal bile acid salts. The ingestible non-toxic metallic compound is capable of dissolving in the gastrointestinal juices to yield a metallic salt or ion that can react with bile acids to form an insoluble or poorly soluble metal salt of these bile acids. Huval, Holmes-Farley, Petersen and Dhal (U.S. Pat. No. 6,264,938) disclose a combination therapy for hypercholesterolemia, which is comprised of a conventional HMG-CoA reductase inhibitor and an unsubstituted polydiallylamine polymer, which acts as a bile acid sequestrant. Johnson (U.S. Pat. No. 4,649,048) discloses that quaternized vinylimidazole-ethylene glycol dimethacrylates useful to sequester non-absorbed bile acids in the intestinal tract to form a complex, which is then excreted in the feces. Jaxa-Chamiec, Hickey and Shah (U.S. Pat. Nos. 4,594,339; 5,230,885 and 5,273,740) disclose several classes of anion exchange polymers envisioned for use in treating hypercholesterolemia by binding free bile acids in gastrointestinal juice and sequestering them for eventual excretion out of the body with the feces. The specific anion exchange polymers disclosed include N,N-dimethyl-N-dodecylammoniomethyl-substituted polystyrene, N,N-dimethyl-N-dodecyl-ammoniomethylstyrene-ethyl methacrylate-divinylbenze and 6-(N,N-dimethyl-N-octylammonio)hexanoylated polystyrene chloride. Shaw and Sharma (U.S. Pat. No. 4,790,991) disclose ingestible aggregates comprising a pre-swelled anhydrous hydrocolloid and a substrate and are envisioned for use in treating a number of diseases including hypercholesterolemia and mineral deficiencies, in combination with the appropriate active pharmaceutical ingredient. Yang, Sharma, Sheu and Shaw (U.S. Pat. No. 4,778,676) disclose a chewable confectionery delivery system for active pharmaceutical ingredients and specifically cholestyramine intended for improve palatability in the treatment of hypercholesterolemia with a bile salt binding resin. Schulz (U.S. Pat. No. 5,167,965) discloses the composition of and method of producing palatable cholestyramine granules and tablets to be used in the treatment of hypercholesterolemia. These disclosures do not address any use in heavy metal poisoning and do not address any compositions such as zeolite molecular sieves.

McClelland and Zentner (U.S. Pat. No. 5,350,584) disclose a process for spheronization of charged resins, which produces multiparticulates 0.3-3 mm in diameter and which is microcrystalline free. Active pharmaceutical agents envisioned for incorporation into a granulation that is then spheronized include cholestyramine and trientine. Although each active pharmaceutical ingredient is used in specific circumstances, there is no specific mention of this process or these compositions to be used in the long-term remediation of heavy metal poisoning and removal of the heavy metal itself, nor is there any discussion about the use of zeolite molecular sieves.

Porath (U.S. Pat. No. 5,183,313) discloses an absorbent for metal ions, proteins and other inorganic and organic substances which is based upon a ligand with an atomic sequence of N—C—C—N where the specific sequence comprises part of a heteroaromatic ring system which is covalently bonded to a polymers such as a polysaccharide, polyvinyl alcohol or other organic hydrophilic polymer. The invention suffers from no description about any in vivo biomedical use such as may be effected by oral administration of a capsule or tablet. There is a further absence of any description of this material being employed in a heavy metal chelating mode for other heavy metals, including lead, uranium, and others, ammonia, mercaptans and other plant-, marine organism- and nuclear-derived toxins.

Hider, Kontoghiorghes and Silver (U.S. Pat. No. 4,585, 780) disclose a series of pharmaceutical compositions containing a 3-hydroxypyrid-2-one or 3-hydroxypyrid-4-one in which the atom attached to the nitrogen atom is replaced by an aliphatic acyl group, by an aliphatic hydrocarbon group, or by a substituted aliphatic hydrocarbon group to be used for the removal of toxic amounts of metals from the body.

These materials differ substantially from the present invention in that they are of an organic nature designed to permeate cellular membranes. In addition, the mode of action of these compounds is to enhance the water solubility and urinary excretion of metals such as iron, copper and aluminum. Yet another important difference from the present invention is the solubility of the chelating compound itself and its properties of systemic distribution.

Wieder (U.S. Pat. No. 4,352,751) discloses a series of species-linked diamine triacetic acids and their metal chelates whose general structure is comprised of an organic species containing at least one amine, hydroxyl or thiol functional group and a two or more atom long covalent bridge. Very different than the present invention, the utility proposed is in the monitoring the level of biologically and/or medically important molecules. This is achieved by incorporating into the metal binding sites, rare earth metal ions capable of forming fluorescent chelates that may be used in a fluorometric assay. No therapeutic intent is even remotely suggested in addition to the extremely small capacity to bind toxic metal or other toxins of medical interest for the purpose of their elimination.

Hinckley (U.S. Pat. No. 4,346,216) teaches the use of osmium carbohydrate complexes as pharmaceutical compositions for the treatment of heavy metal poisoning, arthritis and as a diagnostic aid as a radiographic contrast agent. Osmium-glucose complexes are proposed to be administered to mammals suffering from heavy metal poisoning which will result in a chelation of the heavy metal within the osmium complex in a harmless form which is then excreted from the system without further toxic effects on the treated animal. This approach suffers numerous disadvantages including the unavoidable and potentially deleterious deposition of osmium metal in tissues, unevaluated ability of the material to be absorbed from the gastrointestinal tract, and the need for multiple, frequent, chronic injections and undisclosed method of elimination from the body of a mammal. The mechanism of action also varies significantly from the present invention in that in that only lead is discussed as one of the heavy metals susceptible to this approach. Additionally, osmium is generally regarded as toxic to the human body and strict federal limits on the amount of osmium that may be deposited limits the utility of this approach.

Mandeville and Holmes-Farley (U.S. Pat. No. 5,702,696) disclose a family of hydrophilic anionic exchange resins for use in treating iron overload syndromes by decreasing the absorption of dietary iron. Sasaki and Ishii (U.S. Pat. No. 6,180,094) disclose a medicament, which comprises as an active ingredient a weakly basic anion exchange resin chelating with ferric ion, which adsorbs phosphate ions in vivo and is used for prevention and treatment of hyperphosphatemia. In this disclosure, the iron binding properties of cholestryamine are mentioned and the suggestion that iron deficiency anemia may be caused by its and other similar resins's use. Although there are certain advantages to this approach, there is no mention of any use of this method in the removal of heavy metals, ammonia, mercaptans and other plant-, marine organism- and nuclear-derived toxins nor is there mention that zeolite molecular sieves can be employed in the same manner.

Rosenberg (U.S. Pat. No. 4,107,331) describes a zinc chelating fungicidal composition in which zinc ions—which are required by certain species of fungi for growth—is sequestered in the chelating agent thereby preventing growth of human fungal infections. The chelating or sequestering agents described include water soluble salts of one of several EDTA-like organic compounds which is mixed with an aqueous jelly and administered vaginally for the treatment of common yeast infections. This disclosure suffers from a number of disadvantages for the treatment of chronic heavy metal poisoning including its use as a topical treatment and the use of organic and toxic chemicals about which little toxicity information in man is known. Additionally, oral administration for months in the form of a capsule, tablet, suspension or slurry for the purpose of removing heavy metals, ammonia, mercaptans and other plant-, marine organism- and nuclear-derived toxins from the body is not even remotely suggested.

Bergwitz-Larsen and Ulf (U.S. Pat. No. 5,643,560) disclose a drug formulation with ion exchangers of the carrageenan type for use in reducing toxic side effects and lethality when overdosing psychotropic medications. The drug and the carrageenan are administered together, but the carrageenan, through the process of ion exchange, in conjunction with an additional salt, minimizes absorption as reflected in animal model serum levels of clomipramine. This disclosure, however, fails to address the use of zeolite molecular sieves in vivo nor does it address the issue of chronic toxicity from tissue absorbed heavy metals, ammonia, mercaptans and other plant-, marine organism- and nuclear-derived toxins, nor does it address use ranging from months to years.

Howes and Newman (U.S. Pat. No. 6,045,834) disclose compositions and methods for the removal of mycotoxins from animal feed whereby a combination of modified yeast cell wall extract and mineral clay is fed to animals in amounts sufficient to inactivate mycotoxins present in the feeds. These compositions are intended to be admixed with feeds, incorporated directly into pelleted feeds or fed directly to animals. This invention suffers from several deficiencies for use in the treatment of heavy metal poisoning or toxic ingestions in man including preparation using the cell wall of yeasts which may contain unknown and/or undesirable contaminants or biologically active molecules and no description of any kind that said composition may be useful in other toxins such as heavy metals, ammonia, mercaptans and other plant-, marine organism- and nuclear-derived toxins.

Casas and Mosstam (U.S. Pat. No. 5,837,238) disclose a therapeutic method of treating rotavirus induced diarrhea by the administration of lyophilized and reconstituted *Lactobacillus reuteni* whose mechanism of action is unknown although it may be related to the elaboration of a substance named reuterin or improving the indigenous gastrointestinal microflora. Willoughby and Yolken (U.S. Pat. No. 5,192,551) disclose a neutral glycolipid GA1 (asialo-GM1 or asialo-gangliotetraosylceramide) as an adsorbent, either alone or bound to a non-absorbable resin or matrix, for the neutralization of enteric viral pathogens representing either prophylaxis in the case of a localized outbreak, or as a treatment in the case of florid gastroenteritis. Delivery modality is dependent on location; pharyngeal colonizing viruses is proposed to be accomplished by nebulization or gargling whereas gastrointestinal infection is treated specifically with internally ingested naked GA1 or GA1 bound to beads, resins, natural or synthetic polymers although yet additional delivery methods and pharmaceutical dosage forms are mentioned. This invention does not specifically claim to work by sequestration or ion exchange, it is not directed toward remediation of any toxic effect produced by heavy metal ingestion and it does not involve the use of zeolite molecular sieves.

Several disclosures reveal similar methods of increasing the nutritional value of mycotoxin-contaminated animal feed by feeding the animal montmorillonite clay [Beggs (U.S. Pat. No. 5,149,549)] or an acid-activated montmorillonite clay [Turk, Music and Beall (U.S. Pat. No. 5,639, 492)] simultaneously with the contaminated animal feed. The clay, itself which is not absorbed in the gastrointestinal tract but which absorbs or adsorbs any one of several known toxins (aflatoxin, fumonisin, vomitoxin, ochratoxin, zearalenone, ergot, and ergotamine). Taylor, Delaney and Phillips (U.S. Pat. Nos. 5,165,946 and 5,165,946) disclose a dry solid animal feed composition in which biodegradable feed is contaminated with a mycotoxin and is admixed with a mycotoxin inactivating agent comprising particles of a phyllosilicate mineral capable of inactivating mycotoxins. The particles are coated with a sequestering agent in an amount sufficient to enhance the mycotoxin inactivating capacity of the phyllosilicate. These inventions suffer from several deficiencies including no mention of the use of zeolite molecular sieves, no mention of the chronicity of administration, no mention of any additional nutritional deficiencies that may result from the clay administration and no mention of specificity of toxin binding within the framework structure. Specific pharmaceutical preparation for human use is not discussed. Moreover, human use was not described in these disclosures.

Geneix, Alafourcade and Ribereau-Gayon (U.S. Pat. No. 4,765,992) disclose a method of improving the alcoholic fermentation yield by the addition of cell walls that have been boiled or autolysed and washed. The cell walls act to bind the offending substances which include certain fatty acids and their ethyl esters, pesticide residues and substances secreted by microorganisms. There is not even the remotest suggestion that this invention has utility in biomedicine, pharmaceuticals or could be used in the remediation of heavy metal poisoning or toxic metal ingestion in humans or animals.

Robbins and Seely (U.S. Pat. No. 4,251,519) disclose a process of lowering or preventing an increase in the level of cholesterol and triglycerides in the blood of mammals by including a yeast glycan in the daily diet in an amount of up to 30% of the total food intake. There is not even the remotest suggestion that this invention has utility in biomedicine, pharmaceuticals or could be used in the remediation of heavy metal poisoning or toxic metal ingestion in humans or animals.

Coe, Gaffney, Srinivasan, Kirner, Pierantozzi and White (U.S. Pat. Nos. 4,925,460; 5,152,813 and 5,258,058) disclose different methods by which to achieve improved gas separation including the use of a lithium exchanged chabazite, a binary exchanged X-zeolite containing lithium, calcium and/or strontium ions, and additional divalent cation exchanged lithium X-zeolites. Maurer (U.S. Pat. No. 5,171,333) discloses a process for methane purification by pressure swing absorption employing a faujasite type of zeolite containing divalent and alkali metal and alkaline earth metal cations. Fitch, Bulow and Ojo (U.S. Pat. No. 5,464,467) disclose type X zeolites with charge compensating cations comprised of lithium, aluminum, cerium, lanthanum and/or mixed lanthanides are useful in gas separations. Chao, Sherman, Mullhaput and Bolinger (U.S. Pat. No. 5,413,625) disclose lithium/alkaline earth metal A and X zeolites are useful in separating oxygen and nitrogen from gas mixtures owing to their high absorptive capacity and high thermal stability. There is not even the remotest suggestion that the object of any of these inventions has utility in biomedicine, pharmaceuticals or could be used in the remediation of heavy metal poisoning or toxic metal ingestion in humans or animals.

A number of microporous compositions are described in the patent literature. Vaughan, Barrett, Strohmaier, Treacy and Newsam (U.S. Pat. Nos. 4,091,079; 4,333,859; 4,879,103 and 5,116,590) disclose the synthesis of several new materials including a synthetic large pore crystalline metal-silicate zeolite composition designated ECR-35, a crystalline aluminosilicate zeolite comprised of potassium and vanadium ions present in the reaction mixture designated VK-2, a high silica faujasite polymorph designated CSZ-3 which has claimed utility in sorption, separation and catalytic applications, and a zeolite characterized by triethyl methyl ammonium being entrapped in supercages of the aluminosilicate and designated ECR-30. Delprato, Guth, Angelrot, Didier and Zivkov (U.S. Pat. No. 5,393,511) disclose the synthesis of faujasite class zeolites in which numerous crown ethers and other carbon-containing macropolyrings of the polyoxadiazabicycloalkane class are employed as structuring agents. Wilson, Lok and Flanigen (U.S. Pat. No. 4,310,440) disclose a family of crystalline microporous aluminophosphate compositions, designated the $AlPO_4$ family of zeolites, the members of which are synthesized by hydrothermal crystallization at elevated temperatures of aluminophosphate gels containing a molecular structure-forming template and which are envisioned for use as catalysts or catalyst bases. Patton and Gajek (U.S. Pat. No. 4,473,663) disclose another crystalline aluminophosphate, designated $AlPO_4$-33, although it is distinct from the aforementioned $AlPO_4$ family described above. Chang, Chu, Dessau, Higgins, Lutner and Schlenker (U.S. Pat. No. 5,091,073) disclose a crystalline molecular sieve composition, designated MCM-37, which may be used in the catalytic conversion of organic compounds. Brock and Acara (U.S. Pat. No. 4,950,952) disclose a crystalline zeolite, designated T, and Breck, Blass, and Skeels (U.S. Pat. No. 4,503,023) disclose silicon substituted zeolite compositions which are contacted with an aqueous solution of a fluorosilicate salt using controlled proportions and temperature and pH conditions which avoid aluminum extraction. Casci, Lowe and Whittam (U.S. Pat. No. 4,537,754) disclose the composition of and the method of producing zeolite EU-1 which is useful in catalytic processes such as xylenes isomerization. Grose and Flanigen (U.S. Pat. No. 4,124,686) disclose a crystalline zeolite, designated phi, which is prepared hydrothermally from aqueous gels, exhibits large-pore adsorption characteristics and is envisioned for use in hydrocarbon conversion processes exemplified by isoparaffin alkylation, hydrocracking isomerization and reforming. Morimoto, Takatsu and Sugimoto (U.S. Pat. No. 4,578,259) disclose a crystalline aluminosilicate and its structural variations, collectively designated ISI-6, which are envisioned for use as catalysts for the conversion of oxygen-containing organic compounds such as alcohols and ethers into hydrocarbons. Plank, Rosinski and Rubin (U.S. Pat. No. 4,016,245) disclose a crystalline zeolite, designated ZSM-35, which is envisioned for use as an absorbent or a catalyst. Sand and Dodwell (U.S. Pat. No. 4,081,514) disclose a process for producing acid-stable, fluidizable mordenite particles in the size range of 20 to 150 nanometers and envisioned for use as an absorbant, catalyst support and ion-exchange medium. Sand (U.S. Pat. No. 4,093,699) independently discloses a method for making synthetic offretite, which is acid treated, and is capable of intercrystalline absorption of benzene and molecules greater than 5 Å. Cormier and Sand (U.S. Pat. No. 4,017,590) disclose the preparation of synthetic ferrierite by a hydrothermal process in which there is co-precipitation of silica-alumina gels and sodium and potassium carbonates and bicarbonates and which is envisioned for use in separating molecules 6.2 Å and smaller from larger molecules. Kuznicki and Whyte (U.S. Pat. No. 5,011,667) disclose a process of forming self-bound sodium chabazite and designated EC-20 which shows superiority in absorption and ion-exchange capacity when compared to the natural form. Velten and Demmel (U.S. Pat. No. 4,826,793) disclose a method of incorporating small crystalline catalytic ingredients into an attrition-resistant matrix by the use of binder formulations prepared from amorphous silica, alumina, and zirconia. The particles are less than 4 pun and contain the catalyst component ZSM-5, low-soda exchanged type Y-zeolite or ultra-stable type Y zeolite. The resulting material is spray-dried and calcined and which has shown resistance to attrition and particle density change. In each of these disclosures there is not even the remotest suggestion that these inventions have utility in biomedicine, pharmaceuticals or could be useful in the remediation of heavy metal poisoning or toxic metal ingestion in humans or animals.

Bacon Kurtz and Fitzpatrick (U.S. Pat. No. 6,270,755) disclose a series of anionic polymers as toxin binders intended for use in binding pathogenic toxins elaborated by microorganisms including bacteria and protozoa. Kurtz and Fitzpatrick (U.S. Pat. No. 6,290,946) disclose a series of polystyrene sulfonate-based polymers also intended for use in binding pathogenic toxins from microorganisms. Fitzpatrick, Huval, Bacon Kurtz, Mandeville and Neenan (U.S. Pat. Nos. 6,007,803 and 6,290,947) disclose a cationic polymer comprised of a monomer having a pendant ammonium group and a hydrophobic monomer envisioned for use in binding pathogenic toxins elaborated by microorganisms including bacteria and protozoa. Heerze and Armstrong (U.S. Pat. No. 6,107,282) disclose prevention and/or treatment of antibiotic associated diarrhea and pseudomembranous enterocolitis arising from *Clostridium difficile* toxin B using 8-methoxycarbonyl oligosaccharides. These compositions bind the toxin and neutralize it thereby mitigating and potentially preventing the toxin's pathological effects. Such oligosaccharides have been shown to be eliminated completely and rapidly from the rat gastrointestinal tract. These inventions suffer from no description of any use in removing heavy metals, ammonia, mercaptans and other plant-, marine organism- and nuclear-derived toxins either recently ingested or absorbed into tissue from chronic exposure.

Other forms of heavy metal detoxification are clearly needed for chronic administration.

The inorganic structural class of molecular sieves or zeolites is comprised of more than 1000 members, many of which we believe possess useful medicinal, pharmacological and biopharmaceutical properties in this therapeutic area.

Zeolites are a class of inorganic crystalline microporous solids comprised mostly of silicates and phosphates although arsenates and germanates are also represented. Zeolites possess a framework density (FD) of approximately 12.1 to 20.6 tetrahedrally coordinated atoms (also known as T-atoms) per 1000 Å$^3$ (cubic angstroms). Such frameworks are comprised of a number of repeated identical or different structural components termed secondary building units (SBU). To date, approximately 20 SBUs have been described. The framework for a specific zeolite defines the pore and channel sizes; these pore and channel diameters vary across different zeolites. The pore and channel diameters, also termed "crystallographic free diameters," influence the rate of diffusion of water and dissolved ions through the framework. A number of zeolite groups with 20-, 18-, 14-, 12-, 10-, 9-, and 8-ring structures are known to exist. Depending on the relative molecular charge in the space surrounding the pores positively or negatively charged ions are attracted or repelled. Ions of similar charge and size may be substituted for each other or "exchanged" thereby producing the "ion exchange" phenomenon for which zeolites are well known.

Zeolites offer a unique approach to treating heavy metal poisoning because of their intrinsic chemical and physical stability and their general biological inertness. The specific zeolite isotypic groups considered to be useful in the wide spectrum of heavy metal intoxication include the 20-, 18- and 14-ring structures designated by the terms and abbreviations: Cloverite (–CLO), VPI-5 (VFI), AlPO-8 (AET), CIT-5 (CFI), UTD-1F (DON), OSB-1 (OSO); the 12-ring structures AlPO-5 (AFI), SAPO-40 (AFR), MAPSO-46 (AFS), CoAPO-50 (AFY), ASU-7 (ASV), AlPO-31 (ATO), MAPO-36 (ATS), Beta (BEA), Boggsite (BOG), Beryllophosphate-H (BPH), Cancrinite (CAN), CIT-1 (CON), Chiral Zincophosphate (CZP), DAF-1 (DFO), EMC-2 (EMT), Faujasite (FAU), Gmelinite (GME), GUS-1 (GON), ITQ-4 (IFR), ITQ-7 (ISV), Linde Type L (LTL), Mazzite (MAZ), ZSM-18 (MEI), Mordenite (MOR), ZSM-12 (MTW), Offretite (OFF), UiO-6 (OSI), Roggianite (RON), STA-1 (SAO), UCSB-8Co (SBE), UCSB-6GaCo (SBS), UCSB-10GaZn (SBT), SSZ-48 (SFE), VPI-8 (VET); the 10-ring structures AlPO-11 (AEL), AlPO-41 (AFO), AlPO—H2 (AHT), Co—Ga-Phosphate-5 (CGF), Co—Ga-Phosphate-6 (CGS), Dachiardite (DAC), Epistilbite (EPI), EU-1 (EUO), Ferrierite (FER), Heulandite (HEU), Laumontite (LAU), ZSM-11 (MEL), ZSM-5 (MFI), ZSM-57 (MFS), ZSM-23 (MTT), MCM-22 (MWW), NU-87 (NES), Partheite (PAR), SSZ-44 (SFF), SSZ-35 (STF), Stilbite (STI), Terranovaite (TER), Theta-1 (TON), Weinebenite (WEI), Wenkite (WEN). The specific zeolite isotypic groups considered to be useful in the wide spectrum of heavy metal intoxication also include the 9-ring structures designated by the terms and abbreviations: Chiavennite (CHI), Lovdarite (LOV), Natrolite (NAT), RUB-17 (RSN), SSZ-23 (STT), VPT-7 (VSV). The specific zeolite isotypic groups considered to be useful in the wide spectrum of heavy metal intoxication also include the 8-ring structures designated by the terms and abbreviations: Li-A (ABW), ACP-1 (ACO), AlPO-18 (AEI), AlPO-EN3 (AEN), AlPO-14 (AFN), AlPO-52 (AFT), SAPO-56 (AFX), Analcime (ANA), AlPO-C (APC), AlPO-D (APD), MAPO-39 (ATN), AlPO-12-TAMU (ATT), AlPO-25 (ATV), AlPO-21 (AWO), AlPO-22 (AWW), Bikitaite (BIK), Brewsterite (BRE), Cesium Aluminosilicate (CAS), Chabazite (CHA), Deca-dodecasil 3R (DDR), DAF-2 (DFT), TMA-E (EAB), Edingtonite (EDI), Erionite (ERI), ERS-7 (ESV), Gismondine (GIS), Goosecreekite (GOO), ITQ-3 (ITE), NaJ (JBW), ZK-5 (KFI), Levyne (LEV), Linde Type A (LTA), Merlinoite (MER), Montesommaite (MON), MCM-35 (MTF), Paulingite (PAU), Phillipsite (PHI), Rho (RHO), RUB-3 (RTE), RUB-13 (RTH), STA-6 (SAS), STA-2 (SAT), Mg-STA-7 (SAV), Thomsonite (THO), Tsch6rtnerite (TSC), VPI-9 (VNI), Yugawaralite (YUG), ZAPO-M (ZON). These zeolites are described by Baerlocher and colleagues (Baerlocher Ch., Meier, W M and D H Olson. Atlas of Zeolite Framework Types, 5$^{th}$ revised ed., Elsevier, 2001, pp. 3-18).

One related mineral, magnesium aluminum silicate [1327-43-1] also termed aluminum magnesium silicate [12511-31-8] is available commercially as a pharmaceutical excipient. It is used in a range concentrations in the pharmaceutical industry and functioning as an absorbent, a binding agent, a disintegrant, an oral or topical emulsion stabilizer, an oral or topical suspending agent, a stabilizing agent and a viscosity modifier. It is obtained from the silicate ores of the montmorillonite group and occurs as an off-white to creamy white, odorless, tasteless, soft, slippery small flakes or as fine micronized powder. It is practically insoluble in alcohols, water and organic solvents. It can swell to many times its original volume in water and may be dried and rehydrated many times. It is stable indefinitely when stored under dry conditions and is stable over a wide pH range. It absorbs some organic substances but appears to be compatible with organic solvents. It is generally regarded as nontoxic and nonirritating at levels employed as a pharmaceutical excipient. Subacute animal feeding studies in rats and dogs fed magnesium aluminum silicate at 10% of their diet for 90 days were negative including autopsy and histopathological examination. The oral $LD_{50}$ for the rat is 16 g/kg. Magnesium aluminum silicate is included in the Food and Drug Administration's (FDA) Inactive Ingredients Guide.

The present invention relates to the use of zeolites, both natural and artificial, in the treatment of diseases related to heavy metals and ammonia in humans. Based on the relative affinities and diameters of the metallic ions, certain metals will bind preferentially to certain zeolites, thus creating the ability to design lattice structures of precise dimensions for each of the heavy metals that are known poisons in man. The specific metals known to cause human disease in elevated quantities include lead, copper, tin, arsenic, antimony, beryllium, bismuth, boron, cadmium, chromium, cobalt, copper, iron, lead, lithium, magnesium, nickel, selenium, silver, strontium, thallium, tin, titanium, vanadium, zinc, mercury. It is envisioned that the zeolite would be administered orally in the form of a capsule, tablet, powder or slurry daily or multiple times daily for weeks' to months' duration. Zeolites are generally insoluble in the aqueous environments present in the human gastrointestinal tract such as acid pH in the stomach, alkaline pH of the duodenum for the few hours of normal transit time. Dealuminization is known to occur in acidic environments with some zeolites. The neutral pH of the jejunum, ileum, cecum, colon and rectum do not pose a dealuminization or solubility risk. It is known to bind lead and copper when administered orally in an in vivo system.

Although zeolites and similar ion exchange, inorganic, relatively insoluble materials are claimed, the specific zeolite to be employed is the sodium aluminum silicate, CAS [12141-46-7]. As shown in the Material Safety Data Sheet (Material Safety Data Sheet for sodium aluminum silicate, CAS [12141-46-7] manufactured by Mineral-Right, Inc., Phillipsburg, Kans. Revised Mar. 22, 1995) it consists in its physical state as a solid in the form of granular crystals, which are white-opaque in color. The specific gravity of sodium aluminum silicate is 0.80. It is insoluble in pH neutral aqueous solution. It is formed from two ingredients: hydrated alumina [1344-28-1] 21% and sodium silicate [134409-8] 68%. It is known to be non-toxic to ingestion. It is subject to the following environmental protection procedures: conventional housekeeping methods. It is to be handled similar to earth. This material demonstrates temperature-dependent weight loss upon heating which appears to be unchanged in the temperature range between approximately 350° F. and 1200° F. (Research Report Covering High Temperature Tests on the MR-1 Synthetic Zeolite, Baumbach Labs, Appleton, Wis.; Dec. 30, 1993). At higher temperatures, the "Zeolite Reflection Phenomenon" has been observed.

Examples of zeolites useful in the present invention include zeolite Li-A (Barrer and White) (Barrer R M, et al., *J. Chem. Soc.* 1267-1278, 1951; Kerr I S, *Z. Kristallogr.* 139:186-195, 1974; Krogh Anderson E, et al. *Z. Kristallogr.* 176:67-73, 1986); [Be—As—O]-ABW (Gier T E, et al. *Nature* 349:508-510, 1991; Harrison W T A, et al., *Acta Crystallogr.* C51:181-183, 1995); [Be—P—O]-ABW (Gier T E, et al., *Nature* 349:508-510, 1991; Harrison W T A, et al., *Acta Crystallogr.* C51:181-183, 1995; Robl C, et al. *J. Chem. Soc. Dalton Trans.* 1911-1912; 1993); [Ga—Si—O]-ABW (Newsam J M, *J. Phys. Chem.* 92:445-452; 1988); [Zn—As—O]-ABW (Gier T E, et al. *Nature* 349:508-510; 1991); [Zn—P—O]-ABW (Gier T E, et al. *Nature* 349:508-510; 1991); ICs-I[Mg—P—O]-ABW (Rakotomahanina Raloisoa E L, *Ph.D. Thesis, U. Grenoble;* 1972); ICs-I[Al—Si—O]-ABW (Klaska R, et al. *Naturwiss.* 60:299, 1973; Klaska R, et al. *Z. Kristallogr.* 142:225-238, 1975); ICs-I[Al—Ti—O]-ABW (Gatehouse B M, et al. *Acta Crystallogr.* C45:1674-1677, 1989); ILi-I[Al—Si—O]-ABW (Ghorbarkar H, *Cryst. Res. Technol.* 27:1071-1075, 1992); ILi-I[Zn—P—O]-ABW (Harrison W T A, et al. *J. Solid State Chem.* 114:249-257, 1995); ILi-I[Al—Ge—O]-ABW (Tripathi A, et al., *Microporous and Mesoporous Materials,* 34:273-279, 2000); INa-I[Co—P—O]-ABW (Chippindale A M, et al., *Acta Crystallogr.,* C55: 845-847, 1999); IRb-I[Co—P—O]-ABW (Rakotomahanina Raloisoa E L, *Ph.D. Thesis, U. Grenoble,* 1972); IRb-I[Al—Si—O]-ABW (Klaska R, et al., *Naturwiss.,* 60: 299, 1973; Klaska R, et al., *Z. Kristallogr.* 142:225-238, 1975); ITl-I[Al—Si—O]-ABW (Krogh Anderson E, et al., *Zeolites,* 11: 149-154, 1991); ACP-1 (Feng P Y, et al., *Nature,* 388: 735-741, 1997); AlPO-18 (Simmen A, et al., *Zeolites,* 11:654-661, 1991; U.S. Pat. No. 4,310,440, 1982); AlPO-11 (Bennett J M, et al., *Zeolites,* 7: 160-162, 1987; Richardson Jr J W, et al., *Acta Crystallogr.,* B44: 367-373, 1988; Wilson S T, et al., U.S. Pat. No. 4,310,440, 1982); MnAPO-11 (Pluth J J, et al., *J. Phys. Chem.,* 92: 2734-2738, 1988); SAPO-11 and compositional variants (Flanigen E M, et al., *Pure Appl. Chem.,* 58: 1351-1358, 1986; Flanigen E M, et al., *In Proc. 7$^{th}$ Int. Zeolite Conf.,* Japan, 103-112, 1986); AlPO-EN3 (Parise J B, *Stud. Surf. Sci. Catal.,* 24: 271-278, 1985); [Ga—P—O]-AEN (Glasser F P, et al., *Acta Crystallogr.,* C50:848-850, 1994); AlPO-53(A) (Kirchner R M, et al., *Microporous and Mesoporous Materials.* 39: 319-332, 2000); AlPO-53(B) (Kirchner R M, et al., *Microporous and Mesoporous Materials,* 39: 319-332, 2000); CFSAPO-1A (He H, et al., *J. Incl. Phenom.,* 5: 591-599, 1987); JDF-2 (Chippindale A M, et al., *Acta Crystallogr.,* C50: 1537-1540, 1994); MSC-1 (Simmen A, et al., *Ph.D. Thesis,* ETH Zurich, Switzerland, 1992); UiO-12-500 (Kongshaug K O, et al., *Microporous and Mesoporous Materials,* 39: 333-339, 2000); UiO-12-as (Kongshaug K O, et al., *Microporous and Mesoporous Materials,* 39: 333-339, 2000); AlPO-8 (Dessau R M, et al., *Zeolites,* 10: 522-524, 1990; Richardson Jr J W, *Zeolites,* 12: 13-19, 1992); MCM-37 (Chu C T W, U.S. Pat. No. 5,091,073, 1992); Afghanite (Barian P, et al. *Bull. Soc. Fr. Mineral. Cristallogr.* 91: 34-42, 1968; Merlino S, et al. *Zeolite 1976, Program and Abstracts,* Tucson Ariz., 1976; Pobedimskaya E A, et al. *Dokl. Akad. Nauk SSSR* 320: 882-886, 1991; Ballirano P, et al. *Eur. J. Mineral* 9: 21-31, 1997); AlPO-5 (Bennett J M, et al. *ACS Sym. Ser.* 218: 109-118, 1983; U.S. Pat. No. 4,310,440, 1982); CoAPO-5 (Chao K J, et al. *J. Chem. Soc., Faraday Trans.* 88: 2949-2954, 1992); CrAPO-5 (Radaev S, et al. *J. Mater. Chem.* 6:1413-1418, 1996); SAPO-5 and its compositional variants (Flanigen E M, et al. *Pure Appl. Chem* 58: 1351-1358, 1986; Flanigen E M, et al. *In Proc. 7$^{th}$ Int. Zeolite Conf.,* Japan, pp. 103-112, 1986); SSZ-24 (Bialek R, et al., *Zeolites* 11: 438-442, 1991); TPAF AlPO-5 (Qiu S, et al. *Zeolites* 9:440-444, 1989); AlPO-14 (Broach R W, et al. In *Proc. 12$^{th}$ Int. Zeolite Conf,* USA, pp. 1715-1722, 1999); GaPO-14 (Parise J B, et al. *Acta Crystallogr.* C42: 670-673, 1986); AlPO-41 (Kirchner R M, et al. *Zeolites* 14:523-528, 1994); SAPO-40 (Estermann M A, et al. *J. Appl. Crystallogr.* 25:539-543, 1992;

Dumont N, et al. *Microporous Materials* 1:149-160, 1993; McCusker L B, et al. *Microporous Materials* 6:51-54, 1996); AlPO-40 (Ramaswamy V, et al. *Microporous and Mesoporous Materials* 31:1-8, 1999); CoAPSO-40 and ZnAPSO-40 (Lourence J P, et al. ??*Journal*?? 38:267-278, 2000); MAPSO-46 (Bennett J M, et al. *Stud. Surf Sci. Catal.* 37:269-279, 1988); AlPO-52 (Bennett J M, et al. *Stud. Surf. Sci. Catal.* 49:731-739, 1989; McGuire N K, et al. *Zeolites* 15:460-469, 1995); SAPO-56 (Wilson S T, et al. *Microporous and Mesoporous Materials* 28:125-137, 1999); SSZ-16 (Lobo R F, et al. *Chem. Mater.* 8:2409-2411, 1996); CoAPO-50 (Bennett J M, et al. *Stud. Surf Sci. Catal.* 37: 269-279, 1988); MgAPO-50 (Akolekar D B, et al. *Zeolites* 15: 583-590, 1995); AlPO—H2 (Li H X, et al. *Chem. Commun.* ??Vol??: 403-405, 1993; Kennedy G J, et al., *Solid State Nucl. Mag. Res* 4: 173-178, 1995); Analcime (Taylor W H Z Z. *Kristallogr* 74:1-19, 1930; Knowles C R, et al. *Indian Mineral.* 6:127-, 1965; Ferraris G, et al. *Z. Kristallogr.* 135: 240-252, 1972); [Al—Co—P—O]-ANA (Feng P Y, et al. *Nature* 388: 735-741, 1997); [Al—Si—P—O]-ANA (Artioli G, et al. *Acta Crystallogr.* C40:214-217, 1984); [Ga—Ge—O]-ANA (Bu X, et al. *J. Am. Chem. Soc.* 120:13389-13397, 1998); |Cs-Na—(H$_2$O)||Ga—Si—O]-ANA (Yelon W B, et al. *Zeolites* 10:553-558, 1990); |Cs$_{16}$|[Cu$_8$Si$_{40}$O$_{96}$]-ANA (Heinrich A R, et al. *Acta Crystallogr.* C47:237-241, 1991); |K-|[B—Si—O]-ANA (Millini R, et al. *Microporous Materials* 1:9-15, 1993); AlPO-24 (Wilson S T, et al. *J. Am. Chem. Soc.* 104:1146-1147, 1982); AlPO$_4$-pollucite (Keller E B, *Ph.D. Thesis*, ETH Zurich, Switzerland, 1987); Ammonioleucite (Hori H, et al. *Am. Mineral.* 71:1022-1027, 1986); Ca-D (Ames L L, et al. *Am. Mineral.* 43:476-480, 1958); Cs beryllosilicate pollucite (Torres-Martines L M, et al., *J. Solid State Chem.* 51: 100-103, 1984); Cs, Fe silicate pollucite (Kopp O C, et al. *Am. Mineral.* 48:100-109, 1963); Hsianghualite (Wen-Hui H, et al. *Am. Mineral.* 44:1327-1328, 1959); Kehoeite (McConnell D, et al. *Can. Mines.* 12:352-, 1974); Leucite (Peacor D R, *Z. Kristallogr.* 127: 213-224, 1968); Na—B (Barrer R M, et al. *J. Chem. Soc.* ??vol??: 1561-1571, 1952); Pollucite (Nel H J, *Am. Mineral.* 29: 443-451, 1944); Synthetic analcime (Ghobarker H, et al. *Cryst. Res. Technol.* 1071-1075, 1986); Synthetic hsinghualite (Ghobarker H, et al. *Annal. Chemie, Science Materiaux* 24:209-215, 1999); Synthetic wairakite (Ghobarker H, et al. *Cryst. Res. Technol.* K90-92, 1985); Wairakite and additional compositional variants (Takeuchi Y. et al. *Am. Mineral.*, 64: 993-1001, 1979); AlPO-C (Bennett J M, et al. *Zeolites* 6:349-359, 1986; Keller E B, et al. *Solid State Ionics* 43: 93-103(?), 1990; AlPO—H3 (Pluth J J, et al. *Acta Crystallogr.* C42:1118-1120, 1986); AlPO-D (Keller E B, et al. *Solid State Ionics* 43:93-103, 1990); AlPO-16 (Bennett J M, et al., *Zeolites* 11:502-506, 1991); Octadecasil (Caullet P, et al. *Eur. J. Solid State Inorg. Chem.* 28:345-361, 1991); ASU-7 (Li H, et al. *J. Am. Chem. Soc.* 120:10569-10570, 1998); MAPO-39 (McCusker L B, et al. *Acta Crystallogr.* A46:C59(?), 1990; Baur W H, et al. *Z. Kristallogr.* 214:154-159, 1999); AlPO-31 (Bennett J M, et al. *Zeolites* 12:338-342, 1992; Baur W H, et al. *Acta Crystallogr. B*50: 290-294, 1994); SAPO-31 (Flanigen E M, et al. *Pure Appl. Chem.* 58:1351-1358, 1986; Flanigen E M, et al. In *Proc. 7$^{th}$ Int. Zeolite Conf.*, Japan, pp. 103-112, 1986; Baur W H, et al. *Acta Crystallogr. B*50:290-294, 1994); MAPO-36 (Smith J V, et al. *Zeolites* 13: 166-169, 1993); AlPO-12-TAMU (Rudolf P R, et al. *J. Phys. Chem.* 90:6122-6125, 1986); AlPO-33 (Smith J V, et al. *PRIVATE COMMUNIC*; Patton R L, et al. U.S. Pat. No. 4,473,663, 1984); AlPO-25 (Richardson Jr J W, et al., *J. Phys. Chem.* 94: 3365-3367, 1990); [Ga—P—O]-ATV (Parise J B, *Chem. Communic.* ??vol??:606-607, 1985); AlPO-21 (Bennett J M, et al. *Inorg. Chem.* 24:188-193, 1985; Parise J B, et al. *Acta Crystallogr.* C41:515-520, 1985); [Ga—P—O]-ATV (Parise J B, *Chem. Communic.* 606-607, 1985); AlPO-22 (Richardson Jr J W, et al. *Naturwiss.* 76:467-469, 1989); Beta (Higgins J B, et al. *Zeolites* 8:446-452, 1988; Newsam J M, et al. *Proc. R. Soc. Lond. A* 420: 375-405, 1988); [B—Si—O]-*BEA (Marler B, et al. *In Proc. 9$^{th}$ Int. Zeolite Conf.*, pp. 425-432, 1993; Reddy K S N, et al. *J. Incl. Phenom. Mol. Recogn. Chem.* 20:197-210, 1994); [Ga—Si—O]-*BEA (Reddy K S N, et al. *J. Incl. Phenom. Mol. Recogn. Chem.* 20:197-210, 1994); CIT-6 (Takewaki T, et al. *Topics in Catalysis* 9:35-42, 1999); Tschernichite (Boggs R C, et al. *Am. Mineral.* 78:822-826, 1993); Bikitaite (Kocman V, et al., *Am. Mineral.* 59:71-78, 1974; Stähl K, et al. *Zeolites* 9:303-311, 1989); |Ca-|[Al—Si—O]-BIK (Annehed H, et al. *Z. Kristallogr.* 166:301-306, 1984); Triclinic bikitaite (Bissert G, et al. *N. Jb. Miner. Mh.* ??vol??:241-252, 1986); Boggsite (Pluth J J, et al. *Am. Mineral.* 75:501-507, 1990); Beryllophosphate-H (Harvey G, *Z. Kristallogr.* 182:123-124, 1988; Harvey G, et al. *Z. Kristallogr.* 201:113-123, 1992); Linde Q (Andries K J, et al. *Zeolites* 11:124-141, 1991); STA-5 (Patinec V, et al. *Chem. Mater.* 11:2456-2462, 1999); Brewsterite (Perrotta A J, et al. *Acta Crystallogr.* 17:857-862, 1964; Schlenker J L, et al. *Acta Crystallogr.* B33:2907-2910, 1977); Ba-dominant brewsterite (Cabella R, et al. *Eur. J. Mineral.* 5:353-360, 1993); CIT-4 (Khodabandeh S, et al. *Microporous and Mesoporous Materials* 11:87-95, 1997); Synthetic bewsterite (Ghobarker H, et al. *German Patent AZ* 198 24 184.4-41, 1997); Cancrinite (Pauling L, *Proc. Natl. Acad. Sci.* 16:453-459, 1930; Jarchow O, *Z Kristallogr.* 122:407-422, 1965); [Al—Ge—O]-CAN (Belokoneva E L, et al. *Sov. Phys. Crystallogr.* 31:516-519, 1986); [Ga—Si—O]-CAN (Newsam J M, et al. *Zeolites* 7:569-573, 1987); [Zn—P—O]-CAN (Yakubovich O V, et al. *Crystallogr. Reports* 39:564-568, 1994); Basic cancrinite (Barrer R M, et al. *J. Chem. Soc.* 1561-1571, 1952; Bresciana Pahor N, et al. *Acta Crystallogr.* B38:893-895, 1982); Cancrinite hydrate (Wyart J, et al. *Compt. Rend.* 229:131-, 1949); Davyne (Hassan I, et al. *Can. Mineral.* 28:341-349, 1990); ECR-5 (Vaughn D E W, *E. Patent A-190*, 90; 1986); Microsommite (Bonaccorsi E, et al. *Phys. Chem. Mineral.* 22:367-374, 1995); Synthetic cancrinite (Smolin Y I, et al. *Kristallografiya* 26:63-66, 1981); Tiptopite (Peacor D R, et al., *Am. Mineral.*, 72:816-820, 1987); Vishnevite (Hassan I, et al. *Can. Mineral.* 22:333-340, 1984); Cesium aluminosilicate (Araki T Z, *Z. Kristallogr.* 152:207-213, 1980); CIT-5 (Wagner P, et al. *Chem. Commun.* 2179-2180, 1997; Yoshikawa M, et al. *J. Phys. Chem. B* 102:7139-7147, 1998); C—Ga-Phosphate-5 (Chippindale A M, et al. *Zeolites* 18:176-181, 1997); C—Ga-Phosphate-6 (Cowley A R, et al. *Microporous and Mesoporous Materials* 28:163-172, 1999); [Zn—Ga—P—O]-CGS (Cowley A R, et al. *Microporous and Mesoporous Materials* 28:163-172, 1999); TNU-1 (Hong S B, et al. *J. Mater. Chem.* 9:2287-2289, 1999); [Ga—Si—O]-CGS (Hong S B, et al. *J. Mater. Chem.* 9:2287-2289, 1999); TsG-1 (Lee Y J, et al. *J. Mater. Chem.* 11:879-880, 1999); [Ga—Si—O]-CGS (Lee Y J, et al. *J. Mater. Chem.* 11:879-880, 1999); Chabazite (Dent L S, et al. *Nature* 181:1794-1796, 1958; Smith J V, et al. *Acta Crystallogr.* 16:45-53, 1963); [Al—Co—P—O]-CHA (Feng P Y, et al. *Nature* 388:735-741, 1997); [Co-Al—P—O]-CHA (Feng P Y, et al. *Nature* 388:735-741, 1997; Feng P, et al. *Microporous and Mesoporous Materials* 23:221-229, 1998); [Mg—Al—P—O]-CHA (Feng P, et al. *Microporous and Mesoporous Materials* 23:221-229, 1998); AlPO-34 (Harding M M, et al. *Acta Crystallogr.* C50:852-854, 1994); CoAPO-44 (Bennett J M, et al. *Stud. Surf Sci. Catal* 37:269-

279, 1988); CoAPO-47 (Bennett J M, et al. *Stud Surf Sci. Catal.* 37:269-279, 1988); Dehydrated Na-Chabazite (Mortier W J, et al. *Mater. Res. Bull.* 12:241-250, 1977); GaPO-34 (Schott-Darie C, et al. *Stud. Surf. Sci. Catal.* 84:101-108, 1994); LZ-218 (Breck D W, et al. U.S. Pat. No. 4,333,859, 1982); Linde D (Breck D W, et al. U.S. Pat. No. 2,950,952, 1960; Lillerud K P, et al. *J. Chem. Soc., Faraday Transactions* 90:1547-1551, 1994); and/or the other framework minerals, both natural and synthetic, a table of which appears below.

TABLE 4

| Name of Zeolite | First Author Cited | Citation | Vol. | Page or Number | Year |
|---|---|---|---|---|---|
| Linde R | Milton R M | British Patent | | 841,812 | 1960 |
| MeAPO-47 | Bennett J M, et al. | *Stud. Surf. Sci. Catal.* | 37: | 269-279 | 1988 |
| | Flanigen E M, et al. | *Pure Appl. Chem.* | 58: | 1351-1358 | 1986 |
| | Flanigen E M, et al. | In *Proc. 7$^{th}$ Int. Zeolite Conf.*, Japan | | 103-112 | 1986 |
| MeAPSO-47 | Bennett J M, et al. | *Stud. Surf. Sci. Catal.* | 37: | 269-279 | 1988 |
| | Flanigen E M, et al. | *Pure Appl. Chem.* | 58: | 1351-1358 | 1986 |
| | Flanigen E M, et al. | In *Proc. 7$^{th}$ Int. Zeolite Conf.*, Japan | | 103-112 | 1986 |
| Phi | Lillerud K P, et al. | *J. Chem. Soc., Faraday Transactions* | 90: | 1547-1551 | 1994 |
| | Grose R W, et al. | U.S. Pat. No. | | 4,124,686 | 1978 |
| SAPO-34 | Lok, B M, et al. | *J. Am. Chem. Soc.* | 106: | 6092-6093 | 1984 |
| SAPO-37 | Pluth J J, et al. | *J. Phys. Chem.* | 93: | 6516-6520 | 1989 |
| Si-CHA | Díaz-Cabañas M J, et al. | *Chem. Commun.* | | 1881-1882 | 1998 |
| Willhendersonite | Tillmanns E, et al. | *N. J.. Miner. Mh.* | | 547-558 | 1984 |
| ZK-14 | Kuehl G H | PRIVATE COMMUNICATION | | | |
| | Kuehl G H | In *Molecular Sieves*, (ed. R. M. Barrer) | | 85-91 | 1968 |
| ZYT-6 | Ito M, et al. | *Acta Crystallogr.* | C41: | 1698-1700 | 1985 |
| Herschelite | Discredited | | | | |
| Chiavennite | Tazzoli V, et al. | *Eur. J. Mineral.* | 7: | 1339-1344 | 1995 |
| Cloverite | Esterman M, et al. | *Nature* | 352: | 320-323 | 1991 |
| CIT-1 | Lobo R F, et al. | *J. Am. Chem. Soc.* | 117: | 3764-3779 | 1995 |
| SSZ-26 | Lobo R F, et al. | *J. Am. Chem. Soc.* | 117: | 3764-3779 | 1995 |
| | Lobo R F, et al. | *Science* | 262: | 1543-1546 | 1993 |
| SSZ-33 | Lobo R F, et al. | *J. Am. Chem. Soc.* | 117: | 3764-3779 | 1995 |
| | Lobo R F, et al. | *Science* | 262: | 1543-1546 | 1993 |
| Chiral Zincophosphate | Rajic N, et al. | *Zeolites* | 15: | 672-678 | 1995 |
| | Harrisson W T A, et al. | *Chem. Mater.* | 8: | 145-151 | 1996 |
| Dachiardite | Gottardi G, et al. | *Z. Kristallogr.* | 119: | 53-64 | 1963 |
| | Vezzalini G Z | *Z. Kristallogr.* | 166: | 63-71 | 1984 |
| Svetlozarite | Discredited | | | | |
| | Gellens L R, et al. | *Mineral. Mag.* | 45: | 157-161 | 1982 |
| Deca-dodecasil 3R | Gies H | *Z. Kristallogr.* | 175: | 93-104 | 1986 |
| Sigma-1 | Stewart A, et al. | *Stud. Surf. Sci. Catal.* | 37: | 57-64 | 1988 |
| ZSM-58 | Valyocsik E W | U.S. Pat. No. | | 4,698,217 | 1987 |
| | Ernst S, et al. | In *Zeolites for the Nineties, Recent Progress Reports - Abstracts* | 8$^{th}$ IZC | 55-56 | 1989 |
| DAF-1 | Wright P A, et al. | *Chem. Commun.* | | 633-635 | 1993 |
| DAF-2 | Chen J, et al. | *Angew. Chem., Int. Ed.* | 33: | 639-640 | 1994 |
| ACP-3 | Bu X, et al. | *J. Solid State Chem.* | 136: | 210-215 | 1998 |
| UCSB-3GaGe | Bu X, et al. | *J. Am. Chem. Soc.* | 120: | 13389-13397 | 1998 |
| UCSB-3ZnAs | Bu X, et al. | *J. Solid State Chem.* | 136: | 210-215 | 1998 |
| UiO-20 | Kongshuang K O, et al. | *Chem. Mater.* | 12: | 1095-1099 | 2000 |
| Dodecasil 1H | Gerke H, et al. | *Z. Kristallogr.* | 166: | 11-22 | 1984 |
| UTD-1F | Wessels T, et al. | *J. Am. Chem. Soc.* | 121: | 6242-6247 | 1999 |
| UTD-1 | Lobo R F, et al. | *J. Am. Chem. Soc.* | 119: | 8474-8484 | 1997 |
| TMA-E (Aiello and Barrer) | Aiello R, et al. | *J. Chem. Soc. (Å).* | | 1470-1475 | 1970 |
| | Meier W M, et al. | *J. Solid State Chem.* | 37: | 204-218 | 1981 |
| Bellbergite | Rüdinger B, et al. | *Miner. Petrol.* | 48: | 147-152 | 1993 |
| Edingtonite | Taylor W H, et al. | *Z. Kristallogr.* | 86: | 53-64 | 1933 |
| | Galli E | *Acta Crystallogr.* | B32: | 1623-1627 | 1976 |
| | Kvick Å, et al. | *J. Chem. Phys.* | 79: | 2356-2362 | 1983 |
| [Co—Al—P—O]-EDI | Bu X, et al. | *Chem. Mater.* | 10: | 2546-2551 | 1998 |
| [Co—Ga—P—O]-EDI | Bu X, et al. | *Chem. Mater.* | 10: | 2546-2551 | 1998 |
| K—F | Barrer R M, et al. | *J. Chem. Soc.* | | 2882-2891 | 1956 |
| | Baerlocher Ch, et al. | *Z. Kristallogr.* | 140: | 10-26 | 1974 |
| Linde F | Sherman J D | *ACS Sym. Ser.* | 40: | 30-42 | 1977 |
| Synthetic edingtonite | Ghobarker H, et al. | *Cryst. Res. Technol.* | 32: | 653-657 | 1997 |
| Tetragonal edingtonite | Mazzi F, et al. | *N. Jb. Miner. Mh.* | | 373-382 | 1984 |
| Zeolite N | Christensen A N, et al. | *Acta Chemica Scand.* | 51: | 969-973 | 1997 |
| EMC-2 | Delprato F, et al. | *Zeolites* | 10: | 546-552 | 1990 |
| | Baerlocher Ch, et al. | *Microporous Materials* | 2: | 269-280 | 1994 |

TABLE 4-continued

| Name of Zeolite | First Author Cited | Citation | Vol. | Page or Number | Year |
| --- | --- | --- | --- | --- | --- |
| CSZ-1 | Barrett M G, et al. | UK Patent | | GB 2,076,793 | 1981 |
| ECR-30 | Vaughn D E W | E Patent | | 0,351,461 | 1989 |
| ZSM-20 | Newsam J M, et al. | Chem. Commun. | | 493-495 | 1989 |
| ZSM-3 | Kokotailo G T, et al. | Adv. Chem. Ser. | 101: | 109-121 | 1971 |
| Epistilbite | Kerr I S | Nature | 202: | 589 | 1964 |
| | Perrotta A J | Mineral. Mag. | 36: | 480-490 | 1967 |
| | Alberti A, et al. | Z. Kristallogr. | 173: | 257-265 | 1985 |
| | Yang P, et al. | Eur. J. Mineral. | 8: | 263-271 | 1996 |
| Synthetic epistilbite | Ghobarkar H | Cryst. Res. Technol. | | 151-1573(?) | 1984 |
| Erionite | Staples L W, et al. | Mineral. Mag. | 32: | 261-281 | 1959 |
| | Kawahara A, et al. | Bull. Soc. Fr. Minéral. Cristallogr. | 92: | 250-256 | 1969 |
| | Gard J A, et al. | In Proc. 3rd Int. Cong. Molecular Sieves | | 94-99 | 1973 |
| AlPO-17 | Pluth J J, et al. | Acta Crystallogr. | C42: | 283-286 | 1986 |
| | Flanigen E M, et al. | Pure Appl. Chem. | 58: | 1351-1358 | 1986 |
| | Flanigen E M, et al. | In Proc. 7$^{th}$ Int. Zeolite Conf. | | 103-112 | 1986 |
| LZ-220 | Breck D W, et al. | U.S. Pat. No. | | 4,503,023 | 1985 |
| Linde T | Breck D W | Zeolite Molecular Sieves | | 173 | 1974 |
| ERS-7 | Campbell B J, et al. | Chem. Commun. | | 1725-1726 | 1998 |
| | Millini R, et al. | In Proc. 12$^{th}$ Int. Zeolite Conf. | | 541-548 | 1999 |
| EU-1 | Casci J L, et al. | U.S. Pat. No. | | 4,537,754 | 1985 |
| | Briscoe N A, et al. | Zeolites | 8: | 74-76 | 1988 |
| TPZ-3 | Sumitani K, et al. | E Patent | | EP 51318 | 1982 |
| ZSM-50 | Rohrbaugh W J | Private communication | | | |
| Faujasite | Bergerhoff G, et al. | N. Jb. Miner. Mh. | | 193-200 | 1958 |
| | Baur W H | Am. Mineral. | 49: | 697-704 | 1964 |
| [Al—Ge—O]-FAU | Barrer R M, et al. | J. Chem. Soc. | | 195-208 | 1959 |
| [Co—Al—P—O]-FAU | Feng P Y, et al. | Nature | 388: | 735-741 | 1997 |
| [Ga—Ge—O]-FAU | Barrer R M, et al. | J. Chem. Soc. | | 195-208 | 1959 |
| Beryllophosphate X | Gier T E, et al. | Zeolites | 12: | 770-775 | 1992 |
| CSZ-1 | Barrett M G, et al. | UK Patent | | BG 2,076,793 | 1981 |
| ECR-30 | Vaughn D E W | E Patent | | 0,351,461 | 1989 |
| LZ-210 | Breck D W, et al. | U.S. Pat. No. | | 4,503,023 | 1985 |
| Linde X | Milton R M | U.S. Pat. No. | | 2,882,244 | 1959 |
| | Olson D H, et al. | J. Phys. Chem. | 74: | 2758-2764 | 1970 |
| Linde Y | Breck D W | U.S. Pat. No. | | 3,130,007 | 1964 |
| | Costenoble M L, et al. | J. Chem. Soc., Faraday Trans. I | 72: | 1877-1883 | 1976 |
| SAPO-37 | Lok B M, et al. | J. Am Chem. Soc. | 106: | 6092-6093 | 1984 |
| Siliceous Na—Y | Hriljac J J, et al. | J. Solid State Chem. | 106: | 66-72 | 1993 |
| ZSM-20 | Newsam J M, et al. | Chem. Commun. | | 493-495 | 1989 |
| ZSM-3 | Kokotailo G T, et al. | Adv. Chem. Ser. | 101: | 109-121 | 1971 |
| Zincophosphate X | Gier T E, et al. | Zeolites | 12: | 770-775 | 1992 |
| Ferrierite | Vaughn P A | Acta Crystallogr. | 21: | 983-990 | 1966 |
| [Ga—Si—O]-FER | Jacob N E, et al. | Zeolites | 13: | 430-434 | 1993 |
| [Si—O]-FER | Gies H, et al. | Zeolites | 7: | 442-445 | 1987 |
| | Morris R E, et al. | J. Am. Chem. Soc. | 116: | 11849-11855 | 1994 |
| FU-9 | Seddon D, et al. | E Patent | | B-55,529 | 1985 |
| ISI-6 | Morimoto N, et al. | U.S. Pat. No. | | 4,578,259 | 1986 |
| Monoclinic ferrierite | Gramlich-Meier R, et al. | Am. Mineral. | 70: | 619-623 | 1985 |
| NU-23 | Whittam T V | E Patent | | A-103-981 | 1984 |
| Sr-D | Barrer R M, et al. | J. Chem. Soc. | | 2296-2305 | 1964 |
| ZSM-35 | Plank C J, et al. | U.S. Pat. No. | | 4,016,245 | 1977 |
| Franzinite | Ballirano P, et al. | Can. Mineral. | 38: | 657-668 | 2000 |
| Gismondine | Fischer K, et al. | Adv. Chem. Ser. | 101: | 250-258 | 1971 |
| [Al—Co—P—O]-GIS | Feng P Y, et al. | Nature | 388: | 735-741 | 1997 |
| [Co—Al—P—O]-GIS | Feng P, et al. | Microporous and Mesoporous Materials | 23: | 221-229 | 1998 |
| [Co—Ga—P—O]-GIS | Cowley A R, et al. | Chem. Commun. | | 673-674 | 1996 |
| [Co—P—O]-GIS | Yuan H M, et al. | Inorg. Chem. | 39: | 1476-1479 | 2000 |
| [Ga—Si—O]-GIS | Cho H H, et al. | Chem. Mater. | 12: | 2292-2300 | 2000 |
| [Mg—Al—P—O]-GIS | Feng P, et al. | Microporous and Mesoporous Materials | 23: | 221-229 | 1998 |
| [Zn—Ga—P—O]-GIS | Chippindale A M, et al. | Microporous and Mesoporous Materials | 24: | 133-141 | 1998 |

TABLE 4-continued

| Name of Zeolite | First Author Cited | Citation | Vol. | Page or Number | Year |
|---|---|---|---|---|---|
| \|(NH$_4$)$_4$\|[Zn$_4$B$_4$P$_8$O$_{32}$]-GIS | Kniep R, et al. | Angew. Chem. Int. Ed. | 38: | 3642-3644 | 1999 |
| \|Cs$_4$\|[Zn$_4$B$_4$P$_8$O$_{32}$]-GIS | Kniep R, et al. | Angew. Chem. Int. Ed. | 38: | 3642-3644 | 1999 |
| \|Rb$_4$\|[Zn$_4$B$_4$P$_8$O$_{32}$]-GIS | Kniep R, et al. | Angew. Chem. Int. Ed. | 38: | 3642-3644 | 1999 |
| Amicite | Alberti A, et al. | Acta Crystallogr. | B35: | 2866-2869 | 1979 |
| Garronite | Artioli G | Am. Mineral. | 77: | 189-196 | 1992 |
| | Artioli G, et al. | Powder Diffraction | 14: | 190-194 | 1999 |
| Gobbinsite | McCusker L B, et al. | Z. Kristallogr. | 171: | 281-289 | 1985 |
| High-silica Na—P | Hakansson U, et al. | Acta Crystallogr. | C46: | 1361-1362 | 1990 |
| Low-silica Na—P (MAP) | Albert B R, et al. | Microporous and Mesoporous Materials | 21: | 133-142 | 1998 |
| MAPO-43 | Pluth J J, et al. | J. Am. Chem. Soc. | 111: | 1692-1698 | 1989 |
| MAPSO-43 | Flanigen E M, et al. | Pure Appl. Chem. | 58: | 1351-1358 | 1986 |
| | Flanigen E M, et al. | In Proc. 7$^{th}$ Int. Zeolite Conf. | | 103-112 | 1986 |
| Na—P1 | Baerlocher Ch, et al. | Z. Kristallogr. | 135: | 339-354 | 1972 |
| Na—P2 | Hansen S, et al. | Acta Crystallogr. | C46: | 1361-1362 | 1990 |
| SAPO-43 | Helliwell M, et al. | Acta Crystallogr. | B49: | 413-420 | 1993 |
| Synthetic Ca-garronite | Schropfer L, et al. | Eur. J. Mineral. | 9: | 53-65 | 1997 |
| Synthetic amicite | Ghobarkar H, et al. | Mater. Res. Bull | 34: | 517-525 | 1999 |
| Synthetic garronite | Ghobarkar H, et al. | Mater. Res. Bull | 34: | 517-525 | 1999 |
| Synthetic gobbinsite | Ghobarkar H, et al. | Mater. Res. Bull | 34: | 517-525 | 1999 |
| TMA-gismondine | Baerlocher Ch, et al. | Helv. Chim. Acta | 53: | 1285-1293 | 1970 |
| Gismondite | discredited | | | | |
| Synthetic zeolite B | disused | | | | |
| Gmelinite | Fischer K | N. Jb. Miner. Mh. | | 1-13 | 1966 |
| K-rich gmelinite | Vezzalini G, et al. | N. Jb. Miner. Mh. | | 504-516 | 1990 |
| Synthetic fault-free gmelinite | Daniels R H, et al. | J. Am. Chem Soc | 100: | 3097-3100 | 1978 |
| Sarcolite | Discredited | | | | |
| GUS-1 | Plévert J, et al. | Chem. Commun. | | 2363-2364 | 2000 |
| Goosecreekite | Rouse R C, et al. | Am. Mineral. | 71: | 1494-1501 | 1986 |
| Heulandite | Merkle A B, et al. | Am. Mineral. | 52: | 273-276 | 1967 |
| | Alberti A | Tschermarks Min. Petr. Min. | 18: | 129-146 | 1972 |
| Clinoptilolite | Koyama K, et al. | Z. Kristallogr. | 145: | 216-239 | 1977 |
| Dehydrated Ca, NH$_4$-Heulandite | Mortier W J, et al. | Am. Mineral. | 66: | 309-314 | 1981 |
| LZ-219 | Breck D W, et al. | U.S. Pat. No. | | 4,503,023 | 1985 |
| ITQ-4 | Barrett P A, et al. | Chem. Mater. | 9: | 1713-1715 | 1997 |
| MCM-58 | Valyo, E W | WOP | | 9511196 | 1995 |
| SSZ-42 | Chen C Y, et al. | Chem. Commun. | | 1775-1776 | 1997 |
| ITQ-7 | Villaescusa L A, et al. | Angew. Chem. Int. Ed. | 38: | 1997-2000 | 1999 |
| ITQ-3 | Camblor, M A, et al. | Angew. Chem. Int. Ed. | 36: | 2659-2661 | 1997 |
| Na-J (Barrer and White) | Hansen S, et al. | Zeolites | 2: | 162-166 | 1982 |
| Nepheline hydrate | Rheinhardt A, et al. | Fortsch. Mineral. | 60: | 175-176 | 1982 |
| Synthetic \|Na—\|[Al—Si—O]-JBW | Ragimov K G, et al. | Sov. Phys. Dokl. | 23: | 697-698 | 1978 |
| ZK-5 | Meier W M, et al. | Z. Kristallogr. | 121: | 211-219 | 1965 |
| (Cs, K)-ZK-5 | Robson H E | U.S. Pat. No. | | 3,270,753 | 1973 |
| | Parise J B, et al. | Z. Kristallogr. | 165: | 175-190 | 1983 |
| P | Barrer R M, et al. | Z. Kristallogr. | 135: | 374-390 | 1972 |
| Q | Barrer R M, et al. | Z. Kristallogr. | 135: | 374-390 | 1972 |
| Laumontite | Bartl H, et al. | Jb. Miner. Mh. | | 33-42 | 1967 |
| | Amirov S T, et al. | Dokl. Akad. Nauk SSSR | 174: | 667- | 1967 |
| | Schramm V, et al. | Adv. Chem. Ser. | 101: | 259-265 | 1971 |
| | Artioli G, et al. | Zeolites | 17: | 249-255 | 1993 |
| [Co—Ga—P—O]-LAU | Chippindale A M, et al. | Chem. Commun. | | 2453-2454 | 1994 |
| | Bond A D, et al. | Zeolites | 19: | 326-333 | 1997 |
| [Fe—Ga—P—O]-LAU | Bond A D, et al. | Zeolites | 19: | 326-333 | 1997 |
| [Mn—Ga—P—O]-LAU | Bond A D, et al. | Zeolites | 19: | 326-333 | 1997 |
| Synthetic laumontite | Ghorbarkar H, et al. | Microporous and Mesoporous Materials | 23: | 55-60 | 1998 |
| Leonhardite (discredited) | Lapham D L | Am. Mineral. | 48: | 683-689 | 1963 |
| Levyne | Barrer R M, et al. | Trans. Faraday Soc. | 55: | 1915-1923 | 1959 |
| | Merlino S, et al. | Min. Petr. Mitt. | 22: | 117-129 | 1975 |
| AlPO-35 | Zhu G S, et al. | Microporous Materials | 11: | 269-273 | 1997 |
| CoDAF-4 | Barrett P A, et al. | Phys. Chem. Chem. Phys. | 2: | 407-412 | 2000 |
| LZ-132 | Tvaruzkova Z, et al. | Int. Zeolite Sym., Wurzburg, Extended Abstracts | | | 1988 |

TABLE 4-continued

| Name of Zeolite | First Author Cited | Citation | Vol. | Page or Number | Year |
|---|---|---|---|---|---|
| NU-3 | McCusker L B | *Mater. Sci. Forum* | 133-136: | 423-433 | 1993 |
| SAPO-35 | Lok B M, et al. | *J. Am. Chem. Soc.* | 106: | 6092-6093 | 1984 |
| ZK-20 | Kerr G T | U.S. Pat. No. | | 3,459,676 | 1969 |
| Liottite | Merlino S, et al. | *Am. Mineral.* | 62: | 321-326 | 1977 |
| | Ballirano P, et al. | *Can. Mineral.* | 34: | 1021-1030 | 1996 |
| Losod | Sieber W, et al. | *Helv. Chim. Acta* | 57: | 1533-1549 | 1974 |
| | Schicker P | Ph. D. Thesis, ETH Zürich, Switzerland | | | 1988 |
| [Al—Ge—O]-LOS | Sokolov Yu. A., et al. | *Sov. Phys. Dokl.* | 23: | 789-791 | 1978 |
| \|Li—\|[Be—P—O]-LOS | Harrison W T A, et al. | *Zeolites* | 13: | 242-248 | 1993 |
| Bystrite | Pobedimskaya E A, et al. | *Sov. Phys. Dokl.* | 36: | 553-555 | 1991 |
| Lovdarite | Merlino S | *Acta Crystallogr.* (Suppl.) | A37: | C189 | 1981 |
| | Merlino S | *Eur. J. Mineral.* | 2: | 809-817 | 1990 |
| Synthetic lovdarite | Ueda S, et al. | Preprints of Poster Papers, 7$^{th}$ Int. Zeolite Conf. | | | 1986 |
| Linde Type A | Reed T B, et al. | *J. Am. Chem. Soc.* | 78: | 5972-5977 | 1956 |
| | Gramlich V, et al. | *Z. Kristallogr.* | 133: | 134-149 | 1971 |
| [Al—Ge—O]-LTA | Barrer R M, et al. | *J. Chem. Soc.* | | 195-208 | 1959 |
| [Ga—P—O]-LTA | Simmen A, et al. | In *Proc. 9$^{th}$ Int. Zeolite Conf.* | | 433-440 | 1993 |
| Alpha | Wadlinger R L, et al. | U.S. Pat. No. | | 3,375,205 | 1968 |
| LZ-215 | Breck D W, et al. | U.S. Pat. No. | | 4,503,023 | 1985 |
| N-A | Barrer R M, et al. | *J. Chem. Soc.* | | 971-982 | 1961 |
| SAPO-42 | Lok B M, et al. | *J. Am. Chem. Soc.* | 106: | 6092-6093 | 1984 |
| ZK-21 | Kuehl G H | *Inorg. Chem.* | 10: | 2488-2495 | 1971 |
| ZK-22 | Kuehl G H | *Inorg. Chem.* | 10: | 2488-2495 | 1971 |
| ZK-4 | Kerr G T | *Inorg. Chem.* | 5: | 1537-1539 | 1966 |
| Linde Type L | Barrer R M, et al. | *Z. Kristallogr.* | 128: | 352-370 | 1969 |
| (K, Ba)-G, L | Baerlocher Ch., et al. | *Z. Kristallogr.* | 136: | 245-254 | 1972 |
| Gallosilicate L | Wright P A, et al. | *Nature* | 318: | 611-614 | 1985 |
| | Newsam J M, et al. | *Mater. Res. Bull.* | 21: | 661-672 | 1986 |
| LZ-212 | Breck D W, et al. | U.S. Pat. No. | | 4,503,023 | 1985 |
| Perlialite | Menshikov Y P | *Vses. Mineral. O-va* | 113: | 607-612 | 1984 |
| | Artioli G, et al. | *Eur. J. Mineral.* | 2: | 749-759 | 1990 |
| Linde Type N | Fälth L, et al. | *Z. Kristallogr.* | 160: | 313-316 | 1982 |
| NaZ-21 | Sheplev Yu F, et al. | *Dokl. Akad. Nauk SSSR* | 272: | 1133-1137 | 1983 |
| Mazzite | Galli E | *Cryst. Struct. Comm.* | 3: | 339-344 | 1974 |
| | Galli E | *Rend. Ital. Mineral. Petrol.* | 31: | 599-612 | 1975 |
| [Ga—Si—O]-MAZ | Newsam J M, et al. | *Mater. Res. Bull.* | 20: | 125-136 | 1985 |
| LZ-202 | Breck D W, et al. | U.S. Pat. No. | | 4,503,023 | 1985 |
| Omega | Galli E | *Cryst. Struct. Comm.* | 3: | 339-344 | 1974 |
| ZSM-4 | Rubin M K, et al. | U.S. Pat. No. | | 4,021,447 | 1977 |
| ZSM-18 | Lawton S L, et al. | *Science* | 247: | 1319-1321 | 1990 |
| ZSM-11 | Kokotailo G T, et al. | *Nature* | 275: | 119-120 | 1978 |
| | Fyfe C A, et al. | *J. Am. Chem. Soc.* | 111: | 2470-2474 | 1989 |
| | Van Koningveld H, et al. | In *Proc. 12$^{th}$ Int. Zeolite Conf.* | | 2419-2424 | 1999 |
| Bor-D (MFI/MEL intergrowth) | Perego G, et al. | *J. Appl. Crystallogr.* | 17: | 403-410 | 1984 |
| Boralite D | Taramasso M, et al. | GB Patent | | 2,024,790 | 1980 |
| SSZ-46 | Terasaki O, et al. | *Chem. Mater.* | 8: | 463-468 | 1996 |
| | Nakagawa Y, et al. | U.S. Pat. No. | | 5,968,474 | 1999 |
| Silicalite 2 | Bibby D M, et al. | *Nature* | 280: | 664-665 | 1979 |
| TS-2 | Reddy J S, et al. | *Zeolites* | 12: | 95-100 | 1992 |
| Melanophlogite | Gies H | *Z. Kristallogr.* | 164: | 247-257 | 1983 |
| | Gies H, et al. | *N. Jb. Miner. Mh.* | | 119-124 | 1982 |
| Merlinoite | Passaglia E, et al. | *N. Jb. Miner. Mh.* | | 355-364 | 1977 |
| | | *N. Jb. Miner. Mh.* | | 1-9 | 1979 |
| [Al—Co—P—O]-MER | Feng P Y, et al. | *Nature* | 388: | 735-741 | 1997 |
| \|Ba—\|[Al—Si—O]-MER | Gottardi G, et al. | *Natural Zeolites* (book) | | 157 | 1985 |
| \|Ba—Cl—\|[Al—Si—O]-MER | Solov'eva L P, et al. | *Sov. Phys. Crystallogr.* | 16: | 1035-1038 | 1972 |
| \|NH4—\|[Be—P—O]-MER | Bu X, et al. | *Microporous and Mesoporous Materials* | 26: | 61-66 | 1998 |
| K-M | Gottardi G, et al. | *Natural Zeolites* (book) | | 157 | 1985 |
| | Barrer R M, et al. | *J. Chem. Soc.* | | 2882-2891 | 1956 |
| Linde W | Gottardi G, et al. | *Natural Zeolites* (book) | | 157 | 1985 |
| | Sherman J D | *ACS Sym. Ser.* | 40: | 30-42 | 1977 |

TABLE 4-continued

| Name of Zeolite | First Author Cited | Citation | Vol. | Page or Number | Year |
|---|---|---|---|---|---|
| Synthetic Merlinoite | Barrett P A, et al. | J. Mater. Chem. | 8: | 2263-2268 | 1998 |
| Zeolite W | Bieniok A, et al. | J. Mater Chem. | 6: | 271-275 | 1996 |
| ZSM-5 | Kokotailo G T, et al. | Nature | 272: | 437-438 | 1978 |
|  | Olson D H, et al. | J. Phys. Chem. | 85: | 2238-2243 | 1981 |
|  | Van Koningsveld H, et al. | Acta Crystallogr. | B43: | 127-132 | 1987 |
| [As—Si—O]-MFI | Bhaumik A, et al. | Chem. Commun. |  | 869-870 | 1995 |
| [Fe—Si—O]-MFI | Patarin J, et al. | Zeolites | 10: | 674-679 | 1990 |
| [Ga—Si—O]-MFI | Awate S V, et al. | J. Incl. Phenom. | 13: | 207-218 | 1992 |
| AMS-1B | Klotz M R | U.S. Pat. No. |  | 4,269,813 | 1981 |
| AZ-1 | Chono M, et al. | E. Patent |  | B-113,116 | 1984 |
| Bor-C | Taramasso M, et al. | In Proc. 5$^{th}$ Int. Zeolite Conf. |  | 40-48 | 1980 |
| Boralite C | Taramasso M, et al. | GB Patent |  | 2,024,790 | 1980 |
| Encilite | Ratnasamy P, et al. | E. Patent |  | A-160,136 | 1985 |
| FZ-1 | Suzuki T, et al. | E. Patent |  | B-31,255 | 1981 |
| LZ-105 | Grose R W, et al. | U.S. Pat. No. |  | 4,257,885 | 1981 |
| Monoclinic H-ZSM-5 | Van Koningsveld H, et al. | Zeolites | 10: | 235-242 | 1990 |
| Mutinaite | Vezzalini G, et al. | Zeolites | 19: | 323-325 | 1997 |
| NU-4 | Whittam T V | E. Patent |  | B-65,401 | 1986 |
| NU-5 | Whittam T V | E. Patent |  | B-54,386 | 1982 |
| Silicalite | Flanigen E M, et al. | Nature | 271: | 512-516 | 1978 |
| TS-1 | Taramasso M, et al. | U.S. Pat. No. |  | 4,410,501 | 1983 |
| TSZ | Ashibe K, et al. | E. Patent |  | A-101,232 | 1984 |
| TSZ-III | Sakurada S, et al. | E. Patent |  | A-170,751 | 1986 |
| TZ-01 | Iwayama K, et al. | E. Patent |  | A-57,016 | 1982 |
| USC-4 | Young D A | U.S. Pat. No. |  | 4,325,929 | 1982 |
| USI-108 | Hinnenkamp J A, et al. | U.S. Pat. No. |  | 4,423,020 | 1983 |
| ZBH | Holderich W, et al. | E. Patent |  | B-77,946 | 1986 |
| ZKQ-1B | Kee Kwee L S L | E. Patent |  | A-148,038 | 1984 |
| ZMQ-TB | Kee Kwee L S L | E. Patent |  | A-104,107 | 1983 |
| ZSM-57 | Schlenker J L, et al. | Zeolites | 10: | 293-296 | 1990 |
| Montesommaite | Rouse R C, et al. | Am. Mineral. | 75: | 1415-1420 | 1990 |
| Mordenite | Meier W M | Z. Kristallogr. | 115: | 439-450 | 1961 |
| [Ga—Si—O]-MOR | Eapen M J, et al. | J. Incl. Phenom. | 14: | 119-129 | 1992 |
| Ca-Q | Koizumi M, et al. | J. Geol. | 68: | 41-53 | 1960 |
| LZ-211 | Breck D W, et al. | U.S. Pat. No. |  | 4,503,023 | 1985 |
| Large pore mordenite | Sand L B | In Molecular Sieves (ed. R M Barrer) |  | 71-77 | 1968 |
| Maricopaite (interrupted framework) | Rouse R C, et al. | Am. Mineral. | 79: | 175-184 | 1994 |
| Na-D | Barrer R M, et al. | J. Chem. Soc. |  | 1561-1571 | 1952 |
| Ptilolite | Discredited |  |  |  |  |
| Arduinite | Discredited |  |  |  |  |
| Flokite | Discredited |  |  |  |  |
| MCM-61 | Valyosik E W | U.S. Pat. No. |  | 5,670,131 | 1997 |
|  | Shantz D F, et al. | Microporous and Mesoporous Materials | 31: | 61-73 | 1999 |
| MCM-35 | Barrett P A, et al. | Chem. Mater. | 11: | 2919-2927 | 1999 |
| UTM-1 | Plevert J, et al. | J. Phys. Chem. B | 103: | 8647-8649 | 1999 |
| ZSM-39 | Schlenker J L, et al. | Nature | 294: | 340-342 | 1981 |
| CF-4 | Long Y, et al. | J. Incl. Phenom. | 5: | 355-362 | 1987 |
| Dodecasil-3C | Gies H | Z. Kristallogr. | 167: | 73-82 | 1984 |
| Holdstite | Smith J V, et al. | Nature | 303: | 223-225 | 1983 |
| ZSM-23 | Schlenker J L, et al. | Private communication |  |  |  |
|  | Rohrman Jr. A C, et al. | Zeolites | 5: | 352-354 | 1985 |
|  | Marler B, et al. | J. Appl. Crystallogr. | 26: | 636-644 | 1993 |
| EU-13 | Araya A, et al. | U.S. Pat. No. |  | 4,581,211 | 1986 |
| ISI-4 | Kakatsu K, et al. | Eur. Pat. Appl. |  | EPA 102,497 | 1984 |
| KZ-1 | Parker L M, et al. | Zeolites | 3: | 8-11 | 1983 |
| ZSM-12 | LaPierre R B, et al. | Zeolites | 5: | 346-348 | 1985 |
|  | Fyfe C A, et al. | J. Phys. Chem. | 94: | 3718-3721 | 1990 |
| [Ga—Si—O]-MTW | Zhi Y X, et al. | Zeolites | 12: | 138-141 | 1992 |
| CZH-5 | Hickson D A, et al. | UK Pat. Appl. |  | GB2079735A | 1981 |
| NU-13 | Whittam T V | Eur. Pat. Appl. |  | EPA0059059 | 1982 |
| TPZ-12 | Sumitani K, et al. | U.S. Pat. No. |  | 4,557,919 | 1985 |
| Theta-3 | Barlow T M | E. Patent |  | A-162,719 | 1985 |
| VS-12 | Reddy K M, et al. | Chem. Commun. |  | 1491-1492 | 1994 |
| MCM-22 | Leonowicz M E, et al. | Science | 264: | 1910-1913 | 1994 |
| ERB-1 | Belussi G, et al. | Eur. Pat. Appl. |  | EPA293032 | 1988 |
| ITQ-1 | Camblor M A, et al. | Chem. Mater. | 8: | 2415-2417 | 1996 |
|  | Camblor M A, et al. | J. Phys. Chem. B | 102: | 44-51 | 1998 |
| PSH-3 | Puppe L, et al. | U.S. Pat. No. |  | 4,439,409 | 1984 |
| SSZ-25 | Zones S I | E. Patent |  | 231,860 | 1987 |

TABLE 4-continued

| Name of Zeolite | First Author Cited | Citation | Vol. | Page or Number | Year |
|---|---|---|---|---|---|
| Natrolite | Pauling L | *Proc. Nat. Acad. Sci.* | 16: | 453-459 | 1930 |
| | Meier W M | *Z. Kristallogr.* | 113: | 430-444 | 1960 |
| [Al—Ge—O]-NAT | Tripathi A, et al. | *J. Mater. Chem.* | 10: | 451-455 | 2000 |
| [Ga—Si—O]-NAT | Xie D, et al. | In *MRS Sym. Proc.* (*Materials Res. Soc.*) | 111: | 147-154 | 1988 |
| |Rb—|[Ga—Ge—O]-NAT | Klaska K H, et al. | *Z. Kristallogr.* | 172: | 167-174 | 1985 |
| Gonnardite | Mazzi F, et al. | *N. Jb. Miner. Mh.* | | 219-228 | 1986 |
| High natrolite | Baur W H, et al. | *N. Jb. Miner. Mh.* | | 171-187 | 1996 |
| Mesolite | Artioli G, et al. | *Acta Crystallogr.* | C42: | 937-942 | 1986 |
| Metanatrolite | Joswig W, et al. | *N. Jb. Miner. Mh.* | | 26-38 | 1995 |
| Scolecite | Taylor W H, et al. | *Z. Kristallogr.* | 86: | 53-64 | 1933 |
| | Fälth L, et al. | *Acta Crystallogr.* | B35: | 1877-1880 | 1979 |
| | Smith J V, et al. | In *Proc. 6$^{th}$ Int. Zeolite Conf.* | | 842-850 | 1984 |
| Synthetic gonnardite | Ghorbarkar H, et al. | *Zeolites* | 19: | 259-261 | 1997 |
| Synthetic mesolite | Ghorbarkar H, et al. | *Cryst. Res. Technol.* | 31: | K67-69 | 1996 |
| Synthetic natrolite | Ghorbarkar H, et al. | *Cryst. Res. Technol.* | 31: | K67-69 | 1996 |
| Synthetic scolecite | Ghorbarkar H, et al. | *Cryst. Res. Technol.* | 31: | K67-69 | 1996 |
| NU-87 | Shannon M D, et al. | *Nature* | 353: | 417-420 | 1991 |
| Gottardite | Alberti A, et al. | *Eur. J. Mineral.* | 8: | 69-75 | 1996 |
| Nonasil | Marler B, et al. | *J. Incl. Phenom.* | 4: | 339-349 | 1986 |
| [B—Si—O]-NON | Marler B, et al. | *Zeolites* | 15: | 517-525 | 1995 |
| |(Co(C$_5$H$_5$)$_2$)$_4$ F4| [Si$_{88}$O$_{176}$]-NON | Vandegoor G, et al. | *Z. Anorg. Allg. Chemie* | 621: | 311-322 | 1999 |
| CF-3 | Long Y-C, et al. | *J. Incl. Phenom.* | 4: | 121-127 | 1986 |
| ZSM-51 | Rohrbaugh W J | Private communication | | | |
| Offretite | Bennett J M, et al. | *Nature* | 214: | 1005-1006 | 1967 |
| | Gard J A, et al. | *Acta Crystallogr.* | B28: | 825-834 | 1972 |
| LZ-217 | Breck D W, et al. | U.S. Pat. No. | | 4,503,023 | 1985 |
| Linde T (ERI-OFF structural intermediate) | Breck D W, et al. | *Zeolite Molecular Sieves* (book) | | 173 | 1974 |
| Synthetic offretite | Ghobarkar H, et al. | *Cryst. Res. Technol* | 31: | K29-31 | 1996 |
| TMA-O | Aiello R, et al. | *Trans. Faraday Soc.* | 66: | 1610-1617 | 1970 |
| UiO-6 | Akporiaye D E, et al. | *Chem. Commun.* | | 1553-1554 | 1996 |
| OSB-1 | Kongshaug K O, et al. | Private communication | | | |
| Parthetite | Engel N, et al. | *Z. Kristallogr.* | 169: | 165-175 | 1984 |
| Paulingite | Gordon E K, et al. | *Science* | 154: | 1004-1007 | 1966 |
| ECR-18 | Vaughn D E W, et al. | U.S. Pat. No. | | 4,661,332 | 1987 |
| Phillipsite | Steinfink H | *Acta Crystallogr.* | 15: | 644-651 | 1962 |
| | Rinaldi R, et al. | *Acta Crystallogr.* | B30: | 2426-2433 | 1974 |
| [Al—Co—P—O]-PHI | Feng P Y, et al. | *Nature* | 388: | 735-741 | 1997 |
| Harmotome | Rinaldi R, et al. | *Acta Crystallogr.* | B30: | 2426-2433 | 1974 |
| | Sadanaga R, et al. | *Acta Crystallogr.* | 14: | 1153-1163 | 1961 |
| ZK-19 | Kuehl G H, et al. | *Am. Mineral.* | 54: | 1607-1612 | 1969 |
| Wellsite (discredited) | Cerny P, et al. | *N. Jb. Miner. Abh.* | 128: | 312-330 | 1977 |
| Rho | Robson H E, et al. | *Adv. Chem. Ser.* | 121: | 106-115 | 1973 |
| | McCusker L B, et al. | In *Proc. 6$^{th}$ Int. Zeolite Conf.* | | 812-822 | 1984 |
| [Be—As—O]-RHO | Gier T E, et al. | *Nature* | 349: | 508-510 | 1991 |
| [Be—P—O]-RHO | Harvey G, et al. | *Stud. Surf. Sci. Catal.* | 49: | 411-420 | 1989 |
| [Co—Al—P—O]-RHO | Feng P, et al. | *Microporous and Mesoporous Materials* | 23: | 315-322 | 1998 |
| [Mg—Al—P—O]-RHO | Feng P, et al. | *Microporous and Mesoporous Materials* | 23: | 315-322 | 1998 |
| [Mn—Al—P—O]-RHO | Feng P, et al. | *Microporous and Mesoporous Materials* | 23: | 315-322 | 1998 |
| Deuterated | Parise J B, et al. | *J. Phys. Chem.* | 88: | 1635-1640 | 1984 |
| Gallosilicate ECR-10 | Newsam J M, et al. | *J. Phys. Chem.* | 99: | 9924-9932 | 1995 |
| LZ-214 | Breck D W, et al. | U.S. Pat. No. | | 4,503,023 | 1985 |
| Pahasapaite | Rouse R C, et al. | *N. Jb. Miner. Mh.* | | 433-440 | 1987 |
| | Rouse R C, et al. | *Am. Mineral.* | 74: | 1195-1202 | 1989 |
| Roggianite | Giuseppetti G, et al. | *N. Jb. Miner. Mh.* | | 307-314 | 1991 |
| RUB-17 | Röhrig C, et al. | *Angew. Chem. Int. Ed.* | 34: | 63-65 | 1995 |
| RUB-3 | Marler B, et al. | *Zeolites* | 15: | 388-399 | 1995 |
| | Marler B, et al. | *Microporous and Mesoporous Materials* | 26: | 49-59 | 1998 |
| RUB-13 | Vortmann S, et al. | *Microporous Materials* | 4: | 111-121 | 1995 |
| RUB-10 | Gies H, et al. | U.S. Pat. No. | | 4,060,590 | 1977 |
| |TMA-|[Si—O]-RUT | Broach R W, et al. | *J. Phys. Chem. Solids* | 56: | 1363-1368 | 1995 |
| B—NU-1 | Belluse G, et al. | *Zeolites* | 10: | 642-649 | 1990 |
| Fe—NU-1 | Belluse G, et al. | *Zeolites* | 10: | 642-649 | 1990 |
| Ga—NU-1 | Belluse G, et al. | *Zeolites* | 10: | 642-649 | 1990 |
| NU-1 | Whittam T V, et al. | U.S. Pat. No. | | 4,060,590 | 1977 |
| STA-1 | Noble G W, et al. | *Angew. Chem. Int. Ed.* | 36: | 81-83 | 1997 |

TABLE 4-continued

| Name of Zeolite | First Author Cited | Citation | Vol. | Page or Number | Year |
| --- | --- | --- | --- | --- | --- |
| STA-6 | Patinec V, et al. | J. Chem. Soc. Dalton Trans. | | 3909-3911 | 1999 |
| STA-2 | Noble G W, et al. | J. Chem. Soc. Dalton Trans. | | 4485-4490 | 1997 |
| Mg-STA-7 | Wright P A, et al. | J. Chem. Soc. Dalton Trans. | | 1243-1248 | 2000 |
| Co-STA-7 | Wright P A, et al. | J. Chem. Soc. Dalton Trans. | | 1243-1248 | 2000 |
| Zn-STA-7 | Wright P A, et al. | J. Chem. Soc. Dalton Trans. | | 1243-1248 | 2000 |
| UCSB-8Co | Bu X H, et al. | Science | 278: | 2080-2085 | 1997 |
| UCSB-8Mg | Bu X H, et al. | Science | 278: | 2080-2085 | 1997 |
| UCSB-8Mn | Bu X H, et al. | Science | 278: | 2080-2085 | 1997 |
| UCSB-8Zn | Bu X H, et al. | Science | 278: | 2080-2085 | 1997 |
| UCSB-6GaCo | Bu X H, et al. | Science | 278: | 2080-2085 | 1997 |
| UCSB-6Co | Bu X H, et al. | Science | 278: | 2080-2085 | 1997 |
| UCSB-6GaMg | Bu X H, et al. | Science | 278: | 2080-2085 | 1997 |
| UCSB-6GaZn | Bu X H, et al. | Science | 278: | 2080-2085 | 1997 |
| UCSB-6Mg | Bu X H, et al. | Science | 278: | 2080-2085 | 1997 |
| UCSB-6Mn | Bu X H, et al. | Science | 278: | 2080-2085 | 1997 |
| UCSB-6Zn | Bu X H, et al. | Science | 278: | 2080-2085 | 1997 |
| UCSB-10GaZn | Bu X H, et al. | Science | 278: | 2080-2085 | 1997 |
| UCSB-10Co | Bu X H, et al. | Science | 278: | 2080-2085 | 1997 |
| UCSB-10Mg | Bu X H, et al. | Science | 278: | 2080-2085 | 1997 |
| UCSB-10Zn | Bu X H, et al. | Science | 278: | 2080-2085 | 1997 |
| SSZ-48 | Wagner P, et al. | J. Phys. Chem. B. | 103: | 8245-8250 | 1999 |
| SSZ-48 | Wagner P, et al. | Angew. Chem. Int. Ed. | 38: | 1269-1272 | 1999 |
| Sigma-2 | McCusker L B, et al. | J. Appl. Crystallogr. | 21: | 305-310 | 1988 |
| Sodalite | Pauling L | Z. Kristallogr. | 74: | 213-223 | 1930 |
| | Loens J, et al. | Acta Crystallogr. | 23: | 434-436 | 1967 |
| [Al—Co—P—O]-SOD | Feng P Y, et al. | Nature | 388: | 735-741 | 1997 |
| [Al—Ge—O]-SOD | Bu X, et al. | J. Am. Chem. Soc. | 120: | 13389-13397 | 1998 |
| [Be—As—O]-SOD | Gier T E, et al. | Angew. Chem., Int. Ed. | 30: | 1169-1171 | 1991 |
| [Be—P—O]-SOD | Gier T E, et al. | Angew. Chem., Int. Ed. | 30: | 1169-1171 | 1991 |
| [Be—Si—O]-SOD | Dann S E, et al. | Inorg. Chem. | 35: | 555-558 | 1996 |
| [Co—Ga—P—O]-SOD | Bu X, et al. | Microporous and Mesoporous Materials | 20: | 371-379 | 1998 |
| [Ga—Co—P—O]-SOD | Feng P Y, et al. | Nature | 388: | 735-741 | 1997 |
| [Ga—Ge—O]-SOD | Bu X, et al. | J. Am. Chem. Soc. | 120: | 13389-13397 | 1998 |
| [Ga—Si—O]-SOD | McCusker L B, et al. | Zeolites | 6: | 388-391 | 1986 |
| [Zn—As—O]-SOD | Nenoff T M, et al. | J. Am. Chem. Soc. | 113: | 378-378 | 1991 |
| [Zn—Ga—As—O]-SOD | Bu X, et al. | Microporous and Mesoporous Materials | 20: | 371-379 | 1998 |
| [Zn—Ga—P—O]-SOD | Bu X, et al. | Microporous and Mesoporous Materials | 20: | 371-379 | 1998 |
| [Zn—P—O]-SOD | Nenoff T M, et al. | J. Am. Chem. Soc. | 113: | 378-378 | 1991 |
| $|Ca_8(WO_4)_2|[Al_{12}O_{24}]$—SOD | Depmeier W | Acta Crystallogr. | C40: | 226-231 | 1984 |
| AlPO-20 + compositional variants | Wilson S T, et al. | J. Am. Chem. Soc. | 104: | 1146-1147 | 1982 |
| | Flanigen E M, et al. | In Proc. 7$^{th}$ Int. Zeolite Conf. | | | 1986 |
| Basic sodalite | Barrer R M, et al. | J. Chem. Soc. | | 1267-1278 | 1951 |
| | Hassan I, et al. | Acta Crystallogr. | C39: | 3-5 | 1983 |
| Bicchulite | Sahl K, et al. | Z. Kristallogr. | 146: | 35-41 | 1977 |
| Danalite | Glass J J, et al. | Am. Mineral. | 29: | 163-191 | 1944 |
| G | Shishakova T N, et al. | Izv. Akad. Nauk SSSR | | 1303- | 1965 |
| Genthelvite | Merlino S | In Feldspars and Feldspathoids (ed. W L Brown) | | 435-470 | 1983 |
| Hauyn | Loehn J, et al. | N. Jb. Miner. Abh. | 109: | 201-210 | 1968 |
| Helvin | Glass J J, et al. | Am. Mineral. | 29: | 163-191 | 1944 |
| Hydroxo sodalite | Felsche J, et al. | Zeolites | 6: | 367-372 | 1986 |
| Nosean | Schulz H, et al. | Tschermaks Min. Petr. Mitt. | 10: | 225-232 | 1965 |
| Silica sodalite | Bibby D M, et al. | Nature | 317: | 157-158 | 1985 |
| TMA sodalite | Baerlocher Ch, et al. | Helv. Chim. Acta | | 1853-1860 | 1969 |
| Tugtupite | Sorensen H | Am. Mineral. | 48: | 1178 | 1963 |
| | Hassan I, et al. | Can. Mineral. | 29: | 385-390 | 1991 |
| SSZ-35 | Wagner P, et al. | Angew. Chem., Int. Ed. | 38: | 1269-1272 | 1999 |
| ITQ-9 | Villaescusa L A, et al. | Chem. Commun. | 21: | 2329-2330 | 1998 |
| Stilbite | Galli E, et al. | Miner. Petrogr. Acta | 12: | 1-10 | 1966 |
| | Slaughter M | Am. Mineral. | 55: | 387-397 | 1970 |
| | Galli E | Acta Crystallogr. | B27: | 833-841 | 1971 |
| Barrerite | Galli E, et al. | Bull. Soc. Fr. Minéral. Cristallogr. | 98: | 331-340 | 1975 |
| Stellerite | Galli E, et al. | Bull. Soc. Fr. Minéral. Cristallogr. | 98: | 11-18 | 1975 |

TABLE 4-continued

| Name of Zeolite | First Author Cited | Citation | Vol. | Page or Number | Year |
|---|---|---|---|---|---|
| Synthetic barrerite | Ghobarkar H, et al. | J. Solid State Chem. | 142: | 451-454 | 1999 |
| Synthetic stellerite | Ghobarkar H, et al. | J. Solid State Chem. | 142: | 451-454 | 1999 |
| Synthetic stilbite Desmine (discredited) Epidesmine (obsolete) | Ghobarkar H, et al. | J. Phys D: Appl. Phys. | 31: | 3172-3176 | 1998 |
| SSZ-23 | Camblor M A, et al. | Angew. Chem. Int. Ed. | 37: | 2122-2126 | 1998 |
| Terranovaite | Galli E, et al. | Am. Mineral. | 82: | 423-429 | 1997 |
| Thomsonite | Taylor W H, et al. | Z. Kristallogr. | 84: | 373-398 | 1933 |
|  | Alberti A, et al. | Zeolites | 1: | 91-97 | 1981 |
|  | Pluth J J, et al. | Zeolites | 5: | 74-80 | 1985 |
| [Al—Co—P—O]-THO | Feng P Y, et al. | Nature | 388: | 735-741 | 1997 |
| [Ga—Co—P—O]-THO | Feng P Y, et al. | Nature | 388: | 735-741 | 1997 |
| Na—V | Barrer R M, et al. | J. Chem. Soc. |  | 195-208 | 1959 |
| Synthetic thomsonite | Ghobarkar, et al. | Cryst. Res. Technol. | 32: | 653-657 | 1997 |
| Theta-1 | Barri S A I, et al. | Nature | 312: | 533-534 | 1984 |
|  | Highcock R M, et al. | Acta Crystallogr. | C41: | 1391-1394 | 1985 |
| ISI-1 | Kozo T, et al. | E Patent |  | A-170,003 | 1986 |
| KZ-2 | Parker L M, et al. | Zeolites | 3: | 8-11 | 1983 |
| NU-10 | Araya A, et al. | Zeolites | 4: | 280-286 | 1984 |
| ZSM-22 | Kokotailo G T, et al. | Zeolites | 5: | 349-351 | 1985 |
|  | Marler B | Zeolites | 7: | 393-397 | 1987 |
| Tscöhrtnerite | Effenberger H, et al. | Am. Mineral. | 83: | 607-617 | 1998 |
| VPI-8 | Freyhardt C C, et a. | J. Am. Chem. Soc. | 118: | 7299-7310 | 1996 |
| VPI-5 | Davis M E, et al. | Nature | 331: | 698-699 | 1988 |
|  | Richardson Jr. J W, et al. | J. Phys. Chem. | 93: | 8212-8219 | 1989 |
|  | McCusker L B, et al. | Zeolites | 11: | 308-313 | 1991 |
| AlPO-54 | Richardson Jr. J W, et al. | J. Phys. Chem. | 93: | 8212-8219 | 1989 |
| H1 | d'Yvoire F | Bull. Soc. Chim. France |  | 1762-1776 | 1961 |
| MCM-9 | Derouane E G, et al. | Appl. Catal. | 51: | L13-20 | 1989 |
| VPI-9 | McCusker L B, et al. | Microporous Materials | 6: | 295-309 | 1996 |
| VPI-7 | Annen M J, et al. | Chem. Commun. |  | 1175-1176 | 1991 |
|  | Röhrig C, et al. | Zeolites | 14: | 498-503 | 1994 |
| Gaultite | Ercit T S, et al. | Can. Mineral. | 32: | 855-863 | 1994 |
| VSV-7# | Röhrig C, et al. | J. Phys. Chem. Solids | 56: | 1369-1376 | 1995 |
| Weinebeneite | Walter F | Eur. J. Mineral. | 4: | 1275-1283 | 1992 |
| Wenkite | Wenk H-R | Z. Kristallogr. | 137: | 113-126 | 1973 |
|  | Merlino S | Acta Crystallogr. | B30: | 1262-1266 | 1974 |
| Yugawaralite | Kerr I S, et al. | Z. Kristallogr. | 125: | 220-225 | 1967 |
|  | Kerr I S, et al. | Acta Crystallogr. | B25: | 1183-1190 | 1969 |
|  | Leimer H W, et al. | Z. Kristallogr. | 130: | 88-111 | 1969 |
| Sr-Q | Hawkins D B | Mater. Res. Bull. | 2: | 951-958 | 1967 |
|  | Kvick Å | Z. Kristallogr. | 174: | 265-281 | 1986 |
| ZAPO-M1 | Marler B, et al. | Microporous Materials | 5: | 151-159 | 1995 |
| GaPO-DAB-2 | Meden A, et al. | Z. Kristallogr. | 212: | 801-807 | 1997 |
| UiO-7 | Akporiaye D E, et al. | Chem. Commun. |  | 601-602 | 1996 |
|  | Akporiaye D E, et al. | J. Phys. Chem. | 100: | 16641-16646 | 1996 |
| CSZ-3 | Vaughn D E W, et al. | U.S. Pat. No. |  | 4,333,859 | 1982 |

The zeolites may be used for oral chelation therapy for heavy metal poisoning, either by natural means such as Wilson's disease and primary biliary cirrhosis, or from environmental exposure such as lead poisoning and intoxication by other various heavy metals such as arsenic, chromium, cesium and strontium including also ammonia, mercaptans and other plant-, marine organism- and nuclear-derived toxins and involving multiple administrations during a single day, single daily, or sequential daily administrations for months to years to slowly remove tissue-bound toxins from the bodies of humans.

The zeolites may be used for therapy for hepatic encephalopathy as an adjunct or alternative to other therapies currently used by binding up chemical mediators of hepatic encephalopathy, which include at least ammonia and mercaptans which are elevated due to poor function of the liver because of its diseased state, which are bound to the zeolite in the gastrointestinal tract and are then removed from the body by fecal elimination. Examples of mercaptans include hydrogen sulfide and alkyl sulfides.

The zeolites may be used in the event of radioactive contamination of food (specifically strontium or cesium, but also other contaminating radionuclides) such that the zeolite is ingested and the radionuclide is adsorbed by the zeolite and carried out of the body (the radionuclide thereby not being absorbed and finding its way into bone or soft tissue where the half-life is substantially prolonged).

The zeolites may be used for treating potassium depletion for patients with elevated potassium in the outpatient or hospital by exploiting their ion-exchange properties in the intestinal juices whereby excess potassium is eliminated with the zeolite in the feces.

The zeolites may be used for oral drug delivery in which the specific framework structure, or mixture of structures chosen, or size of particles, to provide a temporally predictable gastrointestinal absorption profile whereby the zeolite acts a carrier of an active pharmaceutical ingredient which is either slowly or rapidly desorbed out of the zeolite and absorbed by the gastrointestinal tract on a predictable customizable basis.

The zeolites may be used for treating osteoporosis based on the observation that eggshell thickness increases in hens fed a small percentage of their diet as zeolite.

The use of zeolites as the active component for a hemoperfusion device in which blood-borne toxins, whether from an endogenous or exogenous source, are selectively depleted based on the relative affinity of certain zeolites for certain toxins may be used to advantage in a similar way as charcoal is currently used in the hemoperfusion devices.

The zeolites may be used to mitigate against toxic consequences of acrolein exposure in humans.

The zeolites may be used for mitigation, minimization, treatment and prevention of noxious and odoriferous flatulence exploiting the properties of zeolites to selectively absorb hydrogen sulfide, the most odoriferous component of flatulence.

The zeolites may be used for treating hemachromatosis alone or in combination with complementary therapies including therapeutic phlebotomy, erythropoietin administration, desferrioxamine, and other experimental oral and intravenously administered chelating agents.

The zeolites may be used to remove arsenic and decrease toxicity from therapeutic arsenic-containing medications used in the treatment of cancer and infections specifically the cardiac arrhythmia-inducing effects of arsenic.

The zeolites may be used for therapy of acute poisonings from a wide variety of plant, animal, industrial and environmental toxins. These include the mitigation, minimization and elimination of toxin-induced clinical syndromes affecting the cardiovascular, respiratory, gastrointestinal, hepatic, renal, hematopoietic and nervous systems from the following list of plants by their common name, scientific name, toxic part and specific poison:

TABLE 5

Plants, toxic parts, and specific poison

| Common Name | Scientific Name | Toxic part | Toxin | Symtoms/syndrome |
|---|---|---|---|---|
| Akee | *Blighia sapida* | Fruit | Hypoglycins A, B | "Jamaica vomiting sickness" with hypoglycemia, convulstions, coma, lethal |
| Apricot, peach, etc | *Prunus* species | Pit/seed, foliage | Amygdalin glycoside | Cyanide liberation in gut and cyanide poisoning |
| Autumn crocus | *Colchicum autumnale* | All parts of plant | Colchicine alkaloid | Vomiting, diarrhea, shock, death |
| Meadow saffron | *Colchicum autumnale* | All parts of plant | Colchicine alkaloid | Vomiting, diarrhea, shock, death |
| Bird of paradise | *Casealpinia gilliesii* | Pods | Unidentified | Vertigo, vomiting, diarrhea, dehydration |
| Black locust | *Robinia pseudoacacia* | Inner bark, young leaves, seeds | Robin (phytotoxin), robitin (glycoside) | Vomiting, diarrhea, shock, CNS depression |
| Bleeding-heart | *Dicentra formosa* | Foliage, roots | Apomorphine, protoberberine, protopine, other isoquinoline-type alkaloids | Tremors, staggering gait, labored breathing, salivation, convulsions, death due to paralysis |
| Buckeye | *Aesculus* species | Leaves, flowers, seeds | Esculin (glycoside) | Vomiting, diarrhea, pupillary dilatation, ms. Twitching, weakness, ataxia, CNS depression, paralysis |
| Castor bean | *Ricinus communis* | All parts, esp. seeds | Ricin, ricinine (phytotoxins, toxalbumins) | Nausea, vomiting, violent purging, hemolysis, renal failure, oral burning sensation |
| Century plant | *Agave americana* | Sap | Unknown | Skin exposure causes dermatitis associated with leukocytosis and fever |
| Chinaberry | *Melia azedarach* | Fruit | Probably a resinoid | Severe gastroenteritis |
| Christmas rose | *Helleborus niger* | Rootstock and leaves | Helleborin, belleborein (glycosides) | Numbing sensation in mouth, vomiting, diarrhea, convulsions, CNS effects |
| Daphne | *Daphne mezereum* | Berries, bark, leaves | Daphnin, mezerenic acid anhydride | Burning oral sensation, vomiting, blood and mucus in diarrhea, renal failure, weakness, convulsions, death |
| Desert potato | *Jatropha macrorhiza* | Plant root | Phytotoxins | Nausea, vomiting, abdominal cramps, watery diarrhea |
| Dumb cane | *Dieffenbachia seguine* or *picta* | All parts of plant induing sap | Calcium oxalate crystals, toxic protein | Burning sensation of tongue, mouth, larynx; breathing affected |
| Fava bean | *Vicia faba* | Bean, plant pollen | (G6PD deficiencient individuals) | Headache, nausea, vomiting, abdominal pain, icterus hyperthermia, hemolytic anemia, hemogloinuria |
| Four o'clock | *Mirabilis jalapa* | Root, seeds | Trigonelline alkaloid | Skin, mouth, throat irritant causing purgation |
| Foxglove | *Digitalis purpurea* | Leaves and seeds | Digitoxin, digitalin, digitonin glycosides | Cardiac arrhythmia |
| Golden chain | *Laburnum anagyroides* | Beanlike capsules in which seeds are suspended | Quinolizidine alkaloid cytisine | Dysphagia, incoordination, vomiting, renalrfailure, convulsions, coma, death by asphyxiation |

TABLE 5-continued

Plants, toxic parts, and specific poison

| Common Name | Scientific Name | Toxic part | Toxin | Symtoms/syndrome |
|---|---|---|---|---|
| Holly | *Ilex* species | Berries | Ilicin | Nausea, abdominal pain, severe vomiting, diarrhea |
| Hyacinth | *Hyacinthus orientalis* | Bulb | Narcissine-like alkaloid(s) | Digestive upset, vomiting, diarrhea |
| Hydrangea | *Hydrangea* species | All parts of plant | Hydrangin (a cyanogenic glycoside) | Cyanide liberation in gut and cyanide poisoning |
| Indian tobacco | *Loebelia inflata* | All parts of plant | Lobeline and lobelamine alkaloids | Nausea, vomiting, weakness, tremors, convulsions, coma, death |
| Iris (blue flag) | *Iris versicolor* | Leaves and root stalks | Irisin, inidin, irigenin | GI tract, liver, pancreas; purging and congestion of GI tract |
| Jack-in-the-pulpit (Indian turnip) | *Arisaema triphyllium* | Rhizome | Calcium oxalate crystals | Burning sensation of tongue, mouth, larynx; breathing affected |
| Jerusalem cherry | *Solanium pseudocapsicum* | Berries | Solanine and related alkaloids | Headache, abdominal pain, vomiting, diarrhea, circulatory collapse, convulsions; CNS, resp. depression |
| Jimson weed | *Datura stramonium*, *metel*, *inoxia*, *suaveolens*, other species | All parts of plants, especially seeds | Atropine, hyoscyamine, scopolamine (solanaceous alkaloids) | Intense thirst, urinary retention, xerostomia, tachycardia, delirium, incoherence, pyrexia, confulsions, coma, death |
| Lantana | *Lantana camara* | Berries (unripe) | Lantadene A (a polycyclic triterpinoid) | Extreme muscular weakness, GI irritation, lethargy, cyanosis, circulatory collapse |
| Larkspur | *Delphinium ajacis*, other species | Young plant, seeds | Delphinine (?other poisonous alkaloids) | Digestive upset, respiratory depression, parestieias, salivation, headache, hypotension, cardic arrhythmias |
| Lilly of the valley | *Convallaria majalis* | Leaves, flowers, roots | Convallarin, convallamarin, convallatoxin (cardiac glycosides) | Dizziness, vomiting, Cardiac arrhythmias |
| Mistletoe | *Phoradendron* species | Berries | b-phenylethylamine, tyramine, choline | Acute gastroenteritis, circulatory collapse, nausea, vomiting, diarrhea, respiratory difficulties, bradycardia, delirium, hallucinations, coma |
| Monkshood | *Aconitum napellus* | Roots, seeds, leaves | Aconitine (a polycyclic diterpene and other alkaloids) | Vagal stimulation, bradycardia, irregular pulse, dimness of vision, nausea, vomiting, diarrhea, respiratory failure, tingling/numbing of lips, tongue |
| Morning glory | *Ipomoea violacea* | Seeds | Ergine, isoergine, elymoclavine (other olavine alkaloids related to LSD) | Pychotomimetic effects, hallucinations, euphoria, nausea, uterine stimulation |
| Mountain laurel | *Kalmia latifolia* and *augustifolia* | All parts of plant | Andromedotoxin | Stimulation then paralysis of skeletal muscle (curare-like effects), cardiac tissue inhibition, CNS depression, respiratory depression, death |
| Narcissus/daffodil | *Narcissus* species | Bulb | narcissine, lycorine (other alkaloids) | Severe gastroenteritis, vomiting, purging, trembline, convulsions, hypotension, hepatic degeneration |
| Nightshade family | *Solanum* species | Varies with specie | Solanine alkaloids | See Jerusalem cherry |
| Oleander | *Nerium oleander* | All parts | oleandroside, oleandrin nerioside (cardiac glycosides) | Local irritation to mucous membranes, mouth, stomach; nausea, vomiting, diarrhea, slow and irregular pulse changing to rapid/thready pulse, ventricular fibrillation, death |

TABLE 5-continued

Plants, toxic parts, and specific poison

| Common Name | Scientific Name | Toxic part | Toxin | Symtoms/syndrome |
| --- | --- | --- | --- | --- |
| Pencil tree | *Euphorbia tirucalli* | Leaves, stems, milky sap | Unidentified irritant in sap | Irritation to lips, tongue, mouth; skin blisters |
| Peyote | *Lophophora williamsii* and *diffusa* | All parts especially cactus "button" | Mescaline and other alkaloids | Sensory distortion, visual hallucinations |
| Philodendron | *Philodendron* species | Entire plant | Calcium oxalate | Local irritation to mucous membranes, swelling of lips, tongue, excessive salivation, difficulty with swallowing; swelling of tongue, pharynx, inhibits respiration |
| Caladium | *Caladium bicolor* | Entire plant | Calcium oxalate | Local irritation to mucous membranes, swelling of lips, tongue, excessive salivation, difficulty with swallowing; swelling of tongue, pharynx, inhibits respiration |
| Elephant ear | *Colocasia antiquorum* | Entire plant | Calcium oxalate | Local irritation to mucous membranes, swelling of lips, tongue, excessive salivation, difficulty with swallowing; swelling of tongue, pharynx, inhibits respiration |
| Hemlock (poison) | *Conium maculatum* | All parts of plant | Coniium (alkaloid) | Nausea, vomiting, early CNS stimulation followed by severe CNS depression, assoc. muscle paralysis, respiratory failure |
| Poison ivy (erroneously called poison oak) | *Toxicodendron radicans* or *Rhus toxicodendron* | All parts of plant including smoke from burning | Urushiol (comprised of phenolic substances including 3-N-pentadecylcatechol | Severe dermatitis with inflammation, vesicles, blistering |
| Pokeweed (also called pigeonberry, inkberry) | *Phytolacca amnericana* and *decandra* | Roots, leaves and fruit | Saponin, a glycoprotein, phytolaccine, phytolaccotoxin (alkaloids) | Burning sensation in mouth, GI cramps, vomiting, diarrhea; visual disturbance, amblyopia, perspiration, salivation, lassitude, prostration, weakend respiration and pulse, death |
| Privet | *Ligustrum japonicum* | All parts | Possible andromedotoxin, probably unknown | Vomiting, colic, diarrhea, death |
| Red squill | *Urginea maritima* | Bulb | Cardiac glycosides | (see Oleander) |
| Rhododendron (azaela) | *Rhododendron* species | All parts | Andromedotoxin | Salivation, nasal discharge, nausea, vomiting, diarrhea, muscle weakness, labored breathing, coma; dullness of vision, paralysis, hypotension, lacrimation, anorexia |
| Rhubarb | *Rheum rhaponticum* | Leaf blade (not petiole) | Oxalic acid | Severe intermittent abdominal pains, vomiting, diarrhea, headache, weakness, hemorrhages; hypocalcemia causing muscular cramps, tetany; convulsions, coma, death by renal failure |
| Rosary pea (crabseye, precatory bean, jequirity bean, Indiian licorice) | *Abrus precatorius* | Seeds | Abrin (phytotoxin), abric acid (tetanic glycoside) | Burns to mouth, esophagus; like castor bean; nausea, vomiting, severe diarrhea, weakness, shock, trembling hands, oliguria, hemolytic anemia, hallucinations, fatal uremia |
| Star-of-Bethlehem (snowdrop) | *Ornithogalum umbrellatum* | All parts | Colchicine-related alkaloids | Nausea, nervous symptoms, general disturbances of GI tract |
| Sweet pea | *Lathyrus odoratus* | Seeds | Aminopropionitrile | Skeletal deformity and growth suppression; muscle paralysis |
| Texas mountain laurel | *Sophora secundiflora* | Entire plant | Cytisine | Increased salivation, nausea, vomiting, headache, vertigo, confusion, hallucinations, excessive thirst, muscle fasciculation, convulsion, respiratory stimulation then failure |
| Threadleaf groundsel | *Senecio longilobus* | Entire plant (ingested as herbal tea) | Pyrrolizidine alkaloids | Chronic ingestion causes enlarged liver, ascites, abdominal pain, |

TABLE 5-continued

Plants, toxic parts, and specific poison

| Common Name | Scientific Name | Toxic part | Toxin | Symtoms/syndrome |
|---|---|---|---|---|
| Tobacco | *Nicotiana* species | Possibly all parts | Nicotine and related alkaloids | headache, apathy, emaciation; major cause of veno-occlusive disease Nausea, vomiting, muscular fasciculations, early CNS stimulation followed by severe CNS depression assoc. with muscle paralysis and respiratory failure |
| Water hemlock (cowbane) | *Cicuta maculata* and other species | All parts, mostly the roots | Cicutoxin | Severe stomach pain, great mental excitation and frenzy, vomiting, salivation, violent spasmodic convulsions alternating with periods of relaxation, dilated pupils, delirium, death |
| Wisteria | *Wisteria floribunda* (Japanese); *W. sinensis* (Chinese) | Seeds or pods | Wisterin (glucoside) | Mild to severe gastroenteritis, vomiting, abdominal pain, diarrhea |
| Yellow jessamine (Carolina jessamine) | *Gelsmium semperviren* | Whole plant, berries | Gelsemine and gelseminine (alkaloids) | Depress and paralyze nerve motor endings in brain and spinal cord, respiratory arrest |
| Yellow oleander | *Thevetia peruviana* | All parts; fruit "lucky nut" | Thevetin A, B; thevetoxin (cardiac glycosides) | Similar to Oleander; Local irritation to mucous membranes, mouth, stomach; nausea, vomiting, diarrhea, slow and irregular pulse changing to rapid/thready pulse, ventricular fibrillation, death |
| Yew | *Taxus beccata* and *T. canadensis* | All parts, esp. seeds | Taxine (alkaloid) | Nausea, vomiting, diarrhea, abdominal pain, circulatory failure, difficulty breathing; depresses heart function; dermatitis |

The zeolites may be used for treating the following food-borne toxin-induced diseases: cholera, botulism and food poisoning due to *Bacillus cereus* and staphylococcal poisons and *Escherecia coli*; the following toxic marine ingestions: (1) paralytic shellfish poisoning from the ingestion of mussels (*Mytilus edulis* and *Mytilus californianus*), clams (*Saxidomus gigantus* [the Alaskan butter clam] and *Mya arenaria* [the "soft-shell clam" ]), scallops (*Placopecten magellanicus*), oysters which had previous fed upon certain *Gonyaulux* species (which comprise the so-called "red tide") and elaborate saxitoxin 1, neosaxitoxin 2, gonyautoxin 3, gonyautoxin 4 and gonyautoxin 5; (2) pufferfish poisoning ("fugu" in Japan, tambore puffer in China); and (3) ciguatera, from certain fish (such as barracuda, amberjack, kingfish and dolfin) exposed to the benthic dinoflagellate *Gambierdiscus toxicus*; and minimization, mitigation and treatment of any one of the several syndromes arising from the ingestion of toxic mushrooms including stages I, II and II gastroenteritis and hepatorenal syndrome, the anti-cholinergic syndrome, delayed gastroenteritis with CNS abnormalities, cholinergic syndrome, the disulfiram-like reaction with alcohol, hallucinations, delayed gastritis and renal failure and the general gastroenteritis syndromes of nausea, vomiting, abdominal cramping and diarrhea; binding of one or more of the following mushroom poisonous substances including the cyclopeptides amatoxins and phallotoxins, muscimol, ibotenic acid [2552-55-8], gyromitrin monomethyl hydrazine, muscarine, coprine, indole species, orelline, orellanine, psilocin, psilocybin; for one or more of several different mushroom species including *Amanita muscaria* (also known as "fly agaric"), *pantherina, gemata, cokeri, cothurnata, phalloides* (also known as the "death cap"), *verna* (also known as the "death angel"), *virosa* (also known as the "destroying angel"), *bisporigera, ocreata, suballiacae, tenuifolia; Galerina autumnaluis, marginata, venerata; Lepiota helveola, vosserandii, Conocybe filaris, Gyromitra esculenta* (also known as the "false morel"), *gigas, ambigua, infula, cardiniana, brunnea; Paxina* species; *Sarcosphera coronaria; Boletus calopus, luridus, pulcherimus, satanas; Clitocybe clavipes, cerrusata, dealbata, illudens, riuulosa; Inocybe fastigiata, geophylla, lilocina, patuoillaridi, purica, rimosis; Psilocybe cubensis, caerulescens, cyanescens, baeocystis, fimentaria, mexicana, pellulolosa, semilanceata, silvatica; Conocybe cyanopus; Gymnopilus aeruginosa, spectabilis, validipes; Panaeolus subbalteatus* and *foenisecii* (also known as the "mowers' mushroom"); *Stropharis coronillal; Cortinarius orellanus, speciosissimus, splendoma, gentilis; Chlorophyllum molybdites*; and *Orphalates illudens* (also known as the "jack-o-lantern" mushroom).

Dosage and Administration

Preferred dosages are 100-1000 mg sodium aluminosilicate zeolite to a 5-20 kg weight of the human for treating lead poisoning. If the drug is administered to children, the preferred formulation would be as a gelatin capsule with minimal to no water. The number of times it would be administered could be up to 4× per day and could go on daily for more than 1 year. Actual dosage amounts could vary substantially depending on conventional criteria.

For treating excess ammonia, preferred dosages may be about 10 grams to a 70 kg human. This could be up to 4× per day and would be used for up to about −7 days per episode of ammonia-induced encephalopathy. Actual dosage amounts could vary substantially depending on conventional criteria. Preferably, a zeolite formulation would be administered between meals.

Figure 2:
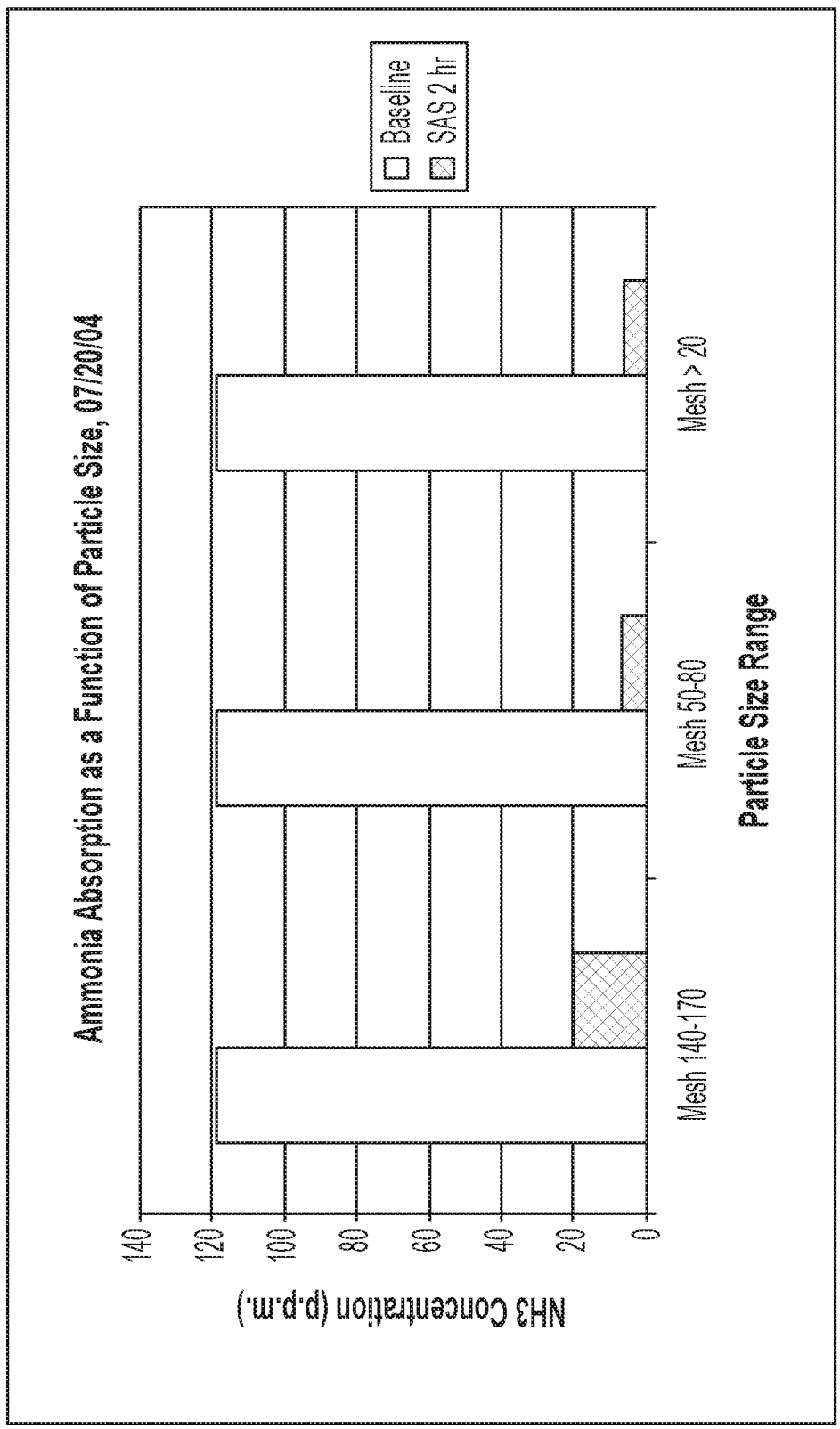
FIG. 2 is a chart showing the relationship between zeolite particle size and ammonium absorption using a zeolite.

The particle size graphs of FIGS. 1-2 show the binding of ammonia using the same mass of sodium aluminosilicate, but with different particle size distributions. It shows that the smaller the particle, the poorer the ammonia binding. Hence, the larger the particle, the more active the drug in binding ammonia. However, there is a practical upper limit for particle size, and that upper limit is palatability. One must strike the right balance that optimizes the trade-off between ammonia binding palatability. Preferably, at least 90% of the particles are of particle size from about 90 μm to about 150 μm. More preferably, at least 95% of the particles are in that range.

The following table present toxicology data on sodium aluminosilicates.

TABLE 6

Toxicology Studies by Oral Gavage Performed with Sodium Aluminosilicate

| Study Author/ Company Report | Animal Toxicology Model | Schedule | Dose Range | Findings | Notes | References |
|---|---|---|---|---|---|---|
| Degussa, 1978 | Rat | Single dose | 5,000 mg/kg to | No Mortality observed | | Degussa A G - US IT No. 78-0012-DKT (unpublished data, 1978) |
| Gloxhuber, 1983 | Rat | | 31,800 mg/kg | | | Gloxhuber Ch, Potokar M, Pittermann W, et al *Food Chem. Toxic.* 21: 209-220 (1983) |
| Gaynor, 1973 | Rat | | | | | Gaynor T, Klusman L. Procter & Gamble Company; Human Safety Appendices on Sodium Aluminosilicate, A.2 (1973) |
| Thomas, 1992 | Rat | | | | | Thomas J, Ballantyne B: *J. of Am. Coll. Of Tox.* 11(3): 259-273 (1992) |
| Moore, 1974 | Rat | | | | | Moore G E, Huntingdon Research Center, Project No. 747-129 in: Procter & Gamble Company; Human Safety Appendices on Sodium Aluminosilicate, A.2 (1974) |
| Moulton, 1974 | Rat | | | | | Moulton R H, Scientific Associates, Inc., S.A. No. 201935 in: Procter & Gamble Company; Human Safety Appendices on Sodium Aluminosilicate, A.2 (1973) |
| Degussa, 1988 | Rat | | | | | Degussa A G - US IT No. 88-0207-DKT (unpublished data, 1988 A) |
| Litton, 1974 | Rat | | | | | Litton Bionetics, Inc."Mutagenic evaluation of compound FDA 71-45, synthetic sodium silicoaluminate," prep. for FDA; NTIS, US Dept. of Commerce, Springfield, VA; PB 245 468 (1974) |
| Huber, 1973 | Rat | | | | | J. M. Huber Corporation; Report date Jan. 12, 1973 (unpublished data) |
| Degussa, 1990A | Rat (GLP) | | 5,110 mg/kg | | | Degussa AG - US IT No. 90-0146-DGT (unpublished data, 1990 A) |
| Degussa, 1990B | | | | | | Degussa AG - US IT No. 90-0149-DGT (unpublished data, 1990 D) |
| Litton, 1974a | Rat | Single dose | | $LD_{50}$ >5000 mg/kg | Identical protocol and laboratory as study below | BgVV (Bundesinstitut für gesundheitlichen Verbraucherschutz und Veterinärmedizin), Ärtzliche Mitteilung bei Vergiftungen 1999, ISBN 3-931675-59-9 |
| Litton, 1974b | Rat | Single dose | | $LD_{50}$ 1050 mg/kg | Results deemed NOT RELIABLE by HERA Panel | BgVV (Bundesinstitut für gesundheitlichen Verbraucherschutz und Veterinärmedizin), Ärtzliche Mitteilung bei Vergiftungen 1999, ISBN 3-931675-59-9 |
| Litton, 1974c | Rat | D x 5 | 5,000 mg/kg/d | No signs of toxicity or abnormal behavior | | Reference not provided in HERA documentation |
| Henkel, 1978 | Mouse | Single dose | 10,000 mg/kg | n/a | | Henkel KgaA, Archive-No. TBD 780104 (Akute Toxizität an der Maus, November 1978) |
| Sturm, 1973 | Dog | Single dose | | n/a | | Sturm R N, Procter & Gamble Company; Human Safety Appendices on Sodium Aluminosilicate, A.3 (1973) |

TABLE 6-continued

Toxicology Studies by Oral Gavage Performed with Sodium Aluminosilicate

| Study Author/ Company Report | Animal Toxicology Model | Schedule | Dose Range | Findings | Notes | References |
|---|---|---|---|---|---|---|
| Henkel, 1979a | Rat (Fischer 344) | D x 14 | 0.000% (w/w) 0.625% (w/w) 1.25% (w/w) 2.5% (w/w) 5.0% (w/w) 10.0% (w/w) | No change in food consumption, no marked signs of toxicity on gross necropsy | | Henkel KgaA, Archive-No. R 0100197 (External Report, Tracor-Jitco, Inc., Jun. 28, 1979, unpublished data) |
| Henkel, 1979b | Mouse (B6C3F1) | D x 14 | 0.000% (w/w) 0.625% (w/w) 1.25% (w/w) 2.5% (w/w) 5.0% (w/w) 10.0% (w/w) | No change in food consumption, no marked signs of toxicity on gross necropsy | | Henkel KgaA, Archive-No. R 0100196 (External Report, Tracor-Jitco, Inc., Jun. 28, 1979, unpublished data) |
| Henkel, 1977 | Rat (Wistar) | D x 90 | 0 ppm (w/w) 1,000 ppm (w/w) 5,000 ppm (w/w) 10,000 ppm (w/w) | High dose group: hyperplastic reaction of tranansitional epithelium with calculi; kidneys of male higher silicate content vs. ctrls: NOAEL 5,000 ppm (250-300 mg/kg/d; 1500-1800 mg/m$^2$/d) | | Henkel KgaA, Archive-No. TBD 770012 Subacute orale Toxizität an Ratten, 90-Tage-Test, January 1977, unpublished data). |
| Henkel, 1975 | Rat (COX-SD) | D x 163 | 0.0% (w/w) 0.5% (w/w) 1.0% (w/w) 2.0% (w/w) | D 28 sac: no Δ; D 84, D 85: 1 death/day: bladder tox, stones; D 93 sac: bladder stones; high dose only; D 163 sac bladder stones 1 animal each in 1.0% and 0.5% groups | | Henkel KgaA, Archive-No. TBD EX 0143 (External Report, Procter & Gamble, September, 1975, unpublished data) |
| Henkel, 1976a | Rat (COX-SD) | D x 160 or D x 200 | 0.0% (w/w) 0.125% (w/w) 2.0% (w/w) | UA: No Δ treated vs. ctrl; bladder tox, stones, xtals in high dose group; no Δ in urine parameter or kidney function; Histopath: ↑ interstitial nephritis, regenerative epithelium and [renal] pelvic epithelial hyperplasia; bladder: ↑ transitional epithelium hyperplasia in high dose group. No histopath Δ in low dose group; NOAEL 0.125% (~69 mg/kg/d; ~420 mg/m$^2$/d) | | Henkel KgaA, Archive-No. TBD EX 0127 (External Report, Procter & Gamble; June, 1976, unpublished data) |
| Henkel, 1976b | Rat (Long-Evans) | D x 168 (24 wk) | 0.0% (w/w) 0.125% (w/w) 0.5% (w/w) 2.0% (w/w) | Regarding mortality, physical appearance, feed efficiency, body weights, organ weights and organ/body ratios no toxic effects observed. Histopath: microscopic alternations in the kidneys at 0.5% | | Two citations for this study: (1) Heakel KgaA, Archive-No, TBD EX 0129 (External Report, Procter & Gamble, May, 1976, unpublished data); (2) Henkel KgaA, Archive-No. TBD EX 0137 (External Pathology Report [13 weeks], Procter & Gamble, March, 1976, unpublished data) |

TABLE 6-continued

Toxicology Studies by Oral Gavage Performed with Sodium Aluminosilicate

| Study Author/ Company Report | Animal Toxicology Model | Schedule | Dose Range | Findings | Notes | References |
|---|---|---|---|---|---|---|
| | | | | and 2.0% groups; NOAEL 0.125% (~69 mg/kg/d; ~420 mg/m$^2$/d) | | |
| Henkel, 1979c | Rat (Wistar) | D x 728 (104 wk) | 0 ppm 10 ppm 100 ppm 1000 ppm | Mortality, feed & water consumption, BW monitored; Ophth, blood, urinary, biochemical params eval.; 104 wk sac: all organs gross/micro eval. No significant test ariticle related effects were observed on histoiopath; no Δ in types or incid. of neoplasms. NOEL 60 mg/kg/d (360 mg/m$^2$/d) | Same study as below, this is part 2 with part 1 below. | Henkel KgaA, Archive-No. SAS 7900017 (Prüfung auf chronischtoxische und tumorerzeugende Wirking von Sasil bei einer Versuchsdauer von 2 Jafaren Teil II, September, 1979, unpublished data) |
| Henkel, 1979d | Rat (Wistar) | D x 728 (104 wk) | 0 ppm 10 ppm 100 ppm 1000 ppm | Mortality, feed & water consumption, BW monitored; Ophth, blood, urinary, biochemical params eval.; 104 wk sac: all organs gross/micro eval. No significant test ariticle related effects were observed on histolopath; no Δ in types or incid. of neoplasms. NOEL 60 mg/kg/d (360 mg/m$^2$/d) | | Henkel KgaA, Archive-No. SAS 7900016 (Prüfung auf chronischtoxische und tumorerzeugende Wirking von Sasil bei einer Versuchsdauer von 2 Jafaren Teil I, September, 1979, unpublished data) |

TABLE 7

Table of Genotoxicity Studies Performed with Sodium Aluminosilicate

| Study Author/ Company Report | Test | Schedule | Strains | Findings | Notes | References |
|---|---|---|---|---|---|---|
| Zeiger, 1987 | Ames | w/ & w/o S9 activation | S. typhimurium TA 98 TA 100 TA 1535 TA 1537 TA 1538 | No mutagenicity detected in any strain | | Zeiger E, Anderson B, Haworth S, et al. *Environmental Mutagenesis* 9 (suppl. 9): 1-110 (1987) |
| Prival, 1991 | Ames | | S. typhimurium TA 98 TA 100 TA 1535 TA 1537 TA 1538 | No mutagenicity detected in any strain | | Two sources cited (1) Prival M J, Simmon V F, Mortelmans K B, *Mutat. Res* 260: 321-329 (1991); (2) Simmon V F and Eckford S L Microbial mutagenesis testing of substances. Compound report: F76-001, sodium aluminum silicate. prep. for FDA; NTIS, US Dept. of Commerce, Springfield, VA; PB89-193650 (1989) |
| Prival, 1991 | Reverse mutation | w/ & w/o S9 activation | E. coli WP2 | | | Two sources cited (1) Prival M J, Simmon V F, Mortelmans K E, *Mutat. Res* 260: 321-329 (1991); (2) Simmon V F and Eckford S L Microbial mutagenesis testing of |

TABLE 7-continued

Table of Genotoxicity Studies Performed with Sodium Aluminosilicate

| Study Author/ Company Report | Test | Schedule | Strains | Findings | Notes | References |
|---|---|---|---|---|---|---|
| | | | | | | substances. Compound report: F76-001, sodium aluminum silicate. prep. for FDA; NTIS, US Dept. of Commerce, Springfield, VA; PB89-193650 (1989) |
| Litton, 1974 | | | S. cerevisiae | Mutagenic potential not reported | | Litton Bionetics, Inc."Mutagenic evaluation of compound FDA 71-45, synthetic sodium silicoaluminate," prep. for FDA; NTIS, US Dept. of Commerce, Springfield, VA; PB 245 468 (1974) |
| Litton, 1974 | | | H. sapiens embryonic lung cell cultures W 38 | No clastogeic potential observed | | Litton Bionetics, Inc."Mutagenic evaluation of compound FDA 71-45, synthetic sodium silicoaluminate," prep. for FDA; NTIS, US Dept. of Commerce, Springfield, VA; PB 245 468 (1974) |
| FASEB, 1977 | | | DNA-repair assay | Negative | | Federation of American Societies of Experimental Biology (FASEB), "Tentative evaluatin of the health aspects of certain silicates as food ingredients" (1977), cited in How M and Solbe J, Unilever Research, Document ref. D/93/021 (1993) |
| Litton, 1974 | Male albino rat (10-12 wk old) | 4.25 mg/kg 42.5 mg/kg 425 mg/kg & 5000 mg/kg | Single dose & D x 5 | No matagenic potential observed | Observation time points: 6, 24, 48 hrs; No Δ in type or number of chromosomal aberrations observed; (+) ctrl → (+) | Litton Bionetics, Inc."Mutagenic evaluation of compound FDA 71-45, synthetic sodium silicoaluminate," prep. for FDA; NTIS, US Dept. of Commerce, Springfield, VA; PB 245 468 (1974) |

TABLE 8

Table of Developmental Toxicology and Teratogenicity Studies Performed with Sodium Aluminosilicate

| Study Author/ Company Report | Model | Schedule | Dose Levels | Findings | Notes | References |
|---|---|---|---|---|---|---|
| Henkel, 1978 | Rat (Charles River; pregnant) | D x 10 on gestational days 6-15 | 0 mg/kg 74 mg/kg 1600 mg/kg (gavage) | D 20 sac: high conception rates; no maternal, embryo or fetal tox noted; no diff in incidence of soft tissue malformations or skeletal defects vs. ctrl NOAEL 1,600 mg/kg (9,600 mg/m$^2$) | | Henkel KgaA, Archive-No. R 0100168 (External Report, Procter & Gamble, May, 1978 unpublished data) |
| FDRL, 1973 | Rat (Wistar, pregnant) | D x 10 on gestational days 6-15 | 0 mg/kg 16 mg/kg 74 mg/kg 345 mg/kg 1,600 mg/kg (gavage) | D 20 sac: no effect on nidation, maternal, or fetal survival noted; no diff in incidence of soft tissue malformations or skeletal defects vs. ctrl NOAEL 1,600 mg/kg (9,600 mg/m$^2$) | | Food and Drug Research Laboratories, Inc. Teratologic Evaluation of FDA 71-45 (sodium silicoaluminate) prep. for FDA, NTIS, US Dept. of Commerce, USA, PB 223 810 (1973) |

TABLE 8-continued

Table of Developmental Toxicology and Teratogenicity Studies Performed with Sodium Aluminosilicate

| Study Author/ Company Report | Model | Schedule | Dose Levels | Findings | Notes | References |
|---|---|---|---|---|---|---|
| FDRL, 1973a | Mouse (CD-I, pregnant) | D x 10 on gestational days 6-15 | 0 mg/kg 16 mg/kg 74 mg/kg 345 mg/kg 1,600 mg/kg (gavage) | D 17 sac: no effect on nidation, maternal, or fetal survival noted; no diff in incidence of soft tissue malformations or skeletal defects vs. ctrl NOAEL 1,600 mg/kg (4,800 mg/m$^2$) | | Food and Drug Research Laboratories, Inc. Teratologic Evaluation of FDA 71-45 (sodium silicoaluminate) prep. for FDA, NTIS, US Dept of Commerce, USA, PB 223 810 (1973) |
| FDRL, 1973b | Rabbit (Dutch; pregnant) | D x 14 on gestational days 6-18 | 0 mg/kg 16 mg/kg 74 mg/kg 345 mg/kg 1,600 mg/kg (gavage) | D 29 sac: no effect on nidation, maternal, or fetal survival noted; no diff in incidence of soft tissue malformations or skeletal defects vs. ctrl NOAEL 1,600 mg/kg (??? conversion mg/m$^2$) | | Food and Drug Research Laboratories, Inc. Teratologic Evaluation of FDA 71-45 (sodium silicoaluminate) prep. for FDA, NTIS, US Dept. of Commerce, USA, PB 223 810 (1973) |
| Henkel, 1978 | Rabbit (New Zealand; pregnant) | D x 14 on gestational days 6-18 | 0 mg/kg 16 mg/kg 74 mg/kg 345 mg/kg 1,600 mg/kg (gavage) | D 29 sac: no effect on maternal toxicity or effect on survival noted; no diff in incidence of soft tissue malformations or skeletal defects vs. ctrl; NOAEL 1,600 mg/kg (??? conversion mg/m$^2$) | | Henkel KgaA, Archive-No. R 0100169 (External Report, Procter & Gamble, June, 1978 unpublished data) |
| FDRL, 1973c | Hamster (Syrian; pregnant) | D x 5 on gestational days 6-10 | 0 mg/kg 16 mg/kg 74 mg/kg 345 mg/kg 1,600 mg/kg (gavage) | D 14 sac: no effect on nidation, maternal, or fetal survival noted; no diff in incidence of soft tissue malformations or skeletal defects vs. ctrl NOAEL 1,600 mg/kg (??? conversion mg/m$^2$) | | Food and Drug Research Laboratories, Inc. Teratologic Evaluation of FDA 71-45 (sodium silicoaluminate) prep. for FDA, NTIS, US Dept. of Commerce, USA, PB 223 810 (1973) |

The following examples are offered by way of illustration and not by way of limitation to the scope of the claims.

EXAMPLES

Example 1: General Manufacturing Process

The synthesis of sodium aluminosilicate consists of one synthetic reaction of aluminum oxide ($Al_2O_3$) (which is dissolved in hot sodium hydroxide in Step I) with liquid sodium silicate ($Na_4SiO_4$) at ambient temperature, to yield the crude sodium aluminosilicate crystalline substance (Step II). The crude crystals are then size reduced by conventional roller milling and size selected (Step III) yielding a uniform granular material. The material is collected in 40 cu. ft. bulk bags (Step IV) and manually transferred to a second size selection step for final size selection (Step V). The resulting size selection process yields a still more uniform particle size distribution of ca. 95% of the crystalline material ranging between 90 and 150 micrometers (μm).

The properly size selected material is washed in a clarification step in which an optimized retrograde flow rate of reverse osmosis (RO) water partially purifies and pH adjusts the crystalline material (Step VI). The material is then gravity-drained and dried with vacuum assistance. The partially purified, pH adjusted, and moist sodium aluminosilicate crystalline material is rehydrated with a saturated saline solution for additional removal of residual alkali and alkaline-earth cations (Step VII). The material is re-dried (Step VIII), and temporarily packaged and stored in fiber drums (Step IX) as the bulk investigational drug substance for shipment to the selected contractor for manufacture of the drug product.

Example 2

The following table provides summary and manufacturing capacity for each synthetic and production step.

TABLE 9

| Step | Process |
|---|---|
| Step I | Dissolution of Aluminum into Sodium Hydroxide |
| Step Ia | Transfer Truck Tank Filling and Reaction Process |
| Step II | Synthesis of Crude Crystalline Substance |
| Step IIa | Maturation and Drying of the Sodium Aluminosilicate |
| Step III | Size Reduction and Selection of the Sodium Aluminosilicate |
| Step IV | Temporary Packaging and Transfer for Second Size Selection |

TABLE 9-continued

| Step | Process |
|---|---|
| Step V | Second Size Selection of Sodium Aluminosilicate |
| Step VI | Clarification of Sodium Aluminosilicate |
| Step VII | Regeneration into the Sodium form of Aluminosilicate |
| Step VIII | Drying of the Regenerated Sodium Aluminosilicate |
| Step IX | Temporary Packaging and Storage of Bulk Drug Substance |

Example 3

Three particle size analyses were performed on the CR-100 zeolite manufactured by Mineral-Right, Inc. The raw data are shown in the table below. FIG. 1 shows a graphical representation of the data.

TABLE 10

| | US Std. Sieve Size | Pre-regeneration (%) | Post-regeneration (%) |
|---|---|---|---|
| Bed #7 | 80 | 0.525 | 1.24 |
| | 100 | 4.65 | 12.36 |
| | 120 | 43.81 | 44.57 |
| | 140 | 37.15 | 30.52 |
| | 170 | 11.79 | 8.65 |
| | 230 | 0.9 | 1.21 |
| | 325 | 0.22 | 0.37 |
| | Pan | 0.43 | 0.12 |
| Bed #10 | 80 | 1.17 | 2.34 |
| | 100 | 4.24 | 18.12 |
| | 120 | 41.4 | 38.6 |
| | 140 | 38.1 | 29.73 |
| | 170 | 12.11 | 8.83 |
| | 230 | 1.05 | 1.06 |
| | 325 | 0.34 | 0.3 |
| | Pan | 0.62 | 0.04 |
| Bed #11 | 80 | 0.64 | 0.72 |
| | 100 | 9.38 | 5.37 |
| | 120 | 35.33 | 39.22 |
| | 140 | 34.7 | 36.57 |
| | 170 | 15.4 | 16.28 |
| | 230 | 2.45 | 3.42 |
| | 325 | 0.67 | 0.31 |
| | Pan | 0.64 | 0.1 |

"Pan" in the table refers to the bottommost item in the vertical series of sieves which is a solid bottom designed to collect all particles, regardless of size, that pass through the smallest sieve, which is generally the sieve second to the bottom. Pre- and post-regeneration refers to the particle size distribution before and after exposure to a saturated brine solution of USP salt. Only the post-regeneration product is envisioned to be used clinically. Particle size distributions may change minimally or substantially with use of other counterions such as potassium, calcium and others cited above.

Example 3

An experiment was performed to measure sodium aluminosilicate binding of undesirable ions, especially heavy metals, from man. The sodium aluminosilicate was manufactured according to the previously described manufacturing process. A man, weighing approximately 90 kilograms, orally self-administered a size 0 conventional pharmaceutical-grade hard gelatin capsule containing approximately 500 milligrams of sodium aluminosilicate (CR-100, manufactured by Mineral-Right, Inc., Phillipsburg, Kans.). The capsule was ingested with approximately 200 milliliters of tap water and was immediately swallowed. The subject did not complain of any adverse gastrointestinal effects such as constipation, diarrhea, pain, bloating, nausea, vomiting, or bloody stools. The sodium aluminosilicate remained in the subject for approximately 24 hours until the subject spontaneously experienced a bowel movement and produced a well-formed brown stool. This material was collected (before it was deposited into toilet and flushed) manually with clean, washed rubber gloves and was visually inspected for small white specks of sodium aluminosilicate material.

Specks of white, granular material that was observed in the stool was carefully teased out by the use of fine plastic tweezers, briefly dipped in deionized water to wash off any potentially contaminating fecal material, and placed in a plastic container that had been previously washed with deionized water and air dried. The amount of sodium aluminosilicate that was recovered was approximately 50 mg. The sodium aluminosilicate collected from the stool (designated "After" in the table below) and sodium aluminosilicate from the same manufacturing process that had not been administered to the subject (designated "Before" in the table below) were analyzed for metallic ion content with atomic absorption spectrophotometry.

The following tabulated results were noted for sodium aluminosilicate manufactured by the method described above with the exception that the material was not fully regenerated with sodium and extensively clarified with deionized water. The table thus reflects analysis of sodium aluminosilicate following passage through the human gastrointestinal tract.

TABLE 11

| | mg/kg (ppm) | | | |
|---|---|---|---|---|
| Cation/Anion | Practical quantification limit* | "new" | "used" | Difference between new and used |
| aluminum | 2,400 | 540,000 | 420,000 | z |
| antimony | 0.7 | nd | nd | |
| arsenic | 7.0 | nd | nd | |
| barium | 3.5 | 9.3 | 5.8 | |
| beryllium | 0.7 | 0.8 | nd | |
| bismuth | 1.1 | nd | nd | |
| boron | 50 | nd | nd | |
| cadmium | 0.8 | nd | nd | |
| calcium | 560 | 14,000 | 2,800 | |
| chromium | 1.5 | nd | nd | |
| cobalt | 1.0 | nd | nd | |
| copper | 2.7 | 10 | 13 | |
| iron | 1,300 | nd | nd | |
| lead | 1.8 | nd | 4.7 | |
| lithium | 3.4 | 3.7 | nd | |
| magnesium | 350 | 3,200 | 1,405 | |
| manganese | 14.0 | nd | nd | |
| mercury | 0.3 | nd | nd | |
| molybdenum | 0.4 | nd | nd | |
| nickel | 2.4 | nd | nd | |
| ammonia nitrogen (mg/L) | 5 | nd | nd | |
| potassium | 150 | 3,300 | 16,000 | |
| selenium | 12 | nd | nd | |
| silicon | 8.4 | 730 | 1,900 | |
| silver | 0.3 | nd | nd | |
| sodium | 410 | 63,000 | 290,000 | |
| strontium | 8.4 | 170 | 72 | |
| thallium | 1.3 | nd | nd | |
| tin | 0.1 | 0.2 | 0.4 | |
| titanium | 5.1 | 18 | 19 | |
| vanadium | 1 | nd | nd | |
| zinc | 21 | nd | 41 | |

*(lowest quantifiable limit of the instrument)

Lead was found in greater concentration after the aluminosilicate had transited the gastrointestinal tract. The sodium aluminosilicate manufactured by Mineral-Right, Inc. may therefore be used as a therapeutic agent for removal of lead in patients with abnormally high levels or toxic burdens of lead. The subject of this experiment was tested for elevated blood lead level. The subject's blood lead level was 7.5 μg/dL which is within normal limits of <10 μg/dL. Sodium aluminosilicate thus possesses utility in treating lead poisoning, and other metals with toxic effects, given that the sodium aluminosilicate was able to extract the toxic metal from an individual who was not suffering from lead poisoning. The same conclusion applies to copper poisoning, which occurs spontaneously though rarely as a clinical entity known as Wilson's disease or hepatolenticular degeneration.

Example 4 (Sorbitol Verses Sorbitol+Zeolite Ammonia Removal Study)

CR-100 is used through out this study. The study compares Sorbitol effect on ammonia to Sorbitol with 2 Zeolite particle sizes, pan, and standard fines. Ammonia challenge solution is approx. 100 Mg/L (100 P.P.M.).

| Sample # 1 | Sample # 2 | Sample # 3 | Sample # 4 | Sample # 5 |
|---|---|---|---|---|
| 10 Gr. Pan | 10 Gr. Fines | 20 Gr. Pan | 20 Cr. Fines | Control; no crystal |
| 100 ML. Sorbitol | Same | Same | Same | Same |
| 100 ML. 95 P.P.M. NH4 | Same | Same | Same | Same |

Each sample is weighed dry, then wetted and added to the 100 mL sorbitol solution spiked with 95 ppm ammonia. The experiment took place in a 250 mL Erlenmeyer flask that was shaken overnight and tested for ammonia the next morning. The concentration of the ammonia in the solution is shown below for each sample.

| Sample # 1 | Sample # 2 | Sample # 3 | Sample # 4 | Sample # 5 |
|---|---|---|---|---|
| 2 P.P.M | 2 P.P.M | 1 P.P.M | 2 P.P.M | 90 P.P.M. |

All publications and patent applications cited in this specification are herein incorporated by reference as if each individual publication or patent application were specifically and individually indicated to be incorporated by reference.

The invention has been described in some detail by way of illustration and example for purposes of clarity of understanding. However the description is not meant to limit the scope of the claims. The invention being thus described, it will be apparent to those skilled in the art that the same may be varied in many ways without departing from the spirit and scope of the invention. Such variations are included within the scope of the following claims.

We claim:

1. A method of treating or palliating elevated human blood ammonia levels, comprising administering to a human suffering from hepatic encephalopathy or cirrhosis of the liver, a pharmaceutical formulation comprising a synthetic sodium aluminosilicate zeolite and a pharmaceutically acceptable adjuvant, wherein:
   (a) the synthetic sodium aluminosilicate is particulate and at least 90% of the particles are of particle size from about 90 μm to about 150 μm;
   (b) the formulation is from about 50% (w/w) to about 95% (w/w) water; and
   (c) the formulation is administered in a doses of from 2 g to 15 g sodium aluminosilicate up to 4 times per day.

2. The method of claim 1, wherein at least about 95% of the particles are of particle size from about 90 μm to about 150 μm.

3. The method of claim 1, wherein the human has a history of liver failure.

4. The method of claim 1, wherein the formulation is a liquid gel administered enterally.

5. The method of claim 1, wherein the human's blood ammonia level is above normal.

6. A method of treating hepatic encephalopathy, comprising administering to a human in need thereof or having a higher than normal risk of hepatic encephalopathy, a pharmaceutical formulation comprising a synthetic sodium aluminosilicate zeolite and a pharmaceutically acceptable adjuvant, wherein:
   the synthetic sodium aluminosilicate is particulate and at least about 95% of the particles are of particle size from about 90 μm to about 150 μm; and
   the formulation is administered in a dose of from 5 g to 12 g sodium aluminosilicate up to 4 times per day.

7. The method of claim 6, wherein the human in need thereof is a hospital patient.

8. The method of claim 6, wherein the human in need thereof has acute or chronic hepatic encephalopathy.

* * * * *